(12) United States Patent
Salmon et al.

(10) Patent No.: US 12,178,960 B2
(45) Date of Patent: Dec. 31, 2024

(54) GENDER BASED FULL-FACE MASK SIZES

(71) Applicant: Fisher & Paykel Healthcare Limited, Auckland (NZ)

(72) Inventors: Andrew Paul Maxwell Salmon, Auckland (NZ); Tony William Spear, Auckland (NZ); Max Leon Betteridge, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 998 days.

(21) Appl. No.: 17/171,341

(22) Filed: Feb. 9, 2021

(65) Prior Publication Data

US 2021/0236760 A1 Aug. 5, 2021

Related U.S. Application Data

(63) Continuation of application No. 15/532,450, filed as application No. PCT/IB2015/059812 on Dec. 21, 2015, now Pat. No. 10,946,154.

(60) Provisional application No. 62/096,524, filed on Dec. 23, 2014.

(51) Int. Cl.
*A61M 16/06* (2006.01)
(52) U.S. Cl.
CPC ........ *A61M 16/0605* (2014.02); *A61M 16/06* (2013.01); *A61M 16/0622* (2014.02); *A61M 16/0683* (2013.01); *A61M 2016/0661* (2013.01)
(58) Field of Classification Search
CPC .......... A41D 13/11–1192; A61M 16/06–0655; A61M 2016/0661
See application file for complete search history.

(56) References Cited

U.S. PATENT DOCUMENTS

| | | |
|---|---|---|
| 2004/0182396 A1 | 9/2004 | Dennis |
| 2006/0283461 A1 | 12/2006 | Lubke et al. |
| 2008/0078396 A1 | 4/2008 | Janbakhsh |
| 2008/0110464 A1 | 5/2008 | Davidson et al. |
| 2009/0126739 A1 | 5/2009 | Ng et al. |
| 2010/0229869 A1 | 9/2010 | Ging et al. |
| 2012/0080035 A1 | 4/2012 | Guney et al. |
| 2012/0222680 A1 | 9/2012 | Eves et al. |

(Continued)

FOREIGN PATENT DOCUMENTS

| | | |
|---|---|---|
| WO | WO 01/87396 A1 | 11/2001 |
| WO | WO 2008/063923 A3 | 5/2008 |

(Continued)

OTHER PUBLICATIONS

International Search Report, PCT/IB2015/059812, dated Apr. 15, 2016 in 3 pages.

(Continued)

*Primary Examiner* — Rachel T Sippel
(74) *Attorney, Agent, or Firm* — VIA LLP

(57) ABSTRACT

A respiratory mask for providing positive pressure therapy having ball jointed elbow, one or more detachable forehead pieces and headgear comprising a spacer fabric region is disclosed herein. The elbow is configured to be removable when oriented to a predetermined position. The forehead pieces are provided in one or more sizes. The spacer fabric region comprises two or more layers wherein the raw edges are turned to the inside of the layers. The seal comprises features that improves seal performance and accommodates a wider variety of facial geometries.

20 Claims, 40 Drawing Sheets

(56) References Cited

U.S. PATENT DOCUMENTS

2013/0152918 A1    6/2013   Rummery et al.
2014/0352134 A1   12/2014   Ho
2015/0040910 A1    2/2015   Koehler
2016/0082213 A1    3/2016   Eifler

FOREIGN PATENT DOCUMENTS

| WO | WO 2012/140514 A1 | 10/2012 |
|----|-------------------|---------|
| WO | WO 2013/170290 A1 | 11/2013 |
| WO | WO 2014/018779 A1 | 1/2014 |
| WO | WO2014/110622 A1 | 7/2014 |
| WO | WO 2014/155270 A1 | 10/2014 |
| WO | WO 2014/175752 A2 | 10/2014 |

OTHER PUBLICATIONS

Yong, Head and Face Anthropometry of Adult U.S. Civilians, Civil Aeromedical Institute Jul. 1993 (Year: 1993).

Standard Small=77x54

Standard Large=100x55

Standard Medium = 89x55
Female Size = 81x50.5
Male Size = 90.5x56.5

GENDER BASED FULL-FACE MASK SIZES

INCORPORATION BY REFERENCE TO PRIORITY APPLICATIONS

This application is a continuation of U.S. application Ser. No. 15/532,450, filed Jun. 1, 2017, which is a continuation of 371 of International Patent Application No. PCT/IB2015/059812, filed Dec. 21, 2015, which is related to and claims priority from U.S. Provisional Patent Application No. 62/096,524, filed Dec. 23, 2014, the entirety of which are hereby incorporated by reference herein and made a part of the present disclosure.

BACKGROUND

Field

The present disclosure generally relates to respiratory masks that cover at least one of a nose and a mouth of a user to supply respiratory gas under positive pressure. More particularly, certain aspects of the present disclosure relate to a respiratory mask with a removable ball jointed elbow, one or more detachable forehead pieces, and spacer fabric headgear. The disclosure also relates to seal cushion arrangements.

Description of Related Art

Respiratory masks can be used to provide respiratory gases to a user under positive pressure. In configurations that include a ball joint, it may be possible for dirt to build up between the ball joint and the socket. Removal of this dirt may be difficult with the ball joint and socket connected. It is also possible for cleaning products to build up in the connection between the ball joint and socket as a result of the surfaces being inaccessible for manual cleaning. The buildup of dirt and/or cleaning products may affect the hygiene of the mask and, thus, limit its useful lifetime. The ball joint is usually permanently connected to its corresponding socket, or it is at least very difficult to remove and/or insert. In some instances removal of the ball joint may require considerable force and may result in permanent damage to the mask.

Respiratory masks are typically available in a range of fixed sizes to suit users with differing facial geometries. This generally involves the manufacture of the entire mask, or at least the major mask components, in a range of sizes; which in turn increases the tooling and manufacturing costs associated with the mask. Another problem associated with fixed mask sizes is that it is possible that a single fixed size mask is not suitable for a particular user's facial geometries. A user's facial geometry may be such that, in order to achieve the best fit possible, the user requires each of the mask components in a different size, which is not possible with a fixed size mask.

Headgear for respiratory masks can traditionally be heavy, bulky, and hot to wear. This can lead to discomfort for the user.

Respiratory masks can have removable cushion modules that can be available in a plurality of sizes. In some cases, the different sizes are simply scaled up from one another in one or more dimensions. Other dimensions can remain the same throughout the different sizes.

SUMMARY

The systems, methods and devices described herein have innovative aspects, no single one of which is indispensable or solely responsible for their desirable attributes. Without limiting the scope of the claims, some of the advantageous features will now be summarized.

It is an object of the present disclosure to provide one or more constructions or methods that will at least go some way towards improving on the above or that will at least provide the public with a useful choice.

In accordance with at least one of the embodiments disclosed herein, a PAP kit comprises a flow generator, humidifier, breathing circuit and an interface, the interface comprising a first mask having a first size and a second mask having a second size different than the first size, wherein the first size is based on facial geometry data of a female population sample and wherein the second size is based on facial geometry data of a male population sample.

According to a further aspect, the first size has a height between an upper portion and a lower portion of the seal measured on a center line of the seal of about 81 mm and a maximum width of an opening of the seal of about 50.5 mm.

According to a further aspect, the second size has a height between an upper portion and a lower portion of the seal measured on a center line of the seal of about 90.5 mm and a maximum width of an opening of the seal of about 56.5 mm.

According to a further aspect, an upper portion of the first and second masks each include a seal having a forwardly-deflectable upper portion, wherein the heights are measured in a relaxed position of the forwardly-deflectable upper portions.

According to a further aspect, the kit further comprises an automatically adjusting headgear.

In accordance with at least one of the embodiments disclosed herein, a mask system comprising a seal support, a first seal and a second seal that are interchangeably mountable to the seal support, the first seal having a first size and a second seal having a second size different than the first size, wherein the first size is based on facial geometry data of a female population sample and wherein the second size is based on facial geometry data of a male population sample.

In accordance with at least one of the embodiments disclosed herein, a mask system comprising a seal support, a first seal and a second seal that are interchangeably coupled to the seal support, the first seal having a first size and a second seal having a second size different than the first size, wherein the second size is between approximately 10-15% greater than the first size in at least one of a height and width direction.

According to a further aspect, the second size is approximately 12% greater than the first size in at least one of a height and width direction.

In accordance with at least one of the embodiments disclosed herein, a mask system comprising a seal support, a first seal and a second seal that are interchangeably coupled to the seal support, the first seal having a first size and a second seal having a second size different than the first size, wherein a difference in height is approximately twice a difference in width between the first size and the second size.

In accordance with at least one of the embodiments disclosed herein, a method of supplying a PAP system, comprising shipping a container containing the PAP system, the PAP system comprising a flow generator, humidifier, breathing circuit and an interface, the interface comprising a first mask having a first size and a second mask having a second size different than the first size.

According to a further aspect, the first size has a height between an upper portion and a lower portion of the seal measured on a center line of the seal of about 81 mm and a maximum width of an opening of the seal of about 50.5 mm.

According to a further aspect, the second size has a height between an upper portion and a lower portion of the seal measured on a center line of the seal of about 90.5 mm and a maximum width of an opening of the seal of about 56.5 mm.

According to a further aspect, an upper portion of the first and second masks each include a seal having a forwardly-deflectable upper portion, wherein the heights are measured in a relaxed position of the forwardly-deflectable upper portions.

According to a further aspect, the method further comprises providing an automatically adjusting headgear.

In accordance with at least one of the embodiments disclosed herein, a method of designing a mask system, comprising designing a seal support, designing a first seal configured to be removably connectable to the seal support, the first seal having a size determined by facial geometry data of a female population sample, designing a second seal configured to be removably connectable to the seal support, the second seal having a size based on facial geometry data of a male population sample.

In accordance with at least one of the embodiments disclosed herein, a method of manufacturing a mask system, comprising making a seal support, making a first seal configured to be removably connectable to the seal support, the first seal having a size determined by facial geometry data of a female population sample, making a second seal configured to be removably connectable to the seal support, the second seal having a size based on facial geometry data of a male population sample.

In accordance with at least one of the embodiments disclosed herein, a method of using a mask system (or PAP system), comprising selecting one of a first seal having a size determined by facial geometry data of a female population sample and a second seal having a size based on facial geometry data of a male population sample, and attaching the selected seal to a seal support.

Additional aspects involve any apparatus, kit or method described above, in combination with or including components having features as described in any of the following paragraphs.

In accordance with at least one of the embodiments disclosed herein, a respiratory mask is provided comprising a cushion module, a mask frame, an elbow, a socket insert, a forehead piece and headgear. The cushion module is configured to substantially surround a user's nose and/or mouth. The cushion module comprises a seal configured to form a substantially airtight seal with a user's face and a seal housing comprising an opening configured to connect to a socket insert. The mask frame comprises a socket connection opening configured to connect to the socket insert, a male forehead piece connector configured to connect to a male forehead piece, and one or more headgear connectors. The elbow comprises a ball joint, which includes an elbow bearing surface, configured to connect to the socket insert, wherein the ball joint includes a tapered chamfer. The elbow further comprises a lip configured to interact with the socket insert during removal of the elbow. The socket insert comprises an inner wall, which comprises a socket bearing surface configured to contact the elbow bearing surface, and an elbow removal notch configured to provide a leverage point for removal of the elbow. The forehead piece is configured to provide a connection between the mask frame and a headgear, wherein the forehead piece is provided in one or more different sizes. The headgear comprises a pair of forehead straps configured to connect to the forehead piece, a crown strap configured to extend across the top of a user's head, a pair of chin straps configured to connect to the headgear connectors, and a spacer fabric pad.

According to a further aspect, the socket insert comprises an outer wall, a front wall, an inner wall, an elbow removal notch and an array of bias-flow holes. The outer wall, the front wall and the inner wall are connected to form a substantially 'u' shaped rear channel. The outer wall comprises a frame connection and a seal housing connection. The inner wall comprises the socket bearing surface. The elbow removal notch is configured to allow the ball joint to be removed from the socket insert.

According to a further aspect, the elbow is removable from the socket insert when oriented to a predetermined position.

According to a further aspect, the spacer fabric pad is located at the rear of the headgear.

According to a further aspect, the spacer fabric pad comprises two or more layers.

According to a further aspect, the two or more layers of spacer fabric are sewn together at the edges with the wrong side of the fabric facing out, and then flipped right-side out so that the raw edges are on the inside.

In accordance with at least one of the embodiments disclosed herein, a cushion module for a respiratory interface includes a seal housing constructed from a relatively rigid material. The seal housing defines an aperture configured to allow a breathing gas to enter an interior of the cushion module. A seal is supported by the seal housing and has an upper portion and a lower portion. The seal further comprises a face contacting surface configured to contact the face of a user and create at least a substantial seal with the face of the user. The face contacting surface has an inner edge defining an opening in the face contacting surface. A portion of the seal defining the face contacting surface comprises a pair of nose pads positioned on each side of the opening in the upper portion of the seal. A laterally inward edge nearest the opening of each of the nose pads is spaced from the opening. A continuous portion of the inner edge of the opening defines a thickness of equal to or less than 0.6 mm. The continuous portion of the inner edge extends inwardly from the inner edge at least 1 mm and extends along at least an entirety of the upper portion of the seal. A portion of the opening in the upper portion of the seal defines a nose bridge portion that contacts a bridge of the user's nose. The nose bridge portion of the opening defines a continuously curved portion of the inner edge. The upper portion of the seal comprises a reduced stiffness portion defined between a first boundary and a second boundary such that the reduced stiffness portion deforms in response to forward movement of an upper portion of the face contacting surface. An angle defined between the first boundary and the second boundary is at least about 25 degrees. The reduced stiffness portion comprises a front wall and a top wall. A height of the front wall is at least about 7 mm. A thickness of the front wall and the top wall progressively increases from a lower end of the front wall to a rearward end of the front wall.

According to a further aspect, the nose pads define the thickest portions of the portion of the seal defining the face contacting surface.

According to a further aspect, a pair of outer peripheral portions defined by the portion of the seal define lateral portions of the face contacting surface, wherein the outer peripheral portions are the next thickest portions after the nose pads.

According to a further aspect, a section of the continuous portion of the inner edge located within 0.5 mm of the inner edge is equal to or less than 0.4 mm in thickness.

According to a further aspect, a width of the nose bridge portion is equal to or less than about 11 mm.

According to a further aspect, a vertical dimension of a vertical center of the nose bridge portion is equal to or greater than about 15 mm.

According to a further aspect, the angle between the first boundary and the second boundary is between about 27 degrees and about 34 degrees.

According to a further aspect, the height of the front wall is between about 7.3 mm and about 7.7 mm.

According to a further aspect, a distance between a point on a centerline of the upper portion and a point on the centerline of the lower portion of a face contacting surface of the seal varies by at least about 5 mm between a neutral position and a depressed position of the reduced stiffness region.

In accordance with at least one of the embodiments disclosed herein, a cushion module for a respiratory interface a seal housing defining aperture configured to allow a breathing gas to enter an interior of the cushion module. A seal is supported by the seal housing and has an upper portion and a lower portion. The seal further comprises a face contacting surface configured to contact the face of a user and create at least a substantial seal with the face of the user. The face contacting surface has an inner edge defining an opening in the face contacting surface. A portion of the seal defining the face contacting surface comprises a pair of nose pads positioned on each side of the opening in the upper portion of the seal. An entirety of each of the nose pads is spaced outwardly from the opening.

According to a further aspect, the nose pads are the thickest portions of the portion of the seal defining the face contact surface.

According to a further aspect, a pair of thickened outer peripheral portions are defined by the portion of the seal defining the face contacting surface, wherein at least a portion of the thickened outer peripheral portions are positioned below the nose pads.

According to a further aspect, at least a portion of the thickened outer peripheral portions are positioned above the nose pads.

In accordance with at least one of the embodiments disclosed herein, a cushion module for a respiratory interface includes a seal housing constructed from a relatively rigid material. The seal housing defines an aperture configured to allow a breathing gas to enter an interior of the cushion module. A seal is supported by the seal housing and has an upper portion and a lower portion. The seal further comprises a face contacting surface configured to contact the face of a user and create at least a substantial seal with the face of the user. The face contacting surface has an inner edge defining an opening in the face contacting surface. A continuous portion of the inner edge of the opening defines a thickness of equal to or less than 0.6 mm. The continuous portion of the inner edge extends inwardly from the inner edge at least 1 mm and extends along at least an entirety of the upper portion of the seal.

According to a further aspect, a section of the continuous portion of the inner edge located within 0.5 mm of the inner edge is equal to or less than 0.4 mm in thickness.

In accordance with at least one of the embodiments disclosed herein, a cushion module for a respiratory interface includes a seal housing constructed from a relatively rigid material. The seal housing defines an aperture configured to allow a breathing gas to enter an interior of the cushion module. A seal is supported by the seal housing and has an upper portion and a lower portion. The seal further comprises a face contacting surface configured to contact the face of a user and create at least a substantial seal with the face of the user. The face contacting surface has an inner edge defining an opening in the face contacting surface. A portion of the opening in the upper portion of the seal defines a nose bridge portion that contacts a bridge of the user's nose. The nose bridge portion of the opening defines a continuously curved portion of the inner edge.

According to a further aspect, a width of the nose bridge portion is equal to or less than about 11 mm.

According to a further aspect, a vertical dimension of a vertical center of the nose bridge portion is equal to or greater than about 15 mm.

According to a further aspect, a depth between a rearmost point of the nose bridge portion and a lower edge of the nose bridge portion on the vertical center of the seal is at least about 4 mm.

According to a further aspect, the depth of the nose bridge portion is about 4.26 mm.

In accordance with at least one of the embodiments disclosed herein, a cushion module for a respiratory interface includes a seal housing constructed from a relatively rigid material. The seal housing defines an aperture configured to allow a breathing gas to enter an interior of the cushion module. A seal is supported by the seal housing and has an upper portion and a lower portion. The seal further comprises a face contacting surface configured to contact the face of a user and create at least a substantial seal with the face of the user. The face contacting surface has an inner edge defining an opening in the face contacting surface. The upper portion of the seal comprises a reduced stiffness portion defined between a first boundary and a second boundary such that the reduced stiffness portion deforms in response to forward movement of an upper portion of the face contacting surface. An angle defined between the first boundary and the second boundary is at least about 20 degrees.

According to a further aspect, the angle between the first boundary and the second boundary is at least about 25 degrees.

According to a further aspect, the angle between the first boundary and the second boundary is between about 27 degrees and about 34 degrees.

According to a further aspect, the angle between the first boundary and the second boundary is one of about 27 degrees, about 29 degrees and about 34 degrees.

According to a further aspect, a distance between a point on a centerline of the upper portion and a point on the centerline of the lower portion of the face contacting surface of the seal varies by more than 2 mm between a neutral position and a depressed position of the reduced stiffness region.

According to a further aspect, the distance between the point on a centerline of the upper portion and the point on the centerline of the lower portion of the face contacting surface of the seal varies by at least about 5 mm, at least about 6 mm, at least about 8 mm or at least about 10 mm or at least about 12 mm between the neutral position and the depressed position of the reduced stiffness region.

According to a further aspect, a set of cushion modules comprises a plurality of the cushion modules described in the above paragraphs in at least two different sizes, wherein the angle is different between the sizes.

According to a further aspect, the set of cushion modules comprises a small, medium and large size, wherein the angle of the small size is greater than the angles of one or both of the medium and large sizes.

According to a further aspect, the angle of the large size is less than the angles of one or both of the small and medium sizes.

According to a further aspect, the angle of the small size is about 34 degrees, the angle of the medium size is about 29 degrees and the angle of the large size is about 27 degrees.

In accordance with at least one of the embodiments disclosed herein, a cushion module for a respiratory interface includes a seal housing constructed from a relatively rigid material. The seal housing defines an aperture configured to allow a breathing gas to enter an interior of the cushion module. A seal is supported by the seal housing and has an upper portion and a lower portion. The seal further comprises a face contacting surface configured to contact the face of a user and create at least a substantial seal with the face of the user. The face contacting surface has an inner edge defining an opening in the face contacting surface. The upper portion of the seal comprises a reduced stiffness portion defined between a first boundary and a second boundary such that the reduced stiffness portion deforms in response to forward movement of an upper portion of the face contacting surface. The reduced stiffness portion comprises a front wall having a height of at least about 7 mm.

According to a further aspect, the height of the front wall is between about 7.3 mm and about 7.7 mm.

According to a further aspect, the height of the front wall is one of about 7.3 mm, about 7.6 mm and about 7.7 mm.

According to a further aspect, a set of cushion modules comprises a plurality of the cushion modules described in the above paragraphs in at least two different sizes, wherein the height of the front wall is different between the sizes.

According to a further aspect, the set of cushion modules comprises a small, medium and large size, wherein the height of the front wall of the small size is less than the height of the front wall of one or both of the medium and large sizes.

According to a further aspect, the height of the front wall of the large size is greater than the height of the front wall of one or both of the small and medium sizes.

According to a further aspect, the height of the front wall of the small size is about 7.3 mm, the height of the front wall of the medium size is about 7.6 mm and the height of the front wall of the large size is about 7.7 mm.

In accordance with at least one of the embodiments disclosed herein, a cushion module for a respiratory interface includes a seal housing constructed from a relatively rigid material, the seal housing defining an aperture configured to allow a breathing gas to enter an interior of the cushion module. A seal is supported by the seal housing and has an upper portion and a lower portion. The seal further comprises a face contacting surface configured to contact the face of a user and create at least a substantial seal with the face of the user. The face contacting surface has an inner edge defining an opening in the face contacting surface. The upper portion of the seal comprises a reduced stiffness portion defined between a first boundary and a second boundary such that the reduced stiffness portion deforms in response to forward movement of an upper portion of the face contacting surface. A distance between a point on a centerline of the upper portion and a point on the centerline of the lower portion of the face contacting surface of the seal varies by more than 2 mm between a neutral position and a depressed position of the reduced stiffness region.

According to a further aspect, the distance between the point on a centerline of the upper portion and the point on the centerline of the lower portion of the face contacting surface of the seal varies by at least about 5 mm, at least about 6 mm, at least about 8 mm or at least about 10 mm or at least about 12 mm between the neutral position and the depressed position of the reduced stiffness region.

According to a further aspect, the distance varies between about 90 mm to about 84 mm between the neutral position and the depressed position of the reduced stiffness region.

According to a further aspect, the distance varies by at least about 5 percent between the neutral position and the depressed position of the reduced stiffness region.

According to a further aspect, the distance varies by at least about 6 and ⅔ percent between the neutral position and the depressed position of the reduced stiffness region.

In accordance with at least one of the embodiments disclosed herein, a cushion module for a respiratory interface includes a seal housing constructed from a relatively rigid material. The seal housing defines an aperture configured to allow a breathing gas to enter an interior of the cushion module. A seal is supported by the seal housing and has an upper portion and a lower portion. The seal further comprising a face contacting surface configured to contact the face of a user and create at least a substantial seal with the face of the user. The face contacting surface has an inner edge defining an opening in the face contacting surface. The upper portion of the seal comprises a reduced stiffness portion defined between a first boundary and a second boundary such that the reduced stiffness portion deforms in response to forward movement of an upper portion of the face contacting surface. A thickness of the front wall and the top wall progressively increases from a lower end of the front wall to a rearward end of the front wall.

In accordance with at least one of the embodiments disclosed herein, a respiratory interface comprises a frame and a cushion module. The cushion module comprises a seal housing supporting a seal. The seal housing defines an aperture configured to allow a breathing gas to enter an interior of the cushion module. The seal has an upper portion and a lower portion. The seal further comprises a face contacting surface configured to contact the face of a user and create at least a substantial seal with the face of the user. The face contacting surface has an inner edge defining an opening in the face contacting surface. The upper portion of the seal comprises a reduced stiffness portion defined between a first boundary and a second boundary such that the reduced stiffness portion deforms in response to forward movement of an upper portion of the face contacting surface. An angle defined between the first boundary and the second boundary is at least about 25 degrees. The interface further comprises a conduit connector, wherein the frame, the cushion module and the conduit connector are configured for assembly to one another such that the cushion module and the conduit connector are supported relative to the frame with the conduit connector configured to introduce a flow of breathing gas into the interior of the cushion module through the aperture. A headgear is connectable to one of the frame and the cushion module for securing the respiratory interface to the user.

According to a further aspect, a portion of the seal defining the face contacting surface comprises a pair of nose pads positioned on each side of the opening in the upper portion of the seal, wherein a laterally inward edge nearest the opening of each of the nose pads is spaced from the opening.

According to a further aspect, a continuous portion of the inner edge of the opening defines a thickness of equal to or less than 0.6 mm, wherein the continuous portion of the inner edge extends inwardly from the inner edge at least 1 mm and extends along at least an entirety of the upper portion of the seal.

According to a further aspect, a portion of the opening in the upper portion of the seal defines a nose bridge portion that contacts a bridge of the user's nose, wherein the nose bridge portion of the opening defines a continuously curved portion of the inner edge.

According to a further aspect, the reduced stiffness portion comprises a front wall and a top wall, wherein a height of the front wall is at least about 7 mm.

According to a further aspect, a thickness of the front wall and the top wall progressively increases from a lower end of the front wall to a rearward end of the front wall.

According to a further aspect, the conduit connector comprises an elbow that is supported relative to the frame or cushion module by a ball joint.

According to a further aspect, the ball joint is removable.

According to a further aspect, the elbow comprises bias flow holes.

According to a further aspect, the elbow comprises an anti-asphyxiation valve.

In accordance with at least one of the embodiments disclosed herein, a PAP kit is provided. The PAP kit comprises an interface with a first seal having a first size and a second seal having a second size that is different than the first size.

According to a further aspect, the PAP kit further comprises a frame, wherein the first seal and the second seal are configured to be removably and interchangeably connectable to the frame.

According to a further aspect, the PAP kit further comprises at least one headgear. The at least one headgear is configured to be removably and interchangeably connectable to the first seal and the second seal, or the at least one headgear comprises a first headgear configured to be removably connectable to the first seal and a second headgear configured to be removably connectable to the second seal. Further, the length of the straps of the at least one headgear are configured to be varied depending on whether attached to the first seal or the second seal. Even further, the first headgear has a size configured to fit a head of a female and the second headgear configured to fit a head of a male.

According to a further aspect, the first size has a height of about 81 mm when measured along a center line of the seal between a midpoint in a chin region and a midpoint in a nasal bridge region and a width of about 50.5 mm when measured horizontally between edges of an opening of the seal.

According to a further aspect, the second size has a height of about 90.5 mm when measured along a center line of the seal between a midpoint in a chin region and a midpoint in a nasal bridge region and a width of about 56.5 mm when measured horizontally between edges of an opening of the seal.

According to a further aspect, the first size seals a maximum lip length of 65 mm.

According to a further aspect, the second size seals a maximum lip length of 76 mm.

According to a further aspect, a lip length between 51.5 mm and 59.5 mm is sealed by both the first size and the second size.

According to a further aspect, the second size seals users has a Sublabiale-Sellion height between 83 mm and 103 mm.

According to a further aspect, a Sublabiale-Sellion height between 84.5 mm and 96 mm may be sealed by both the first size and the second size.

According to a further aspect, a width of an opening of the second size is approximately 0% to 22.9% greater than a width of an opening of the first size, when measured horizontally between edges of the openings.

According to a further aspect, a width of an opening of the second size is approximately 11.9% greater than a width of an opening of the first size.

According to a further aspect, a width of an opening of the second size is approximately 1 mm to 11 mm greater than a width of an opening of the first size, when measured horizontally between edges of the openings.

According to a further aspect, a width of an opening of the second size is approximately 6 mm greater than a width of an opening of the first size.

According to a further aspect, a difference in height is approximately twice a difference in width between the first size and the second size, the height being measured along a center line of the seal between a midpoint in a chin region and a midpoint in a nasal bridge region and the width being measured horizontally between edges of an opening of the seal.

According to a further aspect, a difference in height between the first size and the second size is equal to or less than 9.5 mm, the height being measured along a center line of the seal between a midpoint in a chin region and a midpoint in a nasal bridge region.

According to a further aspect, a difference in height between the first size and the second size is equal to or less than 11.7%, the height being measured along a center line of the seal between a midpoint in a chin region and a midpoint in a nasal bridge region.

According to a further aspect, a width of the first size is between 57.5% to 67.5% of a height of the first size, the height being measured along a center line of the seal between a midpoint in a chin region and a midpoint in a nasal bridge region and the width being measured horizontally between edges of an opening of the seal.

According to a further aspect, a difference in height between the first size and the second size is equal to or less than 9.5 mm, the height being measured along a center line of the seal between a midpoint in a chin region and a midpoint in a nasal bridge region.

According to a further aspect, a difference in height between the first size and the second size is equal to or less than 11.7%, the height being measured along a center line of the seal between a midpoint in a chin region and a midpoint in a nasal bridge region.

According to a further aspect, a width of the first size is between 57.5% to 67.5% of a height of the first size, the height being measured along a center line of the seal between a midpoint in a chin region and a midpoint in a nasal bridge region and the width being measured horizontally between edges of an opening of the seal.

According to a further aspect, the width of the first size is 62.3% of the height of the first size.

According to a further aspect, a width of the second size is between 58.1% to 67.0% of a height of the second size, the height being measured along a center line of the seal between a midpoint in a chin region and a midpoint in a nasal bridge region and the width being measured horizontally between edges of an opening of the seal According to a further aspect, the width of the second size is 62.4% of the height of the second size.

According to a further aspect, the first size and the second size have equal width versus height proportions.

According to a further aspect, an upper portion of the first and second seals each include a seal having a forwardly-deflectable upper portion, wherein the heights are measured in a relaxed position of the forwardly-deflectable upper portions.

According to a further aspect, the forwardly-deflectable upper portion rolls in a forward direction relative to a lower portion of the seal.

According to a further aspect, the PAP kit further comprises an automatically adjusting headgear.

In accordance with at least one of the embodiments disclosed herein, a mask system is provided. The mask system comprises a mask frame, a first seal and a second seal that are interchangeably mountable to the mask frame. The first seal has a first size and a second seal has a second size different than the first size.

According to a further aspect, the first size has a height of about 81 mm when measured along a center line of the seal between a midpoint in a chin region and a midpoint in a nasal bridge region and a width of about 50.5 mm when measured horizontally between edges of an opening of the seal.

According to a further aspect, the second size has a height of about 90.5 mm when measured along a center line of the seal between a midpoint in a chin region and a midpoint in a nasal bridge region and a width of about 56.5 mm when measured horizontally between edges of an opening of the seal.

According to a further aspect, the first size seals a maximum lip length of 65 mm.

According to a further aspect, the second size seals a maximum lip length of 76 mm.

According to a further aspect, a lip length between 51.5 mm and 59.5 mm is sealed by both the first size and the second size.

According to a further aspect, the second size seals users has a Sublabiale-Sellion height between 83 mm and 103 mm.

According to a further aspect, a Sublabiale-Sellion height between 84.5 mm and 96 mm may be sealed by both the first size and the second size.

According to a further aspect, a width of an opening of the second size is approximately 0% to 22.9% greater than a width of an opening of the first size, when measured horizontally between edges of the openings.

According to a further aspect, a width of an opening of the second size is approximately 11.9% greater than a width of an opening of the first size.

According to a further aspect, a width of an opening of the second size is approximately 1 mm to 11 mm greater than a width of an opening of the first size, when measured horizontally between edges of the openings.

According to a further aspect, a width of an opening of the second size is approximately 6 mm greater than a width of an opening of the first size.

According to a further aspect, a difference in height is approximately twice a difference in width between the first size and the second size, the height being measured along a center line of the seal between a midpoint in a chin region and a midpoint in a nasal bridge region and the width being measured horizontally between edges of an opening of the seal.

According to a further aspect, a difference in height between the first size and the second size is equal to or less than 9.5 mm, the height being measured along a center line of the seal between a midpoint in a chin region and a midpoint in a nasal bridge region.

According to a further aspect, a difference in height between the first size and the second size is equal to or less than 11.7%, the height being measured along a center line of the seal between a midpoint in a chin region and a midpoint in a nasal bridge region.

According to a further aspect, a width of the first size is between 57.5% to 67.5% of a height of the first size, the height being measured along a center line of the seal between a midpoint in a chin region and a midpoint in a nasal bridge region and the width being measured horizontally between edges of an opening of the seal.

According to a further aspect, the width of the first size is 62.3% of the height of the first size.

According to a further aspect, a width of the second size is between 58.1% to 67.0% of a height of the second size, the height being measured along a center line of the seal between a midpoint in a chin region and a midpoint in a nasal bridge region and the width being measured horizontally between edges of an opening of the seal.

According to a further aspect, the width of the second size is 62.4% of the height of the second size.

According to a further aspect, the first size and the second size have equal width versus height proportions.

According to a further aspect, an upper portion of the first and second seals each include a seal having a forwardly-deflectable upper portion, wherein the heights are measured in a relaxed position of the forwardly-deflectable upper portions.

According to a further aspect, the forwardly-deflectable upper portion rolls in a forward direction relative to a lower portion of the seal.

According to a further aspect, the mask system further comprises an automatically adjusting headgear.

In accordance with at least one of the embodiments disclosed herein, a method of providing a mask system is provided. The method comprises providing a mask frame, a first seal and a second seal. The first seal and the second seal are interchangeable with each other and removably connectable to the mask frame. The first seal has a size determined by facial geometry data of a female population sample and the second seal has a size based on facial geometry data of a male population sample.

According to a further aspect, a width of the first seal is between 57.5% to 67.5% of a height of the first seal.

According to a further aspect, the width of the first seal is 62.3% of the height of the first seal.

According to a further aspect, a width of the second seal is between 58.1% to 67.0% of a height of the second seal.

According to a further aspect, the width of the second seal is 62.4% of the height of the second seal.

According to a further aspect, a width of the second seal is approximately 0% to 22.9% greater than a width of the first seal.

According to a further aspect, a width of the second seal is approximately 11.9% greater than a width of the first seal.

According to a further aspect, a difference in height between the first seal and the second seal is equal to or less than 11.7%.

According to a further aspect, the first seal and the second seal have equal width versus height proportions.

In accordance with at least one of the embodiments disclosed herein, a method of using a mask system is provided. The method comprises selecting one of a first seal having a size determined by facial geometry data of a female population sample and a second seal having a size based on facial geometry data of a male population sample, and attaching the selected seal to a seal support.

According to a further aspect, the first seal and the second seal have a size based on at least one of face lengths, lip lengths or Sublabiale-Sellion heights.

According to a further aspect, the first seal and the second seal have a size based on median values of at least one of face lengths, lip lengths or Sublabiale-Sellion heights.

According to a further aspect, the first seal and the second seal are configured to seal 95% of the male and female population samples.

According to a further aspect, a width of the first seal is between 57.5% to 67.5% of a height of the first seal.

According to a further aspect, the width of the first seal is 62.3% of the height of the first seal.

According to a further aspect, a width of the second seal is between 58.1% to 67.0% of a height of the second seal.

According to a further aspect, the width of the second seal is 62.4% of the height of the second seal.

According to a further aspect, a width of the second seal is approximately 0% to 22.9% greater than a width of the first seal.

According to a further aspect, a width of the second seal is approximately 11.9% greater than a width of the first seal.

According to a further aspect, a difference in height between the first seal and the second seal is equal to or less than 11.7%.

According to a further aspect, the first seal and the second seal have equal width versus height proportions.

In accordance with at least one of the embodiments disclosed herein, a method of designing a mask system is provided. The method comprises designing a mask frame, designing a first seal and a second seal to be interchangeable with each other and removably connectable to the mask frame, and sizing the first seal to be smaller than the second seal.

According to a further aspect, sizing the first seal to be smaller than the second seal includes sizing a height relative to a width of the seals, with the height being measured along a center line of the seal between a midpoint in a chin region and a midpoint in a nasal bridge region and the width being measured horizontally between edges of an opening of the seal.

According to a further aspect, a width of the first seal is between 57.5% to 67.5% of a height of the first seal.

According to a further aspect, the width of the first seal is 62.3% of the height of the first seal.

According to a further aspect, a width of the second seal is between 58.1% to 67.0% of a height of the second seal.

According to a further aspect, the width of the second seal is 62.4% of the height of the second seal.

According to a further aspect, a width of the second seal is approximately 0% to 22.9% greater than a width of the first seal.

According to a further aspect, a width of the second seal is approximately 11.9% greater than a width of the first seal.

According to a further aspect, a difference in height between the first seal and the second seal is equal to or less than 11.7%.

According to a further aspect, the first seal and the second seal have equal width versus height proportions.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through the use of the accompanying drawings.

DETAILED DESCRIPTION

Figure 1A:
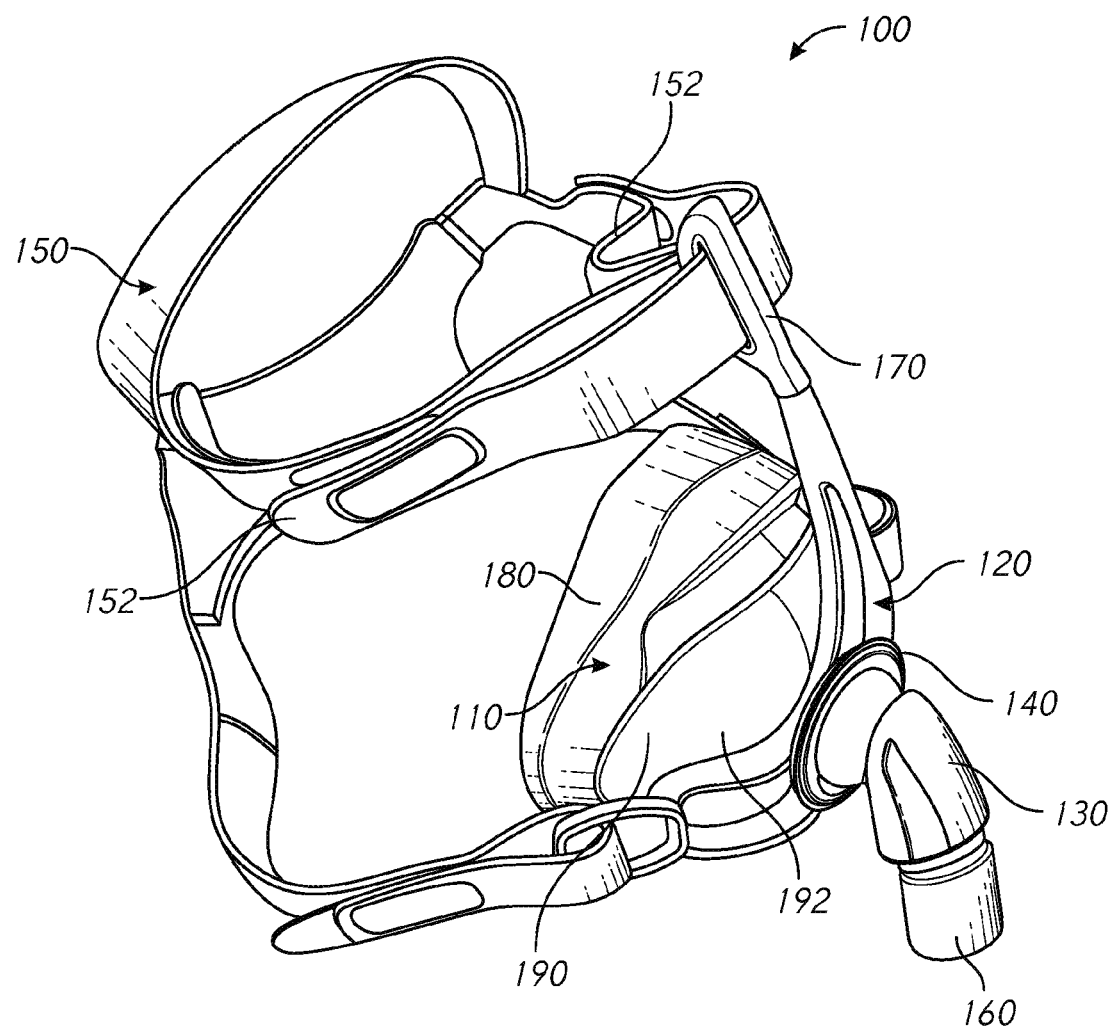
FIG. 1a is a perspective view of the respiratory mask of the present disclosure.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. As used herein the terms 'front', 'rear', 'upper' and 'lower' shall refer to the location of a part or portion of a respiratory mask in relation to a user. Wherein, 'front' refers to a location that is distal to the user (when the mask is in use) and 'rear' refers to a location that is proximal to the user by comparison. The terms 'upper' and 'lower' refer to the location of a part or component of a mask relative to the rest of the mask when the mask is in use and the user is sitting in an upright position. Moreover, terms such as "first," "second," "third," and so on may be used to describe separate components. Such terminology may include the words specifically mentioned above, derivatives thereof, and words of similar import.

Respiratory Mask:

FIG. 1a shows a respiratory mask 100 that incorporates a removable ball jointed elbow and other mask components. The respiratory mask 100 comprises a cushion module 110, a mask frame 120, an elbow 130, a socket insert 140, headgear 150, a swivel 160 and a forehead piece 170.

Figure 1B:
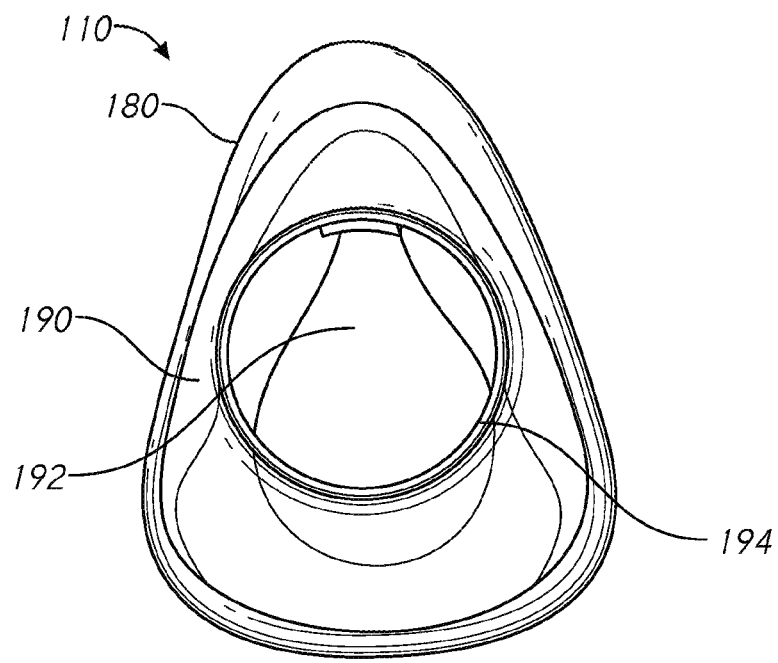
FIG. 1b is a front view of the cushion module of the present disclosure.

The cushion module 110 is configured to substantially surround a user's nose and/or mouth (when in use). The cushion module 110 comprises a seal 180 and a seal housing 190, wherein the seal 180 is configured to contact the user's face and to form a substantially airtight seal. The seal 180 is over-moulded to the seal housing 190. The seal housing 190 comprises a substantially enclosed breathing chamber 192 and an annular opening 194 as shown in FIG. 1b. The annular opening 194 is configured to receive and connect to the socket insert 140 and to allow a flow of air to pass into the breathing chamber 192. In other embodiments, the annular opening 194 may be replaced with an opening of any other appropriate geometry.

Figure 2A:
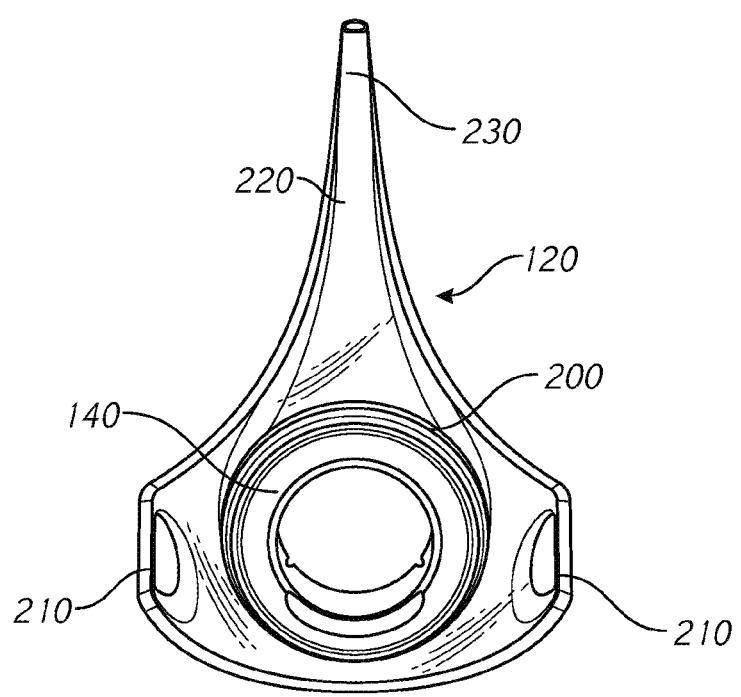
FIG. 2a is a front view of the mask frame of the present disclosure.

Mask Frame:

As shown in FIG. 2a, the mask frame 120 comprises a socket connection opening 200, headgear connectors 210, a bridge portion 220 and a male forehead piece connector 230. The socket insert is configured to be insertable into the socket connection opening 200. In some configurations, the socket insert is configured to be permanently connected to the socket insert 140. The socket insert 140 provides a socket for the elbow 130 (see e.g., FIG. 1a), such that the socket connection opening 200 and the elbow 130 provide a path through which air is supplied to the breathing chamber 192 (shown in FIGS. 1a and 1b).

The headgear connectors provide means for the headgear 150 to be connected to the mask frame 120 (as shown in FIG. 1a) such that a retaining and sealing force can be applied to the mask. The mask frame 120 has a relatively triangular shape, wherein the headgear connectors form two lower points (when worn and the user is sitting in an upright position) and the male forehead piece connector 230 forms the third upper point. The edges of the mask frame 120 that extend from the headgear connectors 210 to the male forehead piece connector 230 have a concave curve that narrows the frame 120 to form an elongate bridge portion 220. The bridge portion 220 is configured to pass over the user's nose. At the upper end, the bridge portion 220 is narrower than the user's nasal bridge such that interference with the user's line of sight is minimized.

Figure 2B:
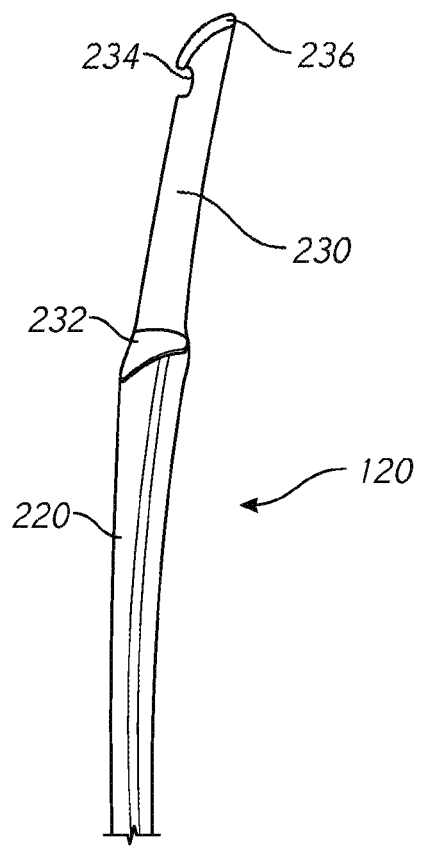
FIG. 2b is a close up side view of the male forehead piece connector.

As shown in FIG. 2b, the bridge portion 220 is terminated at the upper end by the male forehead piece connector 230. The male forehead piece connector 230 comprises a step 232 and a notch 234. The step 232 is provided at the transition between the bridge portion 220 and the male forehead piece connector 230. At this location, there is a step down in the geometry of bridge portion such that the male forehead piece connector is narrower and thinner but follows substantially the same lines as the bridge portion. This allows the male forehead piece connector 230 to fit inside a corresponding female geometry in the forehead piece 170 (see e.g., FIGS. 1a and 6a-e). The male forehead piece connector also includes a notch 234, which is located proximal to an upper end 236 of the mask frame 120. The notch is configured to provide a snap fit connection with corresponding geometry in the forehead piece 170.

Figure 3A:
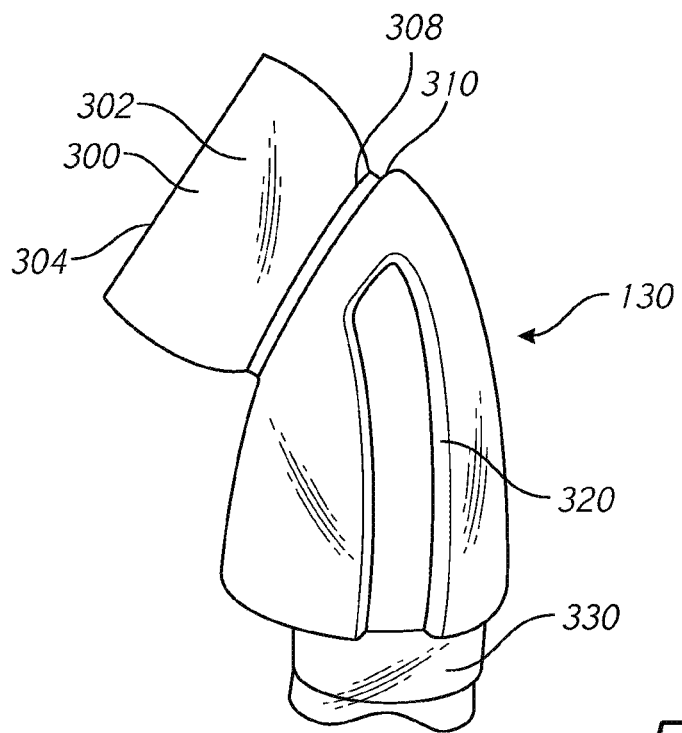
FIG. 3a is a side view of a prior art elbow.
Figure 3B:
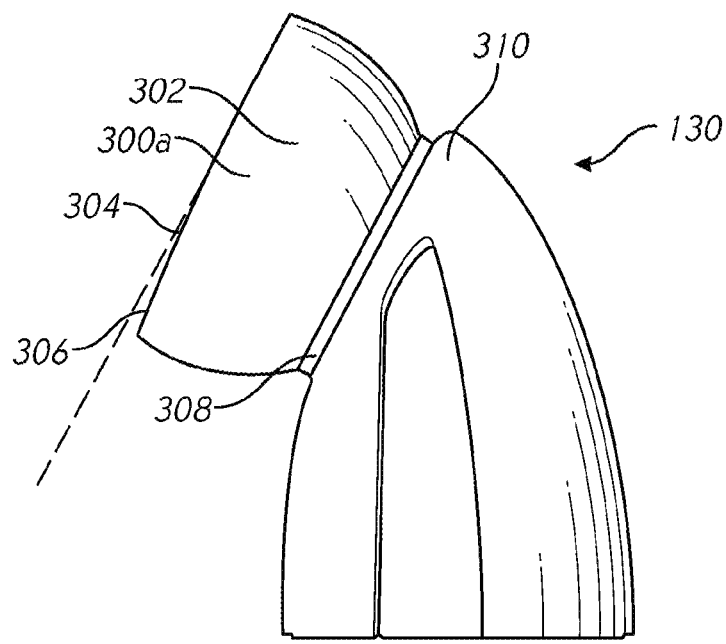
FIG. 3b is a side view of an alternative elbow embodiment.
Figure 4A:
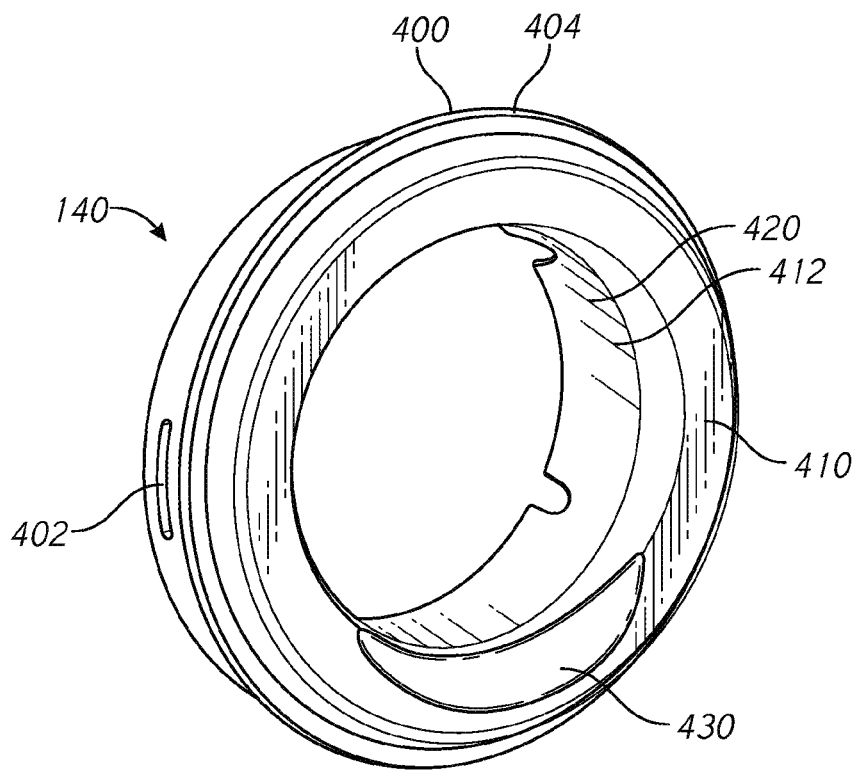
FIGS. 4a to 4e show various views of the socket insert of the present disclosure.
Figure 4B:
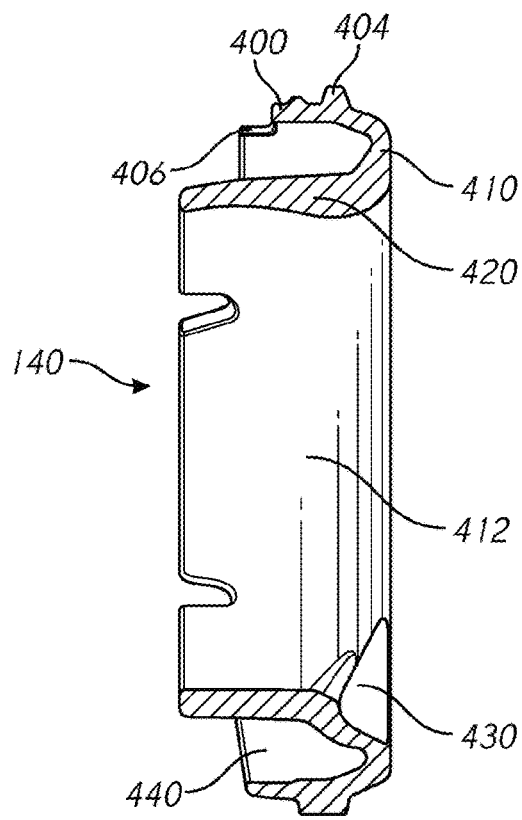
Figure 4C:
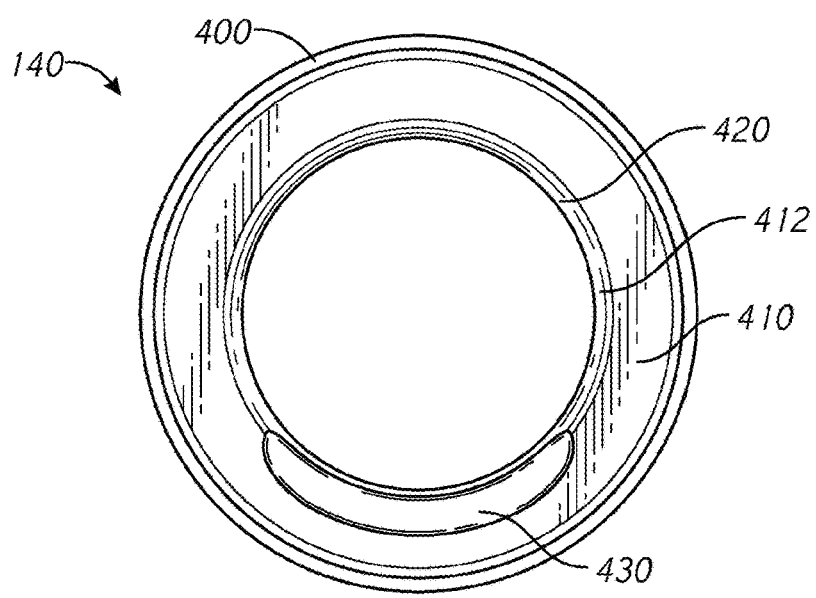
Figure 4D:
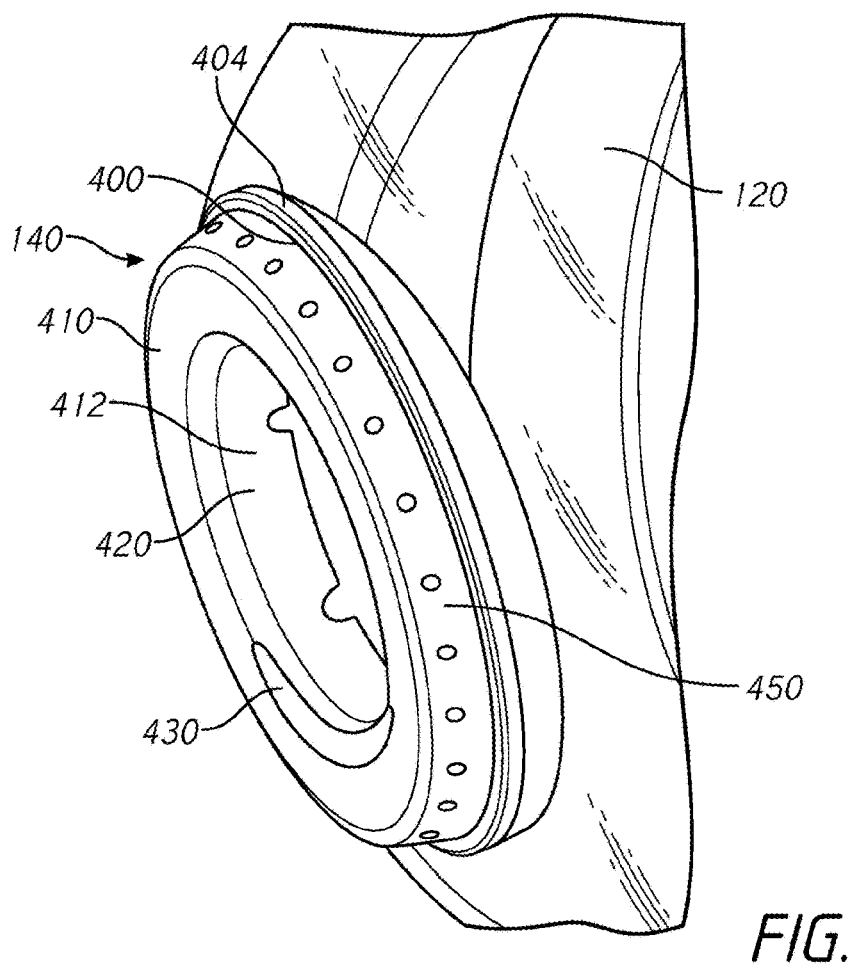
Figure 4E:
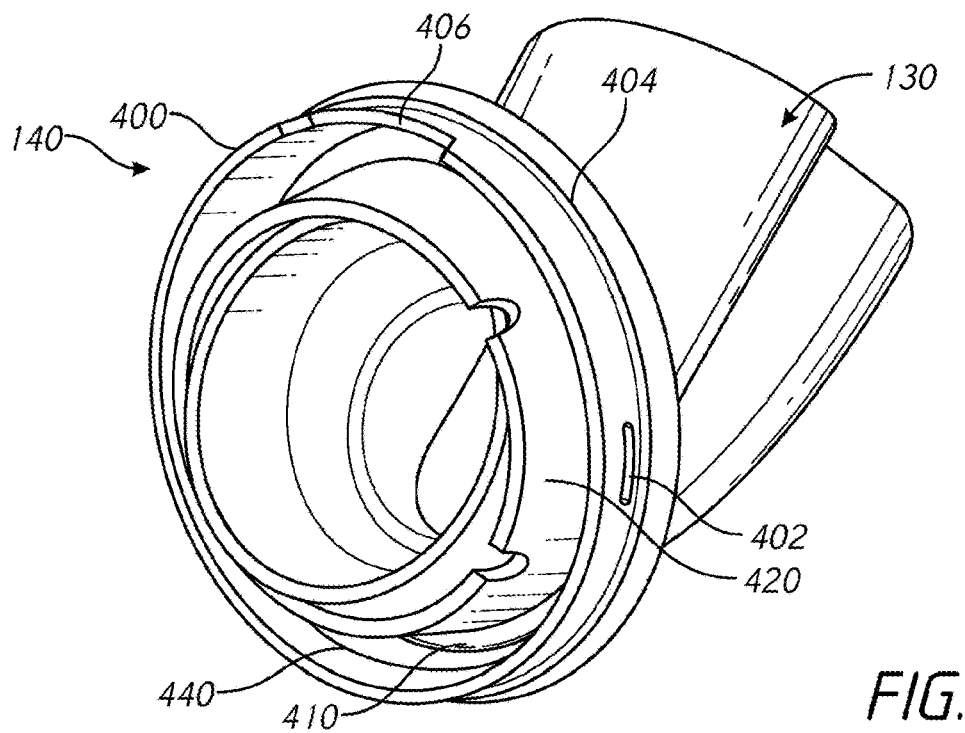

Elbow:

FIG. 3a shows a prior elbow 130, which comprises a ball joint 300, a lip 310, an elbow body 320 and a swivel connection 330. The ball joint 300 comprises a spherical elbow bearing surface 302 and a rear opening edge 304. In an alternative embodiment, as shown in FIG. 3b, the ball joint 300a can also comprise a tapered chamfer 306. The tapered chamfer 306 is positioned on a lower portion of the rear opening edge 304. The ball joint 300a is configured to provide a substantially freely rotating connection between the elbow 130 and the socket insert 140. The ball joint 300a is connected to the elbow body 320 via a cylindrical cuff 308 and the lip 310. The lip 310 comprises an edge that is formed by a surface that extends perpendicularly from the cylindrical cuff 308 and the geometry of the elbow body 320 and the lips 310 is generally at an upper portion of the elbow body 320. The lip 310 is configured to interact with the socket insert 140 during removal of the elbow 130 (see e.g., FIG. 5). The swivel connection 330 is positioned at the opposite end of the elbow 130 relative to the ball joint 300a. It is configured to connect to the swivel 160 (as shown in FIG. 1a).

Socket Insert:

FIGS. 4a to 4e show the socket insert 140 in more detail. The socket insert is an annular component that comprises an outer wall 400, a front wall 410, an inner wall 420, an elbow removal notch 430, a rear channel 440 and an annular array of bias-flow holes 450 (see e.g., FIG. 4d). The bias-flow holes 450 may comprise any suitable cross-sectional geometry, including but not limited to, circular or elliptical holes or slots, or slots comprising polygonal, chevron, 'U' and 'W' shapes, wherein the geometry may be symmetrical or asymmetrical. In other embodiments, the socket insert may not include the bias-flow holes 450. The bias flow holes 450 may be incorporated in another component of the respiratory mask.

The socket insert 140 provides a socket bearing surface 412 that receives the ball joint 300a is inserted. This configuration provides a rotatable connection between the elbow 130 and the mask frame 120. The outer wall 400, the front wall 410 and the inner wall 420 are connected to form a substantially 'u' shaped rear channel 440, wherein the front wall 410 is substantially perpendicular to the outer wall 400 and the inner wall 420. The front wall 410 is configured to connect and support the outer wall 400 at a radial offset from the inner wall 420.

The outer wall 400 comprises one or more seal housing notches 402, a frame connection 404, and an alignment key 406. The seal housing notches 402 are configured to provide a snap fit connection between the socket insert 140 and the seal housing 190. The seal housing notches 402 comprise an indentation that forms the female component of the snap fit connection. The frame connection 404 comprises two annular ridges that form a permanent push fit connection with the corresponding geometry of the socket connection opening 200 (as shown in FIG. 2a). The alignment key 406 is located on the upper rear edge of the outer wall 400. It comprises a substantially trapezoidal cut-out that aligns with a corresponding tab on the annular opening 194 of the seal housing 190. The alignment key is configured to reduce or eliminate the likelihood of a misaligned connection between the seal housing 190 and the socket insert 140. In some embodiments, the permanent connection between the frame connection 404 and the socket connection opening 200 may be achieved via ultrasonic welding or other suitable methods.

The inner wall 420 comprises a socket bearing surface 412, wherein the socket bearing surface 412 is substantially spherical and configured to contact and retain the ball joint 300a of the elbow 130. The socket bearing surface 412 is configured to contact the elbow bearing surface 302, thereby forming a substantially airtight assembly. When the elbow 130 and the socket insert 140 are connected, the bearing surfaces 302, 412 are configured to allow rotational movement between the parts, whilst restricting translational movement between the front and rear of the mask.

Figure 5:
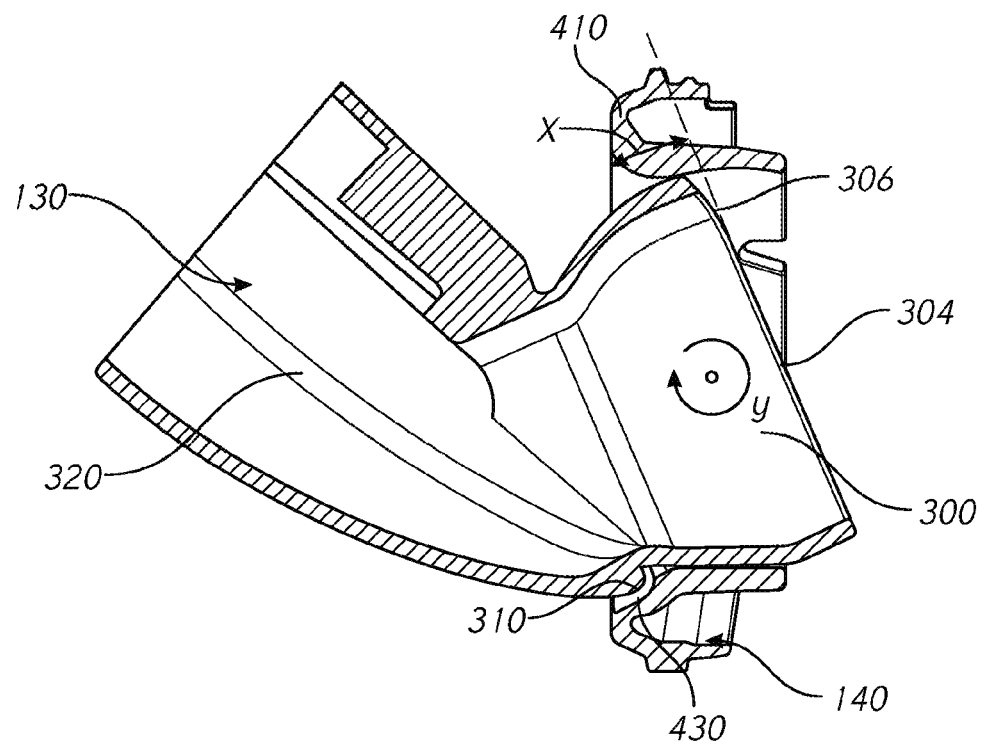
FIG. 5 is a cross-sectional view of the elbow and socket insert that shows the geometry that allows the elbow to be removed.

The elbow removal notch 430 is positioned on a lower portion of the edge that is formed where the front wall 410 and the inner wall 420 intersect. The removal notch 430 comprises a scalloped portion, wherein the edge is cut away to form a tapered concave surface. The elbow removal notch is configured to substantially match the geometry of the lip 310 of the elbow 130 such that, when the elbow 130 is rotated to an upside down position, the lip 310 can sit within the elbow removal notch 430, as shown in FIG. 5. It is this configuration that allows the elbow 130 to be removed from the socket insert 140. In other embodiments, the elbow removal notch 430 may have a geometry that differs from the lip 310 geometry such that the two components can come into contact.

When the elbow 130 is rotated to an approximately inverted position, the lip 310 is approximately aligned with the removal notch 430. When the lip 310 is positioned in the elbow removal notch 430, the ball joint 300 is able to rotate further within the socket insert 140. This is a result of the surface of the elbow removal notch being offset from the front wall. The extra rotation allows the lowest point (when mask is in use) of the rear opening edge 304 or tapered chamfer 306 to move closer to the front wall 410 (as shown by dimension x in FIG. 5). This reduced distance, x, to the front wall reduces the force required to move the rear opening edge 304 or tapered chamfer 306 beyond the front wall. The elbow removal notch 430 also forms a leverage point. The leverage point is formed by moving the ball joint's 300 center of rotation from the location y (as shown in FIG. 5) to the point of contact between the lip 310 and the elbow removal notch 430. The geometry of the elbow removal notch allows a force to be applied through the lip 310 and new center of rotation, thus forming the leverage point. The leverage point is further away from the lowest point of the tapered chamfer 306 than the center of rotation y; this reduces the force required to move the rear opening edge 304 beyond the front wall 410.

Once at least a portion of the rear opening edge 304 is beyond the front wall 410, the ball joint 300 can be removed from the socket insert 140. It can be seen that the purpose of the tapered chamfer 306 is to further reduce the distance x that the ball joint 300 needs to be rotated in order to move the rear opening edge 304 beyond the front wall 410 and, thus, be removed from the socket insert 140. In alternative embodiments (not shown), the elbow removal notch 430 may be replaced by a chamfered or scalloped section on the edge formed between the inner wall 420 and the front wall 410 of the socket insert 140. The chamfered edge can have the effect of reducing the distance x that the ball joint needs to rotate in order to be removed from the insert socket. In yet another alternative embodiment, the geometry of the elbow removal notch 430 may extend beyond the socket insert 140 and into the mask frame 120.

The elbow 130 and the socket insert 140 are generally configured such that the elbow 130 can only be removed from the socket insert 140 when oriented to a predetermined position. As shown in FIG. 5, in the present embodiment the elbow can be removed when it is rotated to an upside down position, where the elbow body 320 is directed upwards towards the bridge portion 220 of the mask frame 120 (not shown). This reduces or eliminates the likelihood of unintentional detachment of the elbow during use. In other embodiments, the elbow 130 may be rotated to a different position for removal. Once removed, the elbow 130 can be reassembled to the socket insert 140 by reversing the removal actions and forces.

The single removal position and blended geometry of the elbow removal notch 430 dictate that the action of removing the elbow may not be obvious to all users, meaning that a user may need to be taught how to remove the elbow. This may be beneficial in some situations, as it may be desirable for only certain user groups to know how to remove the elbow. For instance, removal of the elbow for cleaning and sterilization is particularly important in environments where a single mask may be used for multiple users, such as in sleep labs; whereas it is not as important in home use environments where the mask has only a single user. Therefore, it may be desirable for doctors or sleep lab technicians to know how to remove the elbow, but not the direct user of the mask. In alternative embodiments, the geometry may be such that it is obvious how to remove the elbow.

Figure 6A:
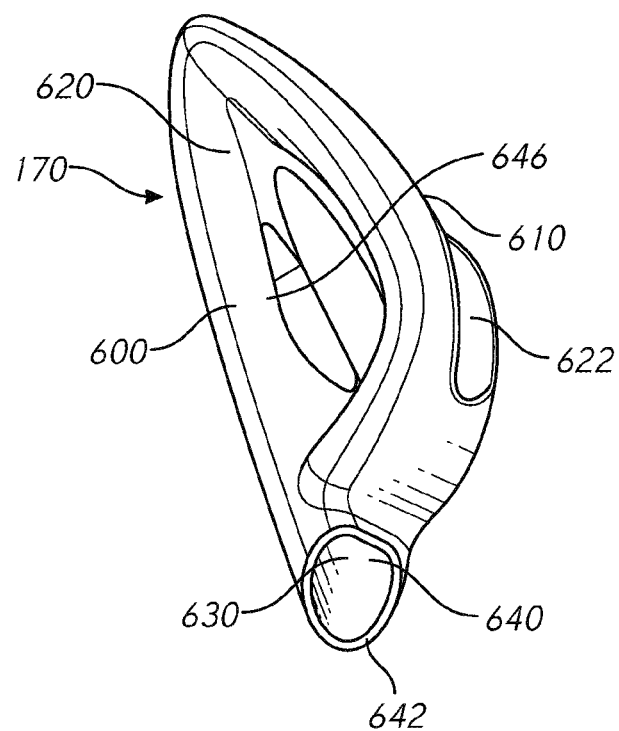
FIGS. 6a to 6e show various views of the forehead piece of the present disclosure.
Figure 6B:
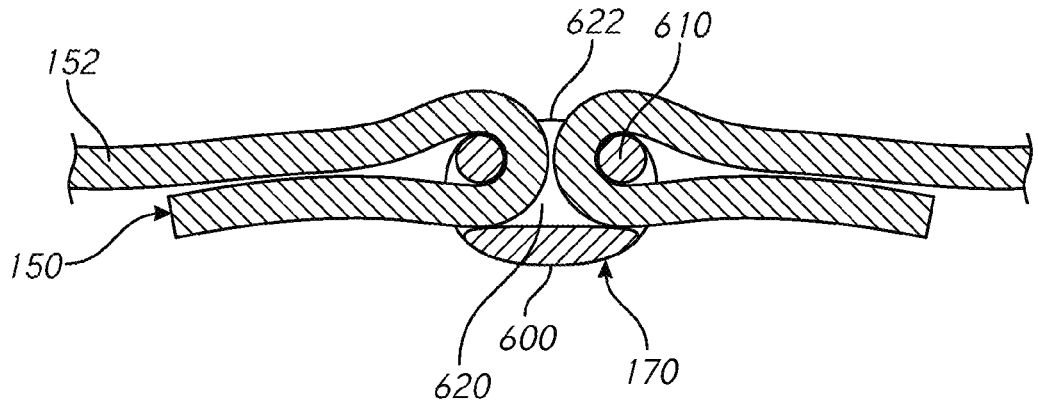
Figure 6C:
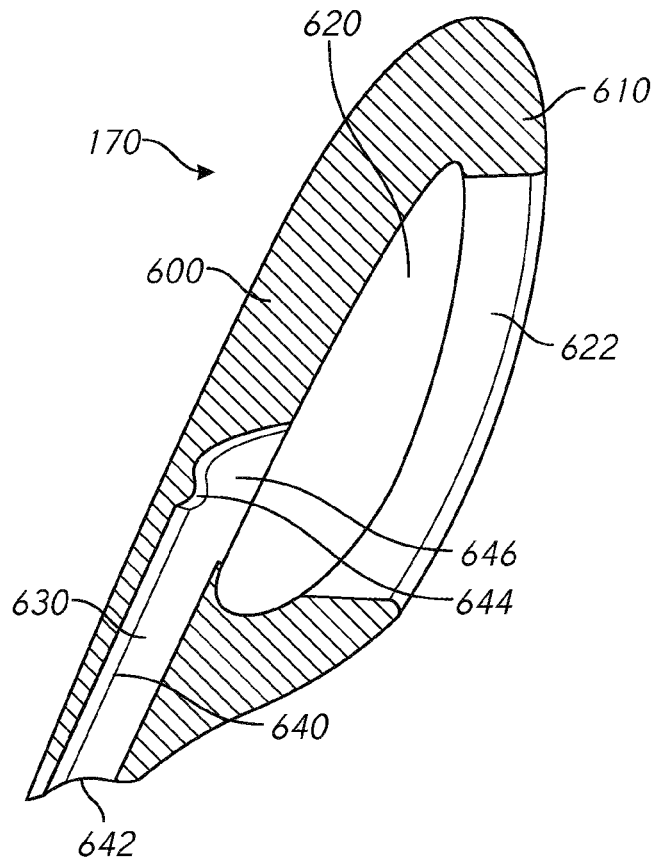

Forehead Piece:

As shown in FIG. 1a, the forehead piece 170 is a removable end cap configured to provide a connection between the mask frame 120 and the headgear 150. FIGS. 6a to 6e show that the forehead piece 170 comprises a front portion 600 and a rear portion 610, wherein the front and rear portions 600, 610 are connected to form a horizontal loop 620. The horizontal loop 620 provides a hole that extends horizontally (when the mask is in use) from one side of the forehead piece 170 to the other. The rear portion 610 comprises a rear opening 622. The rear opening 622 is configured to extend through the rear portion 610 in a direction that is substantially perpendicular to the front portion 600. The rear opening 610 in combination with the horizontal loop 620 are configured to provide a path through which the forehead straps 152 of the headgear 150 can pass. Both of the forehead straps 152 enter the forehead piece through the rear opening 622 and one forehead strap 152 exits from each side of the horizontal loop 620, as shown in FIG. 6b. In this configuration, the forehead piece forms a buckle through which the length of the forehead straps 152 can be adjusted.

Figure 6D:
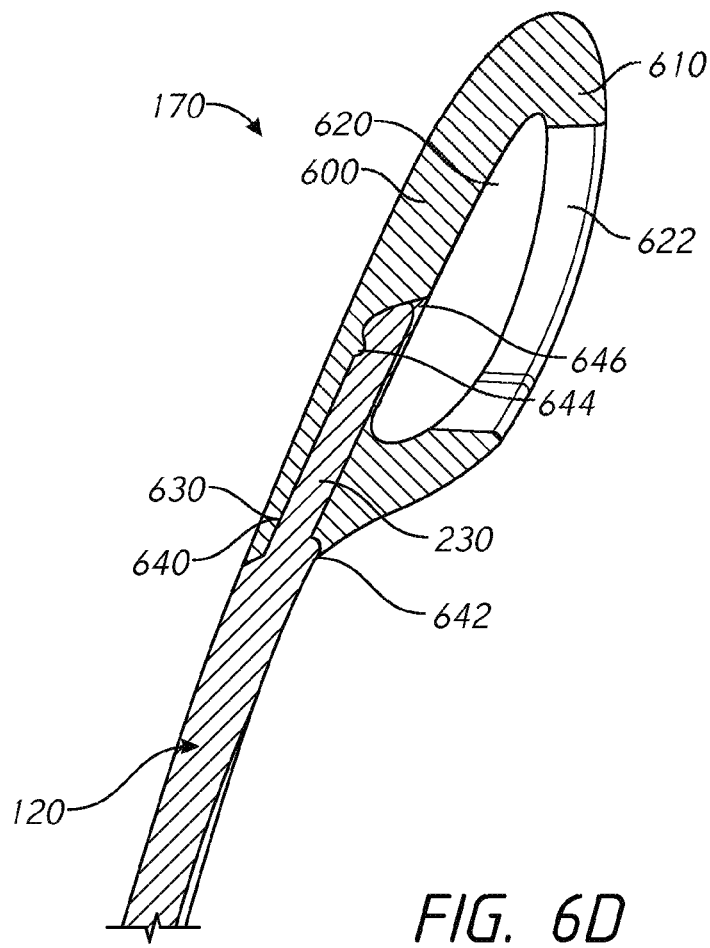

The front portion 600 comprises a female frame connector 630. The female frame connector 630 is configured to connect to the male forehead piece connector 230 of the mask frame 120 and comprises an internal cavity 640. The internal cavity 640 is shown in more detail in FIG. 6c. The internal cavity comprises a frame opening 642, a bump 644 and a moulding opening 646. The frame opening 642 is configured to pass over the male forehead piece connector 230. As shown in FIG. 6d, the geometry of the internal cavity 640 is configured to substantially match the geometry of the male forehead piece connector 230. The bump 644 comprises a raised lump that is configured to fit into the notch 234 of the male forehead piece connector 230. When the bump 644 and notch 234 are fitted together they, form a snap fit connection that enables the forehead piece 170 to be removably connected to the mask frame 120. The moulding opening 646 provides the internal cavity 640 with a second opening at the opposing end to the frame opening 642. The opening is substantially perpendicular to the front portion 600 and is located on the rear surface of the front portion. The moulding opening 646 is configured to provide a means for the mould tool to form the bump 644 on an internal surface of the internal cavity 640. The moulding opening 646 is configured to fit within the bounds of the rear opening 622, such that a single tooling component may form both the moulding opening 646 and the bump 644 as well as the rear opening 622.

Figure 6E:
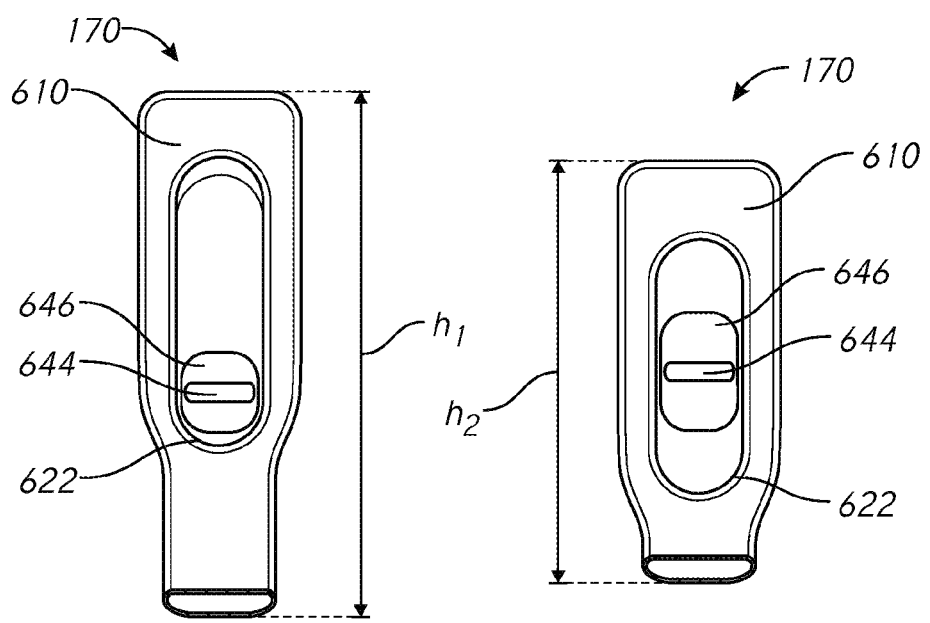

The forehead piece 170 is provided in two or more sizes, as shown in FIG. 6e. The different sizes can be provided by varying the height h of the forehead piece 170. The different sizes cater to a range of facial geometries in users. In the present embodiment, a medium/large and a small size are provided, wherein the small size has a height $h_2$ that is less than the height $h_1$ of the medium/large. The height of the forehead piece 170 determines the height at which the forehead straps of the headgear are connected to the mask 100 and, thus, how far up a user's forehead the straps will sit. The size of the forehead piece 170 can be selected to provide the most comfortable fit for a user. The horizontal loop 620 varies in size dependent on the height h of the forehead piece 170. The rear opening 622 has a fixed size that corresponds to the width of the forehead straps 152. The fixed size of the rear opening 622 restricts vertical movement of the forehead straps within the horizontal loop.

In other configurations, the forehead piece 170 and the mask frame may be configured for a one time, permanent connection (e.g., a barbed or ramped protrusion and notch). Such a configuration allows for a common mask frame that is connectable to forehead pieces 70 of various shapes and sizes.

Figure 7A:
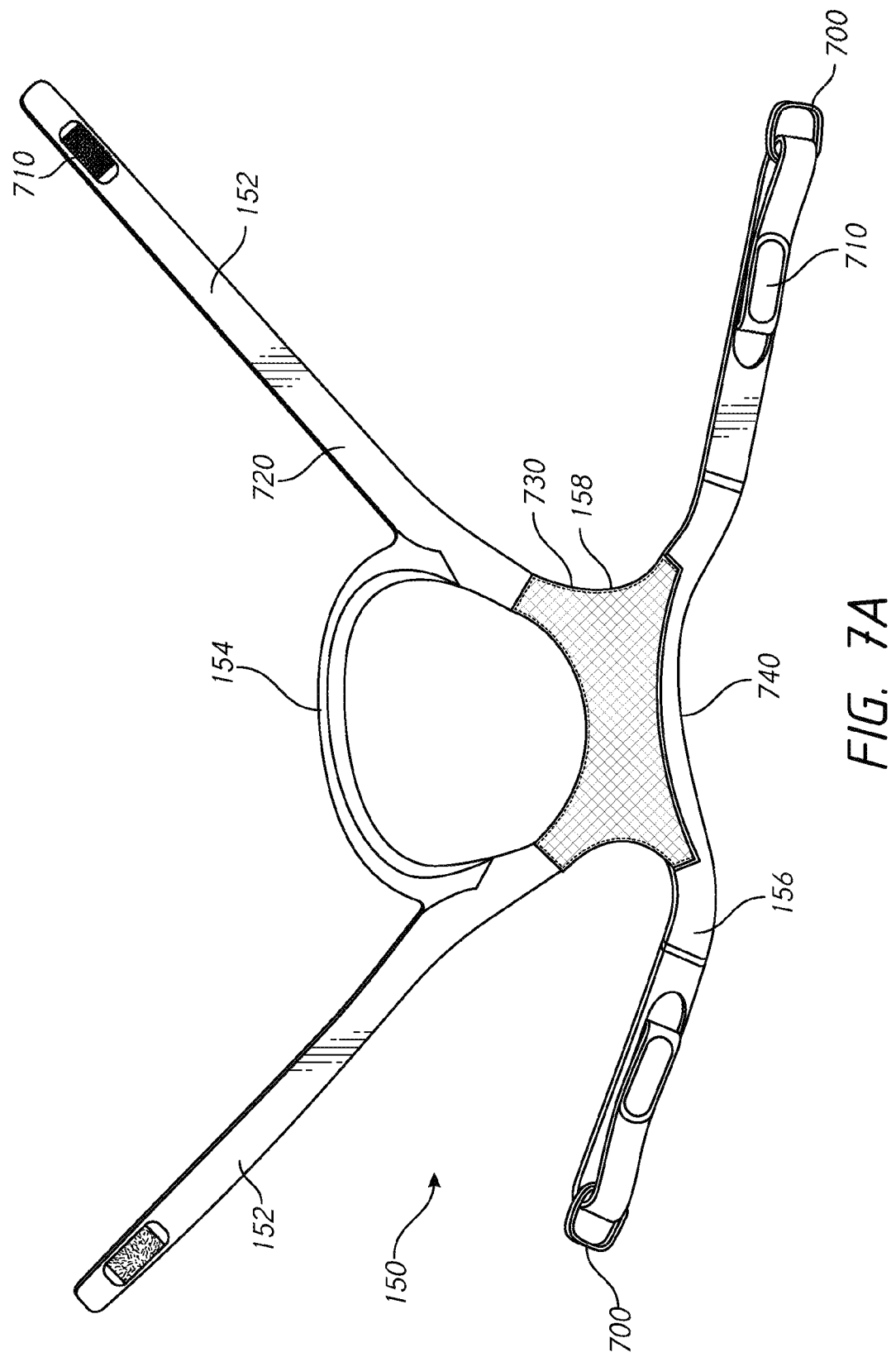
FIGS. 7a and 7b show various views of the headgear of the present disclosure.
Figure 7B:
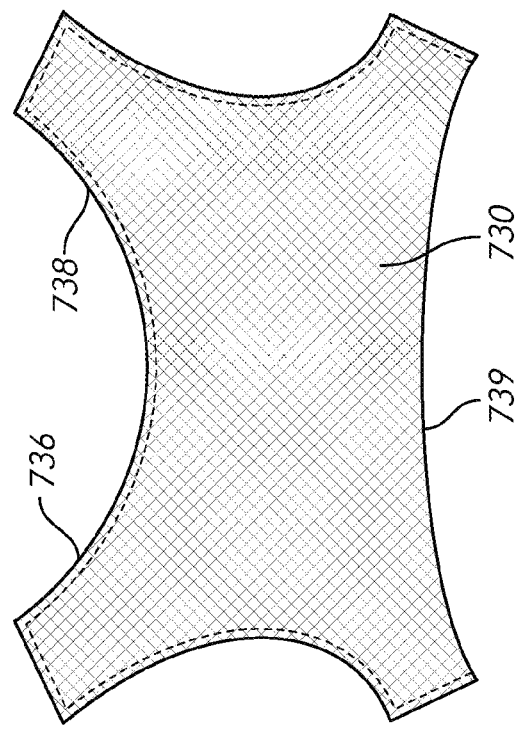
Figure 7B:
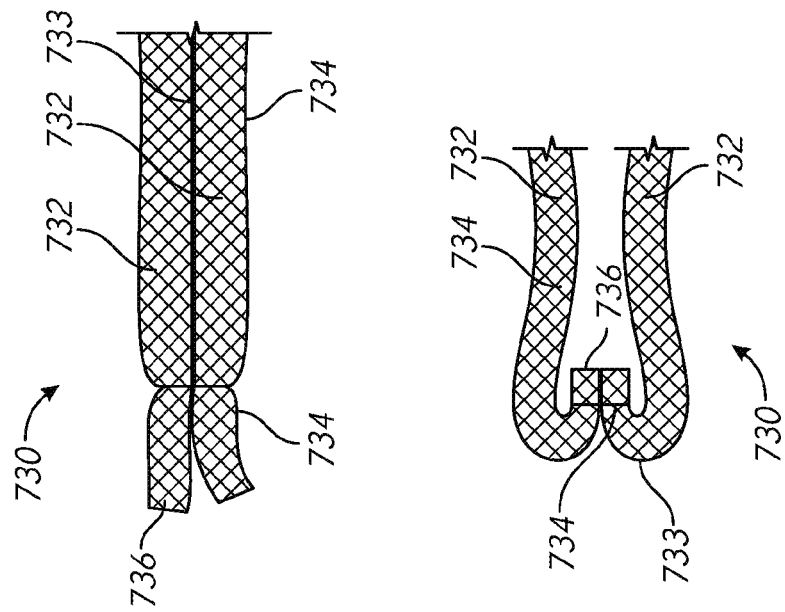

Headgear:

The headgear 150 is configured to apply retaining forces to the mask frame 120 such that the respiratory mask 100 is held in place on a user's face and a substantially airtight seal is achieved. The headgear 150 comprises a pair of forehead straps 152, a crown strap 154, a pair of chin straps 156 and a rear headgear portion 158, as shown in FIG. 7. In use, the forehead straps 152 are configured to extend forward from the rear headgear portion 158 and across the user's forehead to connect to the forehead piece 170, as previously described. The crown strap 154 is configured to form a link between the forehead straps, wherein the crown strap extends across the top of the user's head. The chin straps 156 are configured to extend forward from the lower edge of the rear headgear portion 158, across the user's cheeks and chin, to the headgear connectors 210 of the mask frame 120. The chin straps 156 are connected to the headgear connectors 210 via separate headgear clips 700. The headgear clips hook onto post components in the headgear connectors and provide a quick means for users to attach and detach the headgear 150 from the mask frame 120.

The length of the forehead straps 152 and chin straps 156 is secured by hook and loop fastener tabs 710 located at the ends of the straps. The tabs 710 comprise the hook component of hook and loop fastener material and are configured to the headgear outer surface 720. The outer surface 720 is configured to have a surface finish that is suitable for the hook material to attach to. The forehead straps 152, the crown strap 154 and the chin straps 156 are made from a material, such as Breath-o-prene™, which comprises layers of differing fabrics including textiles and foams. Breath-o-prene™ is made from polyurethane foam with an outer layer of nylon and spandex. The materials are heat laminated together. Each of the straps can be made from a material with differing physical properties. For example, the crown strap 154 can be stretchable while the chin straps 156 are substantially non-stretch by comparison.

The rear headgear portion 158 comprises a spacer fabric pad 730 and a lower back strap 740. The spacer fabric pad 730 comprises a substantially rectangular portion with scalloped edges and the corners cut off. The cut off corners are configured to attach to the forehead straps 152 and the lower back strap 740. FIG. 7b shows that the spacer fabric pad 730 comprises two spacer fabric layers 732 layered one on top of the other. The spacer fabric layers have a right side 733 and a wrong side 734. The two layers are sewn together, inside out (i.e., with the wrong sides of the fabric facing out) to form a seam 736 near the raw edges 738 of the spacer fabric layers. Once sewn together the layers 732 are then turned right-side out, such that the right sides 733 are on the outside and the raw edges 736 are on the inside. The seam 736 extends around the perimeter of the spacer fabric pad 730 leaving the bottom edge 739 open. The open bottom edge 739 allows the spacer fabric pad 730 to be turned right-side out. Once turned right-side out, the forehead straps 152 and lower back strap 740 are attached to the spacer fabric pad 730. In the present embodiment, they are sewn together; however, other attachment methods, such as but not limited to welding may be appropriate. The open bottom edge 739 is sealed at the same time as being attached to the lower back strap 740.

The present headgear configuration incorporates the spacer fabric pad 730 in order to provide a light weight, breathable and cushioned region at the rear of the user's head. These qualities are desirable as they may improve the user's comfort when wearing the headgear. Spacer fabric has an untidy edge finish that tends to fray when cut. The present configuration of the spacer fabric pad 730 provides a tidy edge finish by hiding the raw edges on the inside of the pad. The seam 736 may also help to reduce or eliminate the likelihood of fraying.

The lower back strap 740 extends along the bottom edge 739 of the spacer fabric pad. The lower back strap 740 is made of a material that is less stretchy than the spacer fabric pad 730. The lower back strap provides structural reinforcement to the spacer fabric pad 730 to reduce or eliminate the likelihood of excessive stretching that may cause the mask 100 to become displaced from a user's face during use.

Cushion Module:

As described above, the cushion module 110 is configured to substantially surround a user's nose and/or mouth and includes a seal 180 and a seal housing 190. The seal housing 190 provides a support structure of sorts for the respiratory mask assembly 100 in general and for the mask cushion or seal 180 more specifically. Although the respiratory mask 100 disclosed herein comprises a separable cushion module 110 and frame 120, in some configurations these components can be combined into a single structure. Accordingly, although described as a portion of the cushion module 110 herein, the seal 180 could also comprise a portion of a mask frame. Other suitable interface arrangements for defining a breathing chamber, supporting the seal and allowing connection of a breathing gases conduit and headgear (if desired) can also be used.

Figure 8:
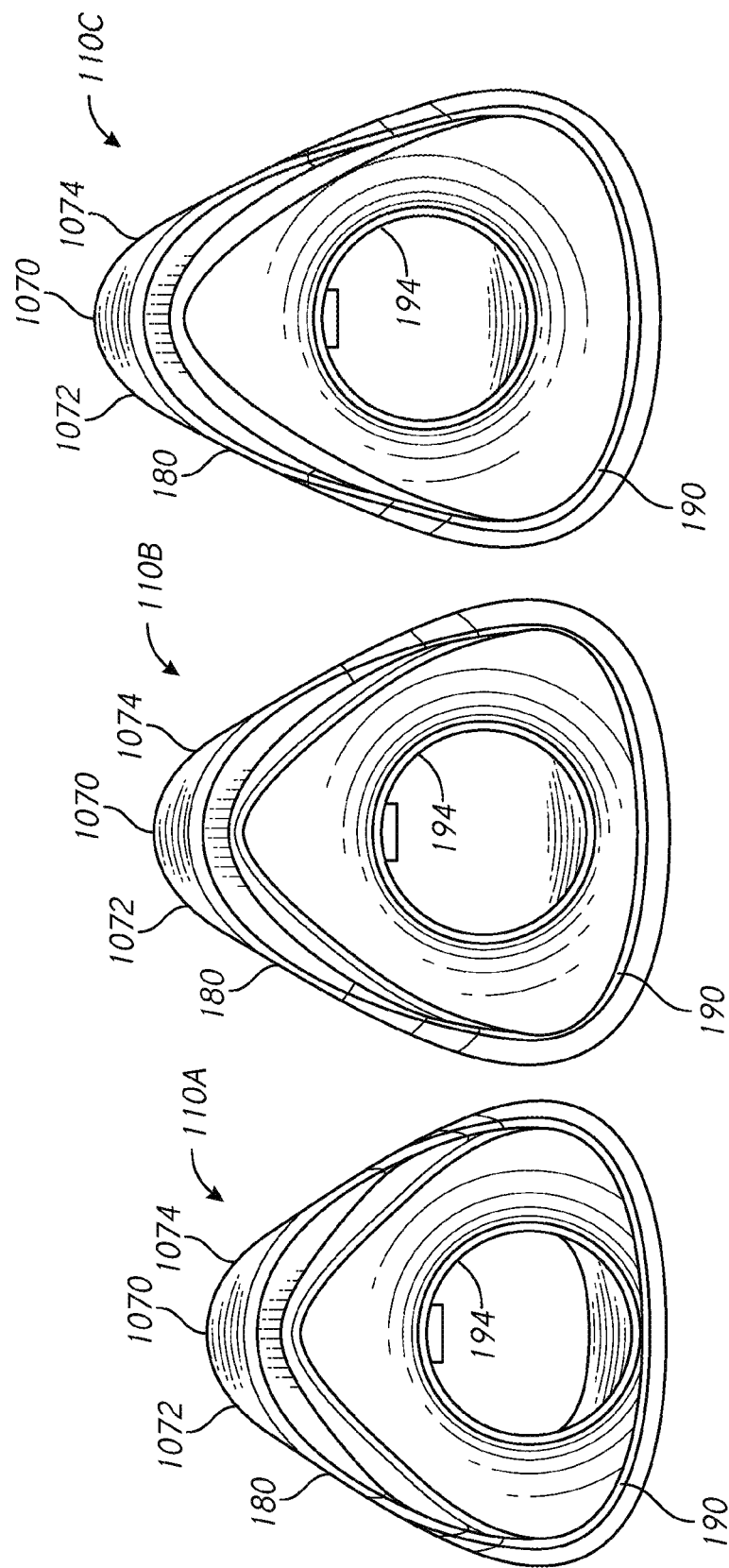
FIG. 8 illustrates front views of several cushion modules of different sizes.
Figure 9:
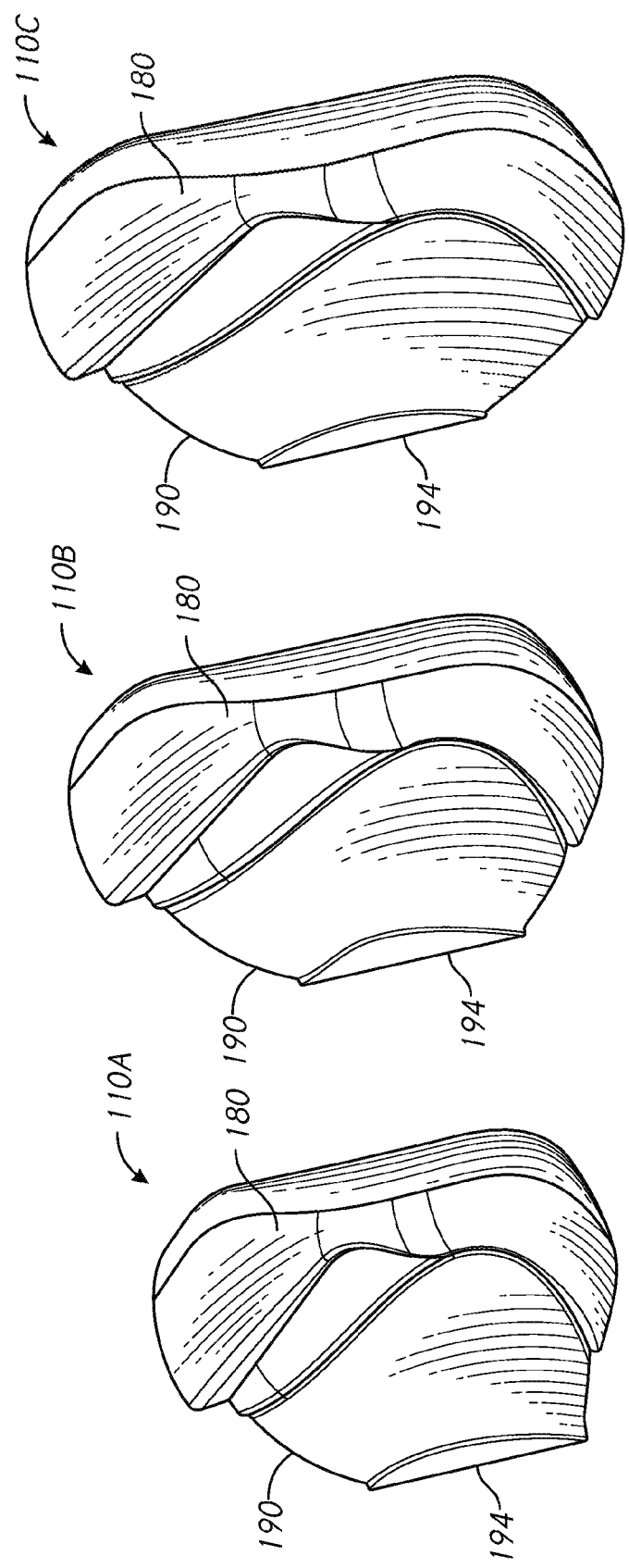
FIG. 9 illustrates side views of the cushion modules of FIG. 8.

In some configurations, multiple cushion modules 110 are available for a given respiratory mask 100. For example, cushion modules 110 can vary from one another in size such that a suitable one of the available cushion modules 110 can be selected for a particular user. However, cushion modules 110 could vary relative to one another with respect to characteristics other than size in addition or in the alternative. FIGS. 8 and 9 illustrate a plurality of differently-sized cushion modules 110 that can be used as a component of the respiratory mask 100 disclosed herein. Each cushion module 110 is of substantially the same construction, with the exception of certain dimensions, some of which are discussed herein.

Cushion module 110a is relatively smaller in at least one dimension (e.g., seal height) than cushion modules 110b and 110c. Similarly, cushion module 110b is relatively smaller in at least one dimension (e.g., seal height) than cushion module 110c. Cushion modules 110a, 110b and 110c can be referred to as a size "small," "medium," and "large" modules, respectively. In some configurations, additional modules 110 can be provided, which can fall on either end of the illustrated modules 110a, 110b, 110c or could have at least one dimension that places the additional module(s) between the illustrated modules 110a, 110b, 110c in a relative sense. In some configurations, a lesser number (e.g., two) of cushion modules 110 are provided. As described herein, a reference to a general cushion module 110 can apply to any of the particular modules 110a, 110b, 110c. When discussing the modules 110a, 110b, 110c relative to one another, the specific reference numbers 110a, 110b, 110c generally are used. One or both of the seal 180 and the seal housing 190 can vary between the various size modules 110a, 110b, 110c. In the illustrated arrangement, both the seal 180 and the seal housing 190 vary in size between the various size modules 110a, 110b, 110c.

The seal housing 190 can be formed from any suitable material. In some configurations, the seal housing 190 is formed from a fairly rigid material. In some configurations, the seal housing 190 is formed from a plastic material, such as a polycarbonate material. In some configurations, the seal 180 is overmolded onto the seal housing 190 and, in some configurations, the seal 180 can be overmolded directly onto the seal housing 190, which can comprise chemical or mechanical overmolding, for example.

In some configurations, the seal housing 190 comprises a substantial portion of a forward wall of the cushion module 110. Such an arrangement provides an advantageous amount of support to the seal 180. For example, the seal housing 190 comprises a substantial portion of an oral portion of the forward wall of the cushion module 110. In the illustrated configuration, the seal housing 190 sweeps rearward from a central portion toward opposing side portions. The central portion contains the aperture or opening 194 for allowing a flow of supplied breathing gases to enter an interior of the cushion module 110. The opening 194 can allow the cushion module 110 to be assembled to the frame 120, the mask elbow 130 or another suitable structure. A width of the seal housing 190 can comprise a significant portion of the overall width of the oral portion of the cushion module 110, such as at least about three-quarters of the overall width of the oral portion of the mask assembly 100. Such an arrangement of the seal housing 190 can provide a desired amount of support to lateral portions of the seal 180. In some configurations, the seal housing 190 could be minimal, such as an annular support ring or frame, for example.

The seal 180 is designed to seal against the face of the user. The seal 180 preferably is formed of a soft material, such as silicone, for example but without limitation. In some configurations, at least portions of the seal 180 can be textured to improve comfort to the user. For example, in some configurations, at least portions of the mold used to form the illustrated seal 180 can be bead blasted to provide a surface texture in at least the regions of the seal 180 that will contact the skin of the user. Other techniques for texturing one or more surface of the seal 180 can be used. In some configurations, it may be desirable to avoid surface texturing and provide at least the face-contacting surfaces of the seal 180 with a smooth surface texture, which may increase grip of the seal 180 on the user's face and improve sealing characteristics.

As described above, the illustrated cushion module 110 comprises a nasal-oral or full face mask. Accordingly, with reference to FIGS. 10-15, the seal 180 comprises a nasal-oral mask seal and, therefore, comprises a combined oral-nasal opening 1000. In other configurations, the oral portion and nasal portion of the opening 1000 can be separate from one another. The opening 1000 preferably communicates with the breathing chamber 192 that is defined within the cushion module 110. As described above, the chamber 192 of the illustrated mask assembly 100 is at least partially defined by the seal housing 190 and the seal 180.

The illustrated seal 180 includes an upper portion 1002 and a lower portion 1004. The upper portion 1002 comprises a nasal portion of the opening 1000 that accommodates the user's nose. The lower portion 1004 comprises an oral portion of the opening 1000 that accommodates the user's mouth. Thus, the lower portion 1004 is significantly wider than the upper portion 1002. Together, on a proximal side of the cushion module 110, the upper portion 1002 and the lower portion 1004 combine to define a portion or an entirety of a face contacting surface 106. The face contacting surface 106 is configured to underlie a lower lip of the user, extend along the outside of the mouth, extend upward along the cheekbones and extend across the bridge of the nose of the user. Thus, the illustrated face contacting surface 106 defines a generally tear-drop shaped opening 1000. When the cushion module 110 is seated on the face of the user, the face contacting surface 106 will lie over the bridge of the nose, the cheekbones, the outside of the mouth and below the lower lip of the user. With a supply of positive pressure air, the seal 180 will balloon and seal against the face of the user to reduce or eliminate the likelihood of leakage between the face contacting surface 106 and the face of the user.

The illustrated seal 180 is a full face seal that is configured for similar applications and/or user preferences as the respiratory mask sold by the Applicant, Fisher & Paykel Healthcare, under the trademark Simplus®. While the Simplus® mask is a very successful full face respiratory mask product that provides excellent sealing characteristics and comfort for a wide variety of facial geometries, the illustrated seal 180 includes features or modifications relative to the Simplus® mask that provide improved performance for at least some applications or facial geometries. Thus, certain features of the present seal 180 are described in relation to the seal of the Simplus® mask.

Figure 11:
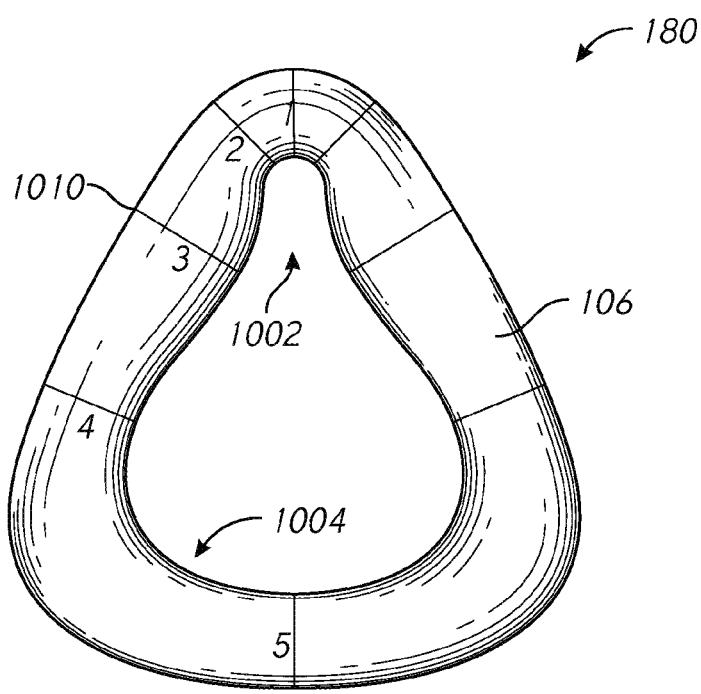
FIG. 11 is a plan view of the seal showing several sections.

With reference to FIG. 11, a plan view of the seal 180 illustrates width dimensions between an outer edge 1010 of the seal 180 and an inner edge that defines the opening 1000 along several sections of the seal 180, indicated as sections 1-5. At least sections 2-3 preferably are identical on each side of the seal 180. In some configurations, sections 2-4 can be identical on each side of the seal 180. Thus, in some configurations, the seal 180 can be symmetric about a central, vertical axis. Section 1 is a vertical line at the center top of the seal 180, which is coincident to the center line or lies within the mid-plane of the seal 180. Section 2 is a line that is 45 degrees to a vertical center line or mid-plane of the seal 180 and 90 degrees to the inner edge 1000 of the seal 180. Section 3 is a line at the widest part of the upper portion 1002 of the seal 180, which can be the widest part of the entire seal 180 in some configurations, which is 90 degrees to the outer edge 1010 of the seal 180. Section 4 is the narrowest section of a lateral side of the lower portion 1004 of the seal 180 below Section 3 and that is 90 degrees to the outer edge 1010 of the seal 180. Section 5 is a vertical line at the center bottom of the seal 180. The table (Table 1) below lists exemplary dimensions of the sections for several sizes of the seal 180 in comparison with corresponding locations and sizes of the Simplus® seal. The listed dimensions for the seal 180 are exemplary dimensions and are not intended to be limiting unless otherwise indicated. In addition, the actual dimensions can vary within a range determined by normal manufacturing variations, which may be indicated herein by use of the terms "about," "approximately," or other similar terms. The dimensions illustrate widths of the various sections relative to one another and relative to the Simplus® seal.

TABLE 1

| | Section 1 | Section 2 | Section 3 | Section 4 | Section 5 |
|---|---|---|---|---|---|
| Seal 180 Small | 15.1 mm | 15.2 mm | 20.9 mm | 17.5 mm | 15.8 mm |
| Simplus Small | 12.5 mm | 12.2 mm | 19.5 mm | 17.8 mm | 16.0 mm |
| Seal 180 Medium | 15.1 mm | 14.9 mm | 20.8 mm | 17.1 mm | 16.1 mm |
| Simplus Medium | 12.5 mm | 12.2 mm | 19.3 mm | 17.3 mm | 16.1 mm |
| Seal 180 Large | 15.1 mm | 14.7 mm | 20.9 mm | 17.3 mm | 16.8 mm |
| Simplus Large | 12.5 mm | 12.2 mm | 19.3 mm | 17.3 mm | 16.8 mm |

In general, Table 1 illustrates that, in the seal 180, sections 1 and 2 are relatively close in width. In some configurations, sections 1 and 2 can have the same width. Section 3 is larger than one or both of sections 1 and 2. In some configurations, sections 1 and 2 can be about 75% of the width of section 3. In some configurations, sections 1 and 2 are at least 70% of the width of section 3. Seal 180 has less variation in width in the upper portion 1002 or at least at sections 1, 2 and 3 relative to the Simplus® seal. In some configurations, as described below, sections 1 and 2 of the seal 180 have a larger width than comparable sections of the Simplus® seal, while section 3 of the seal 180 and the comparable section of the Simplus® seal are relatively similar in width.

One or both of sections 4 and 5 of the seal 180 have a width that is less than a width of one or more of sections 1-3. In the illustrated arrangement, both of sections 4 and 5 have a width that is less than a width of section 3. One or both of sections 4 and 5 of the seal 180 can have a width that is less than a width of one or more of sections 1-3. In the illustrated arrangement, both of sections 4 and 5 have a width that is greater than both of the widths of sections 1 and 2. The width of section 5 in the illustrated configuration is slightly greater, but similar to, the width of sections 1 and 2. The widths of sections 4 and 5 of the seal 180 are relatively similar to the widths at comparable locations of the Simplus® seal. In some cases, the widths of one or both of sections 4 and 5 are identical (e.g., size large) between the seal 180 and the Simplus® seal or the widths of seal 180 are slightly less than the widths of comparable sections of the Simplus® seal (e.g., size small). In size medium, the width of section 5 is identical, while the width of the seal 180 is slightly less than the width of the Simplus® seal at section 4.

Figure 12:
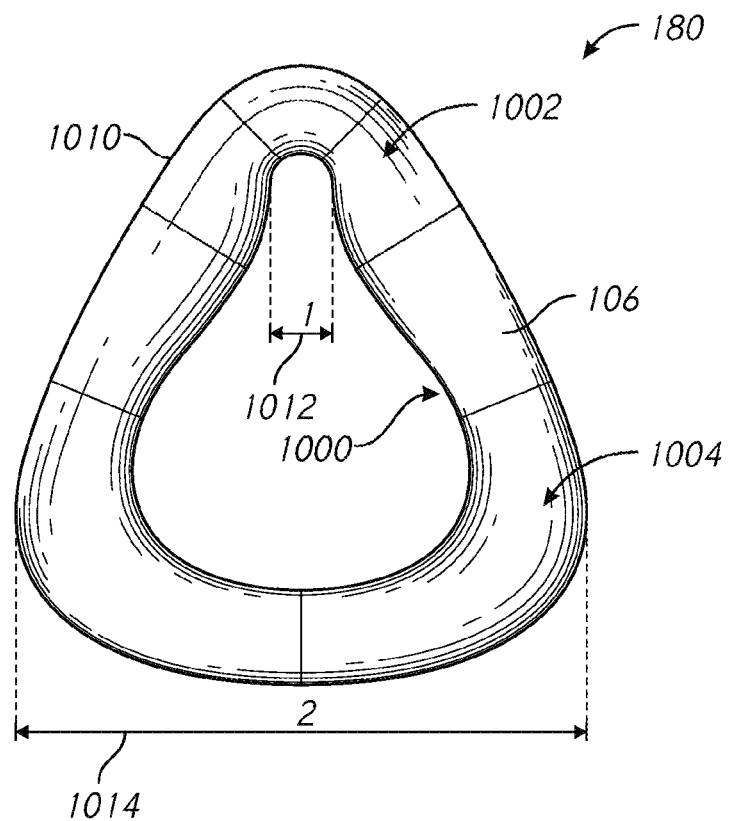
FIG. 12 is a plan view of the seal showing widths of two portions of the seal.

With reference to FIG. 12, a plan view of the seal 180 illustrates a first width 1012 of the opening 1000 defined between laterally opposite locations located on the opening 1000 within an upper portion 1002 of the seal 180 and a second width 1014 between laterally opposite locations located on the outer edge 1010 of the seal 180 within a lower portion 1004 of the seal 180. In particular, the illustrated first width 1012 is the width of the upper end portion of the opening 1000 within the upper portion 1002 of the seal 180 that accommodates the bridge of the user's nose. The width 1012 can be defined between relatively vertical sidewall portions of the upper end of the opening 1000 or between laterally opposite points at or near a point of inflection or undulation point at which each side of the edge defining the opening 1000 transitions between inward and outward curvature within the upper central portion of the upper portion 1002 of the seal 180. The width 1012 can be a width that contacts the bridge of the user's nose or determines or influences fit with the bridge of the user's nose. The width 1014 can be the maximum width of the face-contacting surface 106 within the lower portion 1004 of the seal 180, which can be the maximum width of the seal 180 in common seal arrangements. The width 1012 preferably is relatively small at least compared to the width 1014, which is useful as a reference point to compare the width 1012 relative to other seals. The table (Table 2) below lists exemplary dimensions of the widths 1012 and 1014 for several sizes of the seal 180 in comparison with corresponding locations and sizes of the Simplus® seal. The listed dimensions for the seal 180 are exemplary dimensions and are not intended to be limiting unless otherwise indicated. In addition, the actual dimensions can vary within a range determined by normal manufacturing variations, which may be indicated herein by use of the terms "about," "approximately," or other similar terms.

TABLE 2

| Seal | Width 1012 | Width 1014 | Ratio |
| --- | --- | --- | --- |
| Seal 180 Small | 11 mm | 95.7 mm | 0.1149 |
| Seal 180 Medium | 11 mm | 96.5 mm | 0.1140 |
| Seal 180 Large | 11 mm | 97.3 mm | 0.1131 |
| Simplus Small | 12.5 mm | 96.1 mm | 0.1301 |
| Simplus Medium | 12.5 mm | 96.5 mm | 0.1295 |
| Simplus Large | 12.5 mm | 96.9 mm | 0.1290 |

Table 2 illustrates that the width 1012 is less than about 12.5 percent, 12 percent or 11.5 percent of the width 1014 in all sizes of the seal 180. In some configurations, the width 1012 can be equal to about 12.5 percent or equal to about 12 percent of the width 1014 in one or more sizes of the seal 180. The width 1012 of the illustrated seal 180 can be equal to about 11.5 percent of the width 1014. The width 1012 of the illustrated seal 180 can be between about 11.3-11.5 percent of the width 1014 for one or more sizes of the seal 180. The absolute value of the width 1012 can be equal to or less than about 12 mm, equal to or less than about 11.5 mm or equal to or less than about 11 mm regardless of the width 1014. Such arrangements provide a desirable level of sealing for a variety of nasal sizes and geometries. In comparison, the widths of the Simplus® seal corresponding to width 1012 are 12.5 mm and about 12.9-13 percent of the width corresponding to width 1014.

Figure 10:
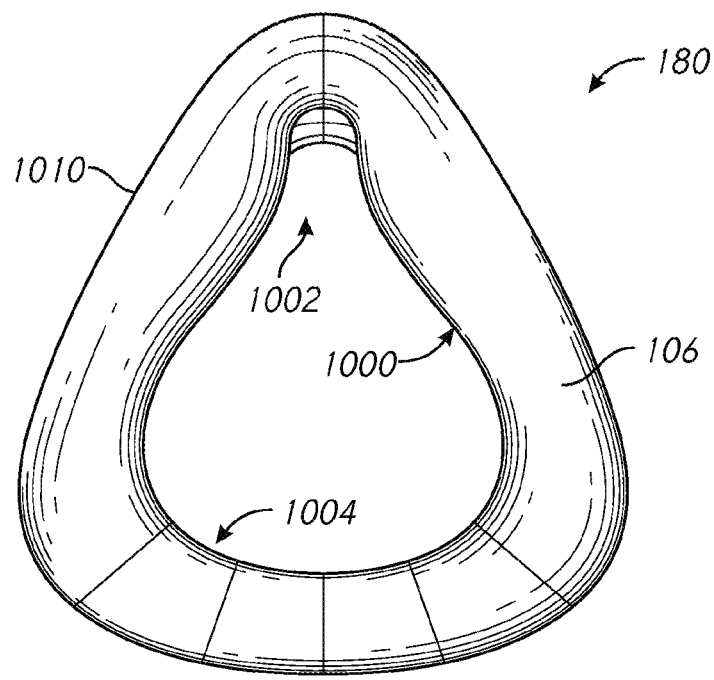
FIG. 10 is a plan view of a face contacting surface of a seal of one of the cushion modules of FIG. 8.
Figure 13:
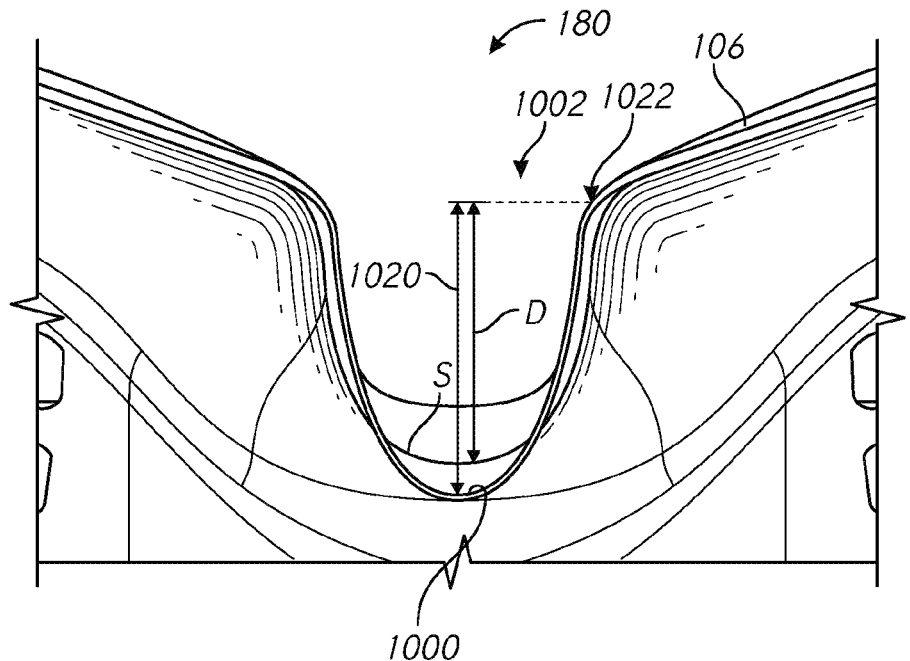
FIG. 13 is a bottom view of an upper portion of the seal and, in particular, a nose bridge portion.
Figure 14:
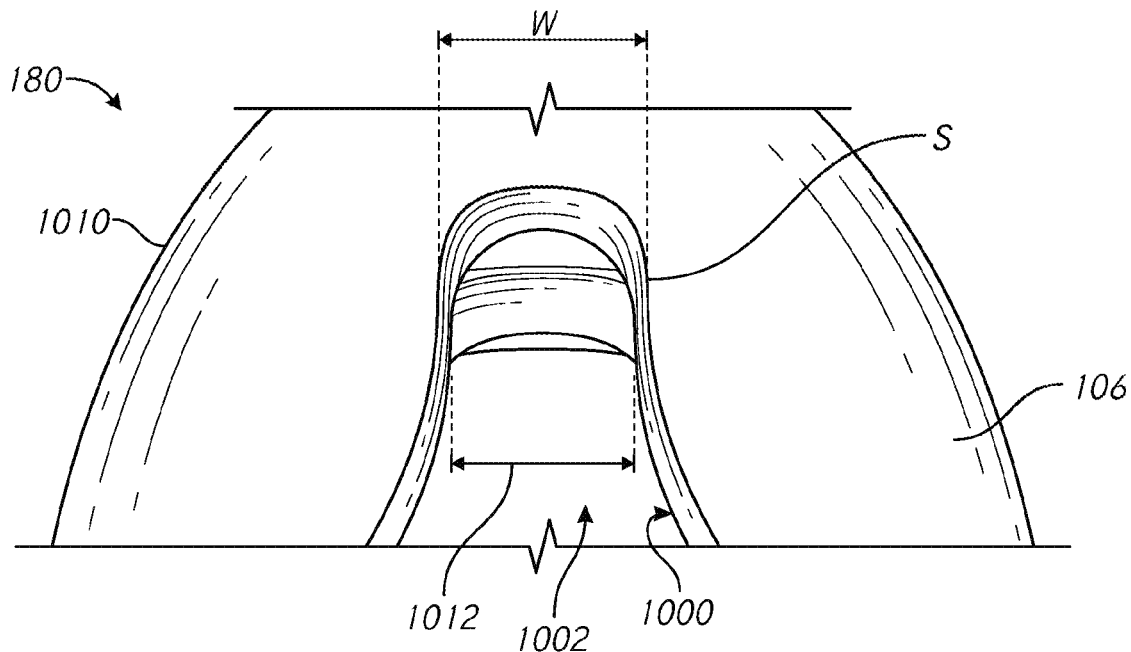
FIG. 14 is a view of the face contacting surface of the nose bridge portion of the seal.

With reference to FIGS. 10, 13 and 14, the upper portion 1002 of the opening 1000 of the illustrated seal 180 defines a substantially continuously curved, uppermost section at the center, top of the opening 1000. Preferably, the uppermost section of the opening 1000 defining the center, top of the opening 1000 does not include any linear portions or at least any linear portions of significant length relative to an overall length of an edge of the upper portion 1002 or relative to a width of the upper portion 1002. The rounded shape of the center, top of the opening 1000, which contacts the top of a user's nose, is believed to stretch to accommodate relatively square or sharp nasal geometries while also sealing well against smaller and/or rounder nasal geometries by reducing or eliminating gaps.

With reference to FIGS. 13 and 14, the seal 180 is illustrated with a corresponding edge S of the Simplus® seal included for the sake of comparison. As illustrated in FIG. 13, the seal 180 defines a depth 1020 from a transition point 1022 between the face contacting surface 106 or a rearward or proximal-most surface adjacent the inwardly-projecting, nasal bridge accommodating portion that defines the edge 1000 in the upper portion 1002. Preferably, the depth 1020 is greater than a corresponding depth D of the Simplus® seal. With reference to FIG. 14, the greater depth 1020 (compared to depth D) can be created by extending the inwardly-projecting, nasal bridge accommodating portion further inward/forward and/or downward relative to the Simplus® seal. That is, in the illustrated arrangement, the inwardly-projecting, nasal bridge accommodating portion of the seal 180 continues beyond a termination edge S of the Simplus® seal to extend further and deeper into the interior of the cushion module 110, which results in the seal 180 having a greater depth 1020 (than depth D) and a smaller width 1012 (than width W) relative to the Simplus® seal. As a result, the seal 180 has a greater contact area or at least the potential of a greater contact area with the bridge of the user's nose relative to the Simplus® seal.

Figure 15:
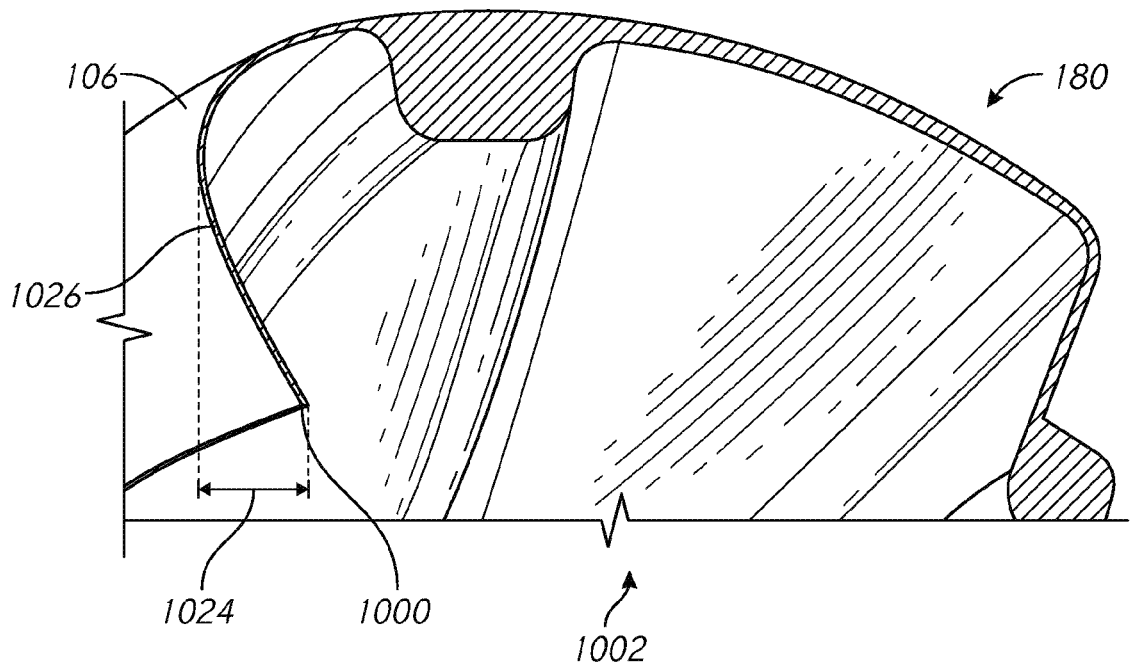
FIG. 15 is a sectional view of the upper portion of the seal.

FIG. 15 illustrates the upper, center portion of the seal 180 sectioned through the center or along the mid-plane of the seal 180 in a forward-rearward direction. The seal 180 defines a depth 1024 between a rearward-most point 1026 and a terminal edge 1000 along the center or mid-plane of the seal 180. The depth 1024 can be about 4.26 mm in one or more sizes or configurations of the seal 180. Preferably, the depth 1024 is equal to greater than about 3.5 mm, 3.75 mm, 4 mm or about 4.25 mm. In some configurations, the depth 1024 is equal to or less than about 6 mm or equal to or less than about 5 mm. For the sake of comparison, a corresponding depth of the Simplus® seal is about 2.75 mm. As described above, the greater depth 1024 of the seal 180 allows the nasal bridge accommodating portion to contact or potentially contact the bridge of the user's nose to improve the seal for at least some nasal geometries.

The illustrated seal 180 of the cushion module 110 comprises a fairly complex range and configuration of thicknesses, as shown in FIGS. 16-20. The thicknesses are varied to take advantage of or provide different characteristics in different regions of the illustrated seal 180. For example, the thicknesses in the various regions can be selected to address a desired characteristic for that region and/or the seal 180 as a whole. Such characteristics can include, for example, allowing the seal 180 to conform to the facial geometry of the user to enhance sealing properties or comfort, supporting the shape of the mask seal without significant internal gas pressure to facilitate fitment and/or in response to internal gas pressure and/or external pressure (e.g., caused by headgear forces) or providing strength or durability.

Figure 16:
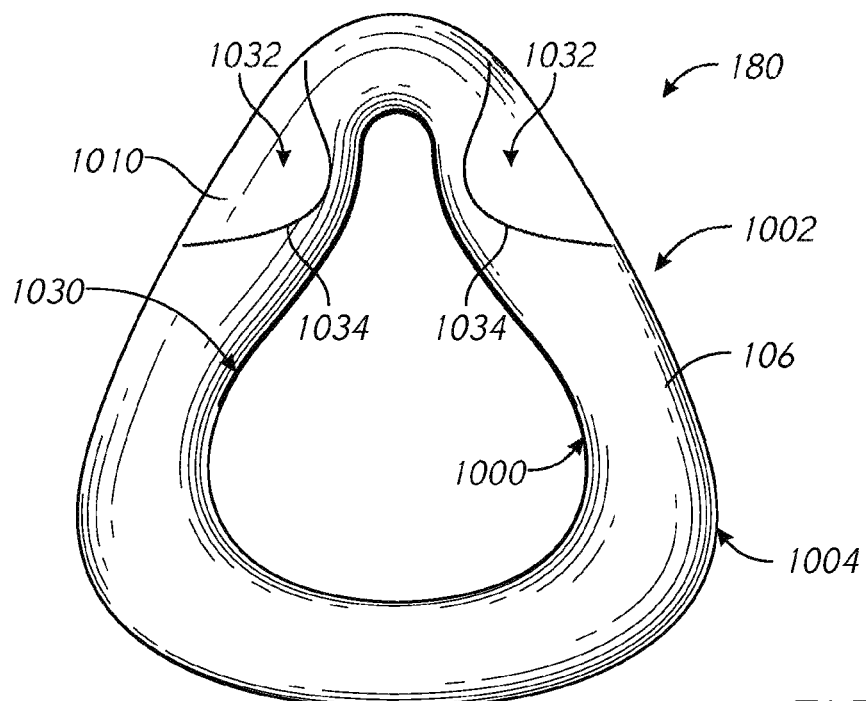
FIG. 16 is a plan view of a face contacting surface of a seal of one of the cushion modules of FIG. 8 illustrating regions having varied thicknesses.

With reference to FIG. 16, in some configurations, the seal 180 includes a continuous thin internal edge section 1030 of at least a portion of the edge that defines opening 1000 in the upper portion 1002 of the seal 180. That is, the thin internal edge section 1030 is a portion of the edge that defines opening 1000 that defines a thickness that is equal to or less than a certain thickness, as described below, along a continuous length of the edge that defines opening 1000. Preferably, the continuous thin internal edge section 1030 extends at least along the top center portion of the edge that defines opening 1000 and along the portions of the edge that contact the bridge of and laterally alongside the user's nose. In some configurations, the continuous thin internal edge section 1030 extends into the lower portion 1004 of the seal 180. In some configurations, the continuous thin internal edge section 1030 extends along at least the entire upper half of the seal 180. In some configurations, the continuous thin internal edge section 1030 extends along approximately the upper two-thirds or at least about the upper two-thirds of the seal 180. In some configurations, the continuous thin internal edge section 1030 extends inwardly from the edge that defines opening 1000 at least about 0.5 mm to about 1 mm. In some configurations, the thin edge section 1030 can extend further inwardly from the edge that defines opening 1000; however, it can be desirable for further inward portions of the seal 180 to have greater thicknesses. In some configurations, the thin edge section 1030 has a thickness that is less equal to or less than about 0.6 mm or equal or less than about 0.4 mm. The continuous thin internal edge section 1030 can vary in thickness in a direction extending inwardly from the edge that defines opening 1000 or along its length within these desired thickness ranges.

In some configurations, the seal 180 also or alternatively includes thickened nose pads 1032. The thickened nose pads 1032 preferably are positioned on each lateral side of the upper portion 1002 of the opening 1000. Preferably, the thickened nose pads 1032 extend along at least a portion of the face contacting surface 106 of the seal 180 but do not extend in a lateral direction all the way to the edge that defines the opening 1000. That is, innermost edges of the nose pads 1032 terminate prior to the edge that defines the opening 1000. In some configurations, the thickened nose pads 1032 are created by thickened regions of the seal 180 wherein the additional material extends inwardly into the interior of the cushion module 110. The thickened nose pads 1032 can have laterally inward edges 1034 that are curved (e.g., U-shaped) with centers of the curved portions being positioned closer to the opening 1000 than upper and lower portions of the curved edge 1034.

Figure 17:
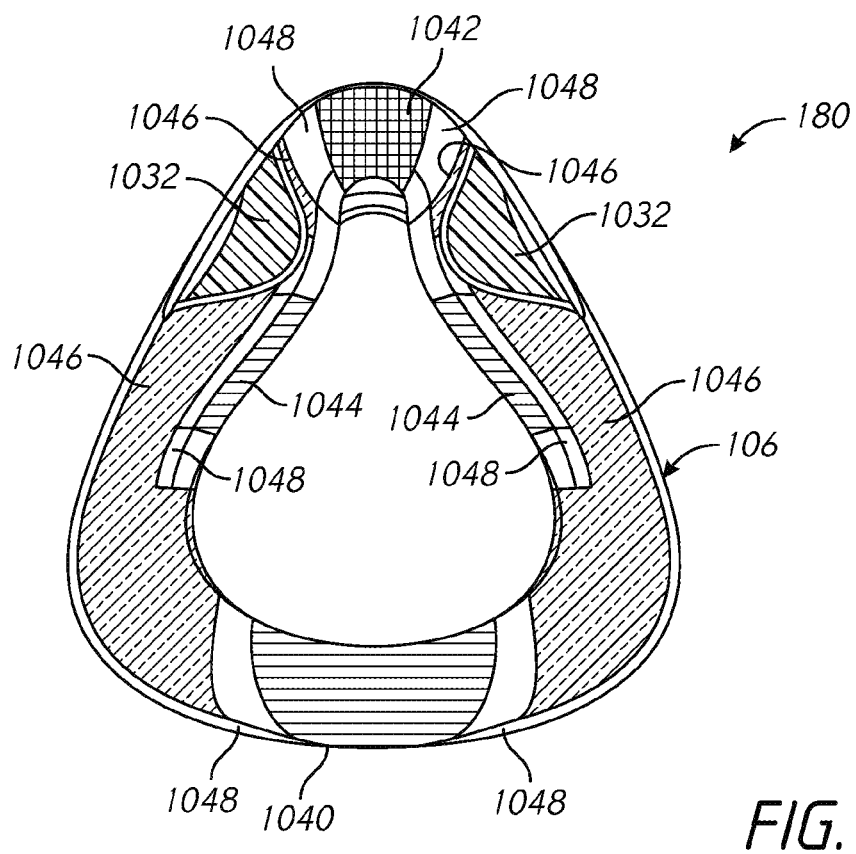
FIG. 17 is a plan view of a face contacting surface of a seal of one of the cushion modules of FIG. 8 illustrating additional varied thickness regions relative to FIG. 16.

FIG. 17 illustrates differences in thicknesses of the seal 180 in various regions or portions. The regions and portions are color coded in FIG. 17. Typically, the outer surface of the seal 180 is of a substantially smoothly curved shape with variations in thickness being accomplished by inwardly-extending portions of the inner surface of the seal 180, as apparent, for example, in FIGS. 18 and 22. The seal 180 can include one or more of the regions or portions described herein.

The illustrated seal 180 comprises a bottom or chin region 1040. The chin region 1040 in the illustrated seal 180 extends along at least a portion of the opening 1000. Preferably, the chin region 1040 extends along at least a lower, central portion of the opening 1000 that is positioned below the lower lip of the user on or near the user's chin. The chin region 1040 can extend along an entirety or a substantial entirety of a height of the lower section of the face contacting surface 106 of the seal 180. In other words, the chin region 1040 can extend from a lower end of the outer edge 1010 to a lower end of the edge that defines the opening 1000. The chin region 1040 can extend along a substantial portion of a width of the seal 180, such as at least about one-half or more of a maximum width of the opening 1000. The illustrated chin region 1040 is centered in a lateral direction of the seal 180.

The chin region 1040 can be a relatively soft region that contacts the area below the lower lip of the user and can allow the seal 180 to accommodate a range of chin geometries. Accordingly, the chin region 1040 can have a thinner cross-section than other regions of the seal 180. In some configurations, the chin region 1040 has the smallest thickness of the seal 180, which may be equal to a thickness of other regions. For example, a portion or an entirety of the chin region 1040 can have a thickness of about 0.3 mm. In some configurations, the thickness of the chin region 1040 can be less than 0.3 mm. For example, the thickness could be as low as about 0.15 mm.

The seal 180 can also include a top or nasal bridge region 1042 located at the top center of the seal 180 and extending along the top of the opening 1000. Similar to the chin region 1040, the nasal bridge region 1042 can extend along an entirety or a substantial entirety of a height of the top section of the face contacting surface 106 of the seal 180. The nasal bridge region 1042 can extend in a lateral direction a distance about equal to the width 1012 (FIG. 12). In the illustrated arrangement, the nasal bridge region 1042 has a generally inverted trapezoidal shape, with the longer edge being located above the shorter edge. However, in other configurations, the nasal bridge region 1042 could have other shapes.

Given a desire to gently seal against the bridge of the nose, the nasal bridge region 1042 in the illustrated configuration has a fairly small thickness. In some configurations, the nasal bridge region 1042 has the smallest thickness of the seal 180, which can be equal to the thickness of other portions of the seal 180. For example, a portion or an entirety of the nasal bridge region 1042 can have a thickness that is equal to the thickness of the chin region 1040. In some configurations, the thickness of a portion or an entirety of the nasal bridge region 1042 is about 0.3 mm. In some configurations, the thickness of the entirety the nasal bridge region 1042 is about 0.3 mm. In some configurations, the thickness of the nasal bridge region 1042 can be less than 0.3 mm. For example, the thickness could be as low as about 0.15 mm. However, it has been determined that lower thicknesses can result in or increase the likelihood of creasing of the nasal bridge region 1042 for some facial geometries and/or under some operational gas pressures. Keeping the thickness at or above about 0.3 mm in a substantial portion or an entirety of the nasal bridge region 1042 can reduce the incidence of creasing over a substantial range of operational pressures, which may comprise an entire range of normal operating pressures.

The illustrated seal 180 also includes lateral portions 1044 located along or adjacent to lateral sides of the opening 1000. In the illustrated arrangement, the lateral portions 1044 are elongate strips that extend along vertical center portions of each lateral side of the opening 1000. The lateral portions 1044 extend generally from an upper end of the lower portion 1004 of the seal 180 to a lower end of the upper portion 1002 of the seal 180. The lateral portions 1044 can be located on the seal 180 to extend along the user's cheeks beside the user's nose.

Preferably, to conform to a wide variety of facial geometries and maintain a seal in the present of creases, lines or wrinkles that may be present on the user's cheeks and/or caused by facial movements (e.g., smiling), the lateral portions 1044 preferably have a relatively low thickness. For example, in some configurations, the lateral portions 1044 have the smallest thickness of the seal 180, which can be equal to the thickness of other portions of the seal 180. For example, a portion or an entirety of each of the lateral portions 1044 can have a thickness that is equal to the thickness of one or both of the chin region 1040 and the nasal bridge region 1042. In some configurations, the thickness of a portion or an entirety of each of the lateral portions 1044 is about 0.3 mm. In some configurations, the thickness of the entirety of the lateral portions 1044 is about 0.3 mm. In some configurations, the thickness of a portion or an entirety of each of the lateral portions 1044 can be less than 0.3 mm. For example, the thickness could be as low as about 0.15 mm.

The illustrated seal 180 includes outer peripheral portions 1046 that extend along lateral portions of an outer periphery of the seal 180. To reduce the incidence of wrinkling of at least some of the face contacting regions of the seal 180 during use, it has been found that the outer peripheral portions 1046 of the seal 180 should be fairly rigid. In the illustrated arrangement, the outer peripheral portions 1046 extend along the generally vertically extending, laterally outward portions of the face contacting surface 106 of the seal 180.

In the illustrated arrangement, the outer peripheral portions 1046 extend along a substantial portion of a height of the lower portion 1004 of the opening 1000 each lateral side of the opening 1000. In some configurations, the outer peripheral portions 1046 extend along an entire height of the lower portion 1004 of the opening 1000. Upper ends of the outer peripheral portions 1046 can extend at least to about a vertical location at which the opening 1000 narrows significantly to form the upper portion 1002 that accommodates a bridge of the user's nose. Lower ends of the outer peripheral portions 1046 can extend toward, to or below a lower end of the opening 1000. The chin region 1040 can be positioned between lower ends of the outer peripheral portions 1046. Each of the outer peripheral portions 1046 and the chin region 1040 can define a portion of a lower edge of the opening 1000.

In the illustrated arrangement, upper portions of the outer peripheral portions 1046 are spaced outwardly from the edge that defines the opening 1000. In some configurations, the outward spacing of the upper portions of the outer peripheral portions 1046 accommodates the lateral portions 1044 between the opening 1000 and the upper portions of the outer peripheral portions 1046. In some configurations, lower portions of the outer peripheral portions 1046 extend close to the opening 1000 compared to upper portions of the outer peripheral portions 1046. In the illustrated configuration, lower portions of the outer peripheral portions 1046 extend substantially to or to the edge that defines the opening 1000.

The relatively increased thickness of the outer peripheral portions 1046 can assist in resisting or preventing collapse of the seal 180 in the absence of significant internal gas pressure to facilitate fitment and provide feedback to the user, such as in response to applied forces (e.g., headgear forces). The outer peripheral portions 1046 can help maintain the curved shape of the lateral sides of the seal 180 and/or help maintain a separation between a rear wall of the seal 180 (defining the face contacting surface 106) and a front end or wall of the seal 180, seal housing 190 or other structure immediately forward of the face contacting surface 106. In some configurations, the thickness of a portion or an entirety of the outer peripheral portions can be between about 1.0 mm and about 2.0 mm. In the illustrated configuration, a portion or an entirety of the outer peripheral portions 1046 preferably have a thickness of about 1.5 mm. The thicknesses of the outer peripheral portions 1046 can be consistent or varied.

As described above, the seal 180 can include thickened nose pads 1032. The thickened nose pads 1032 preferably are positioned on each lateral side of the upper portion 1002 of the opening 1000. In the illustrated configuration, the nose pads 1032 intersect the outer peripheral portions 1046, such that a portion of the outer peripheral portions 1046 is located both above and below the nose pads 1032. Preferably, the thickened nose pads 1032 extend along at least a portion of the face contacting surface 106 of the seal 180 but do not extend all the way to the edge that defines the opening 1000. That is, a laterally inward edge 1034 of each of the nose pads 1032 terminates prior to the edge that defines the opening 1000. Laterally outward edges of the nose pads 1032 can extend substantially to or to the outer edge 1010 of the face contacting surface 106 of the seal 180. The laterally inward edges 1034 can be curved with centers of the curved portions being positioned closer to the opening 1000 than upper and lower portions of the curved edge 1034. In other words, the curved edges 1034 can be generally U-shaped with the bottom of the U-shape being positioned closer to the opening 1000 and the top of the U-shape being positioned further from the opening 1000.

Figure 18:
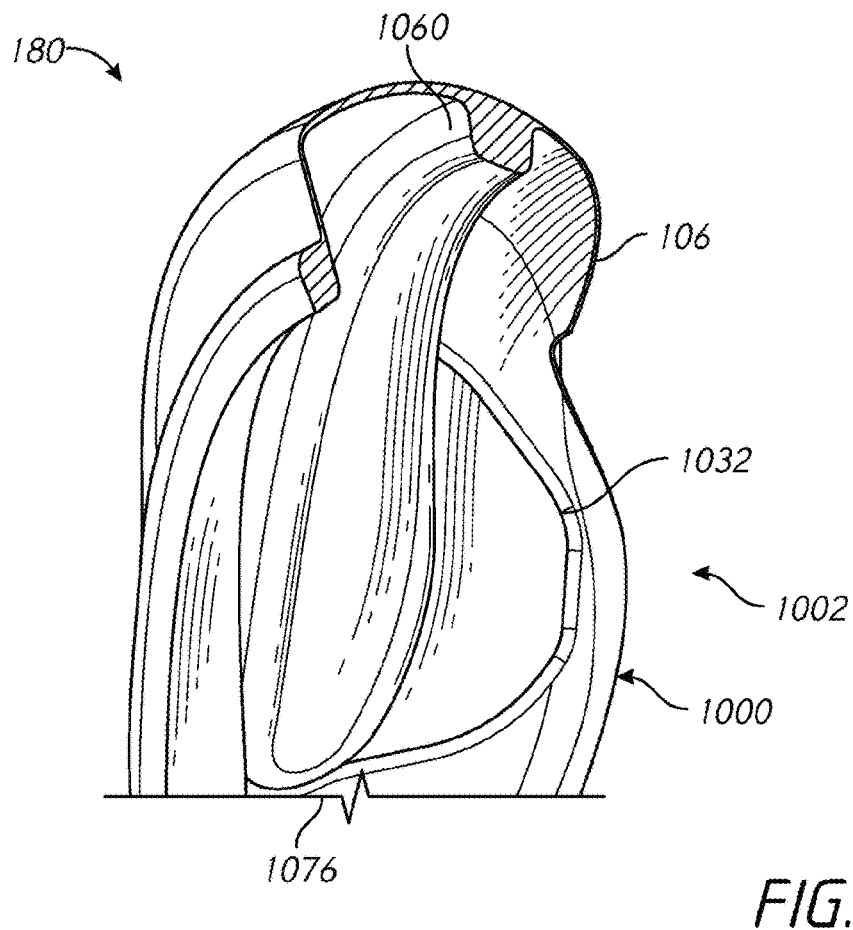
FIG. 18 is a perspective view of an interior of a sectioned upper portion of a seal.

With reference to FIG. 18, in some configurations, the thickened nose pads 1032 are created by thickened regions of the seal 180, wherein the additional material extends inwardly into the interior of the cushion module 110. The nose pads 1032 can extend into a stiffening portion of the seal 180, such as a thickened band 1060, which extends from one side to the other over the top of the seal 180 and is described in additional detail below. It has been discovered by the present inventors that the presence of the nose pads 1032 can result in a dramatic reduction in leaks occurring at the side of the user's nose. In addition, by terminating the nose pads 1032 prior to the opening 1000, comfort can be maintained.

It has been discovered that the nose pads 1032 should be relatively thick to improve sealing performance of the seal 180, but not so thick as to cause discomfort. In some configurations, the nose pads 1032 are among the thickest or are the thickest portions of the face contacting surface 106 of the seal 180. In some configurations, the nose pads 1032 are at least as thick as the outer peripheral portions 1046. In some configurations, the nose pads 1032 are thicker than the outer peripheral portions 1046. In some configurations, the nose pads 1032 are between about 1.5 mm and 2.0 mm in thickness. In some configurations, the nose pads 1032 are about 1.8 mm in thickness.

Figure 19:
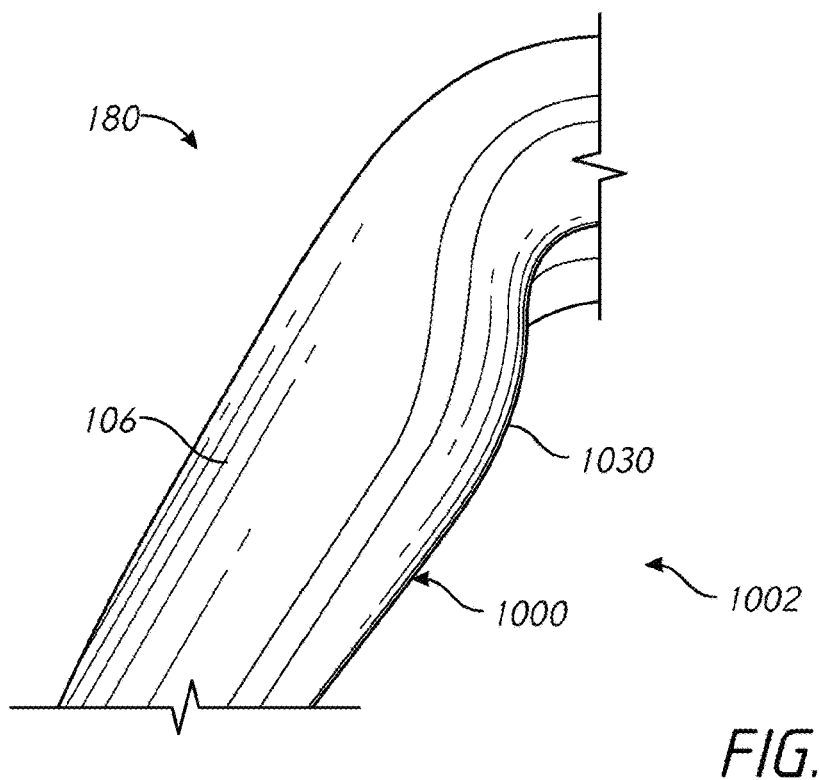
FIG. 19 is a plan view of a face contacting surface of an upper lateral portion of the seal.

With reference to FIG. 19, as described above, the illustrated seal 180 includes a continuous thin internal edge section 1030 of at least a portion of the edge that defines the opening 1000 in the upper portion 1002 of the seal 180. The continuous thin internal edge section 1030 is not necessarily a discrete section, but can be partially or completely defined by other portions of the seal (e.g., the lateral portions 1044 or nasal bridge portion 1042) so long as the entire section 1030 is below the desired thickness. In some configurations, the continuous thin internal edge section 1030 extends along about or at least about the entire upper half of the seal 180. In some configurations, the continuous thin internal edge section 1030 extends along approximately the upper two-thirds or at least about the upper two-thirds of the seal 180. In some configurations, the continuous thin internal edge section 1030 extends inwardly from the edge that defines opening 1000 at least about 0.5 mm to about 1 mm. In some configurations, the thin edge section 1030 can extend further inwardly from the edge that defines opening 1000; however, it can be desirable for further inward portions of the seal 180 to have greater thicknesses, as described above.

In some configurations, the thin edge section 1030 has a thickness that is less equal to or less than about 0.6 mm or equal or less than about 0.4 mm. In some configurations, at least the first 0.5 mm extending from the edge that defines the opening 1000 is less than about 0.4 mm. The continuous thin internal edge section 1030 can vary in thickness in a direction extending inwardly from the edge that defines opening 1000 or along its length within these desired thickness ranges. It has been discovered by the present inventors that providing the continuous thin internal edge section 1030 improves the sealing characteristics of the seal 180 for at least some conditions or facial geometries.

The seal 180 can have other portions outside of those described above. For example, the seal 180 can have one or more transition portions 1048 in the area(s) between the above-described portions. The transition portion 1048 can be referred to in the singular herein; however, the transition portion 1048 is not necessarily a single contiguous region, but may comprise several discrete or non-contiguous regions. The transition portion 1048 can define a transitioning thickness between any one or more (including all) of the chin region 1040, nasal bridge region 1042, lateral portions 1044, the outer peripheral portions 1046 and the nose pads 1032. The transition portion 1048 can define a thickness that extends away from or is positioned or transitions between two regions in any suitable manner, such as a gradual or abrupt transition, for example. A transition in thickness can occur within the transition portion 1048 or along an edge of the transition portion 1048, for example. In the illustrated configuration, the outer peripheral portions 1046 are generally surrounded by the transition portion 1048. The chin region 1040 can be separated from the outer peripheral portions 1046 by a transition portion 1048. The nasal bridge region 1042 can be separated from the outer peripheral portions 1046 and/or the nose pads 1032 by a transition portion 1048. Similarly, the lateral portions 1044 can be separated from the outer peripheral portions 1046 by a transition portion 1048. Other configurations also are possible.

Figure 20:
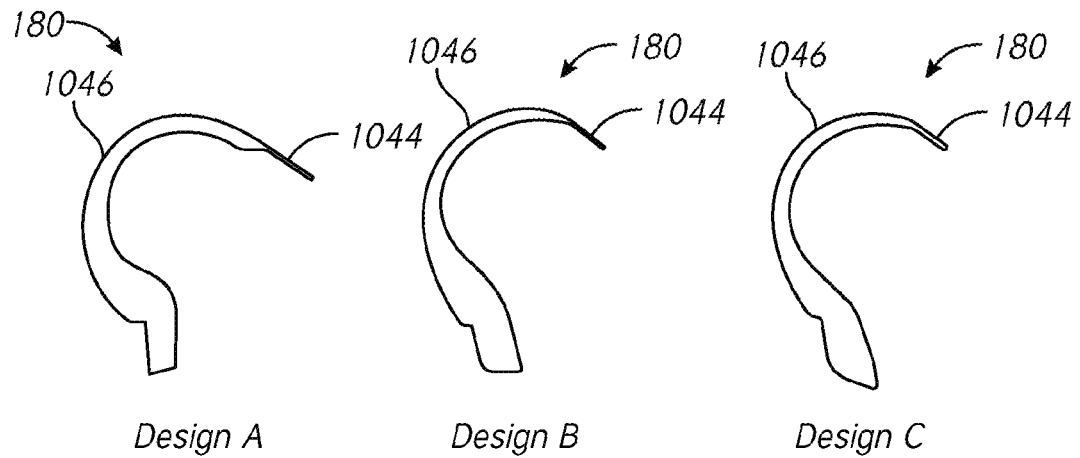
FIG. 20 illustrates several possible cross sectional profiles for a portion of the seal.

FIG. 20 illustrates several sectional views of one side of several different designs of the seal 180. The section is created by a substantially horizontal cut line through a portion of the seal 180 containing the lateral portion 1044 and outer peripheral portion 1046. Design A of FIG. 20 includes an inner surface (right side in FIG. 20) that has a relatively abrupt change in direction identified in the figure as a bend point. Thus, a different in the thickness of the seal 180 on each side of the bend point varies fairly substantially. As a result, it has been discovered that the seal 180 tends to bend around the bend point instead of deforming in a relatively uniform manner as the seal 180 is pressed against a user's face. Design B illustrates a smoother curved shape to the inner surface, which improves the ability of the seal 180 to deform in a uniform manner. Design C illustrates a further smoothed curved shape relative to Design B. Thus, Designs B and C represent an improved cross-sectional shape for the seal 180 relative to Design A, with Design C being somewhat more preferred than Design B. The more uniform the deformation of the seal 180, or the more the seal 180 cross-section changes from a generally circular shape to a generally squashed or compressed ellipse shape, rather than simply collapsing about a point or small region, the larger the seal contact area on the face, which reduces pressure on the user's skin and allows the seal to better conform to different facial geometries.

In at least some configurations, the upper portion 1002 of the seal 180 is designed to roll over onto an outer surface of the cushion module 110, which allows the nasal bridge region 1042 to move in a forward direction relative to a lower portion 1004 of the seal 180. With reference to FIGS. 21-28, to assist with the rolling of the upper portion 1002, the upper portion 1002 can have a varying thickness or a varying stiffness. While the illustrated configuration uses a region 172 of reduced thickness, other means for providing the reduced stiffness region also can be used to induce rolling of the seal 180. For example, the material of the seal 180 can be configured to have a reduced stiffness through material selection or material properties. In addition, a composite of materials can be used to provide a region of reduced stiffness or rigidity. Moreover, a combination of any suitable techniques can be used. Nevertheless, the illustrated region 172, which is configured with reduced thickness, provides a simple manner of achieving the region of reduced stiffness 172. In addition, by adjusting the stiffness of the reduced stiffness region 172, the force required to induce rolling of the region 172 can be controlled, which controls the force applied against the nose of the user. For example, by varying the stiffness, movement can become increasingly or decreasingly resisted over the range of movement. The region of reduced stiffness 172 can also be referred to as a rolling portion.

Figure 21:
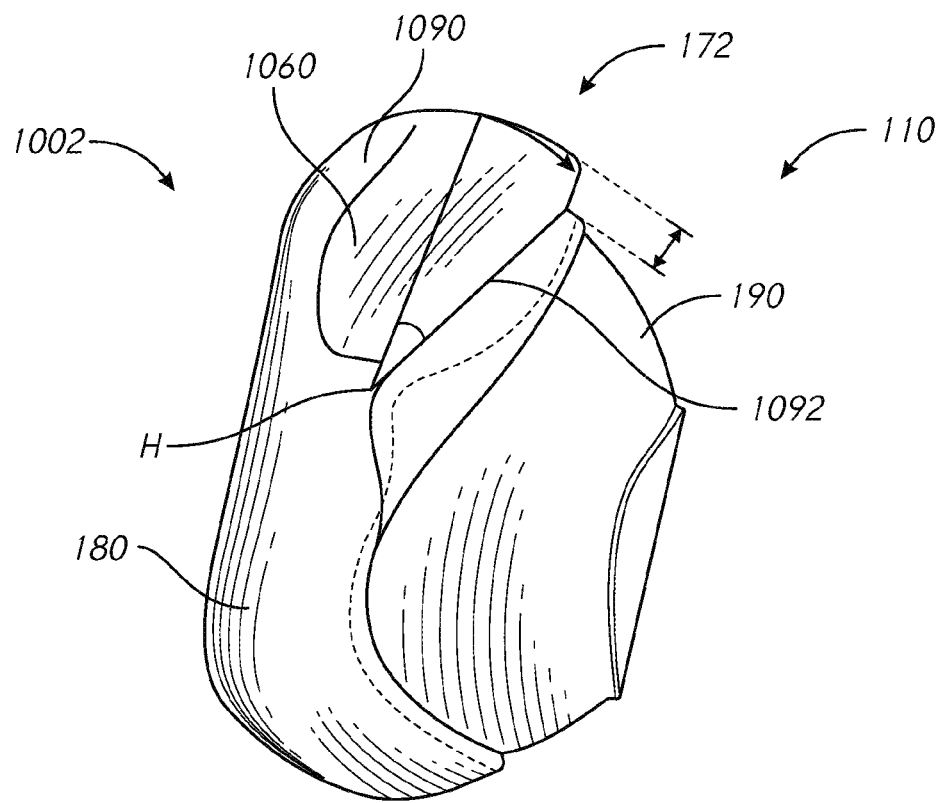
FIG. 21 is a side view of a cushion module having a deformable upper portion.
Figure 22:
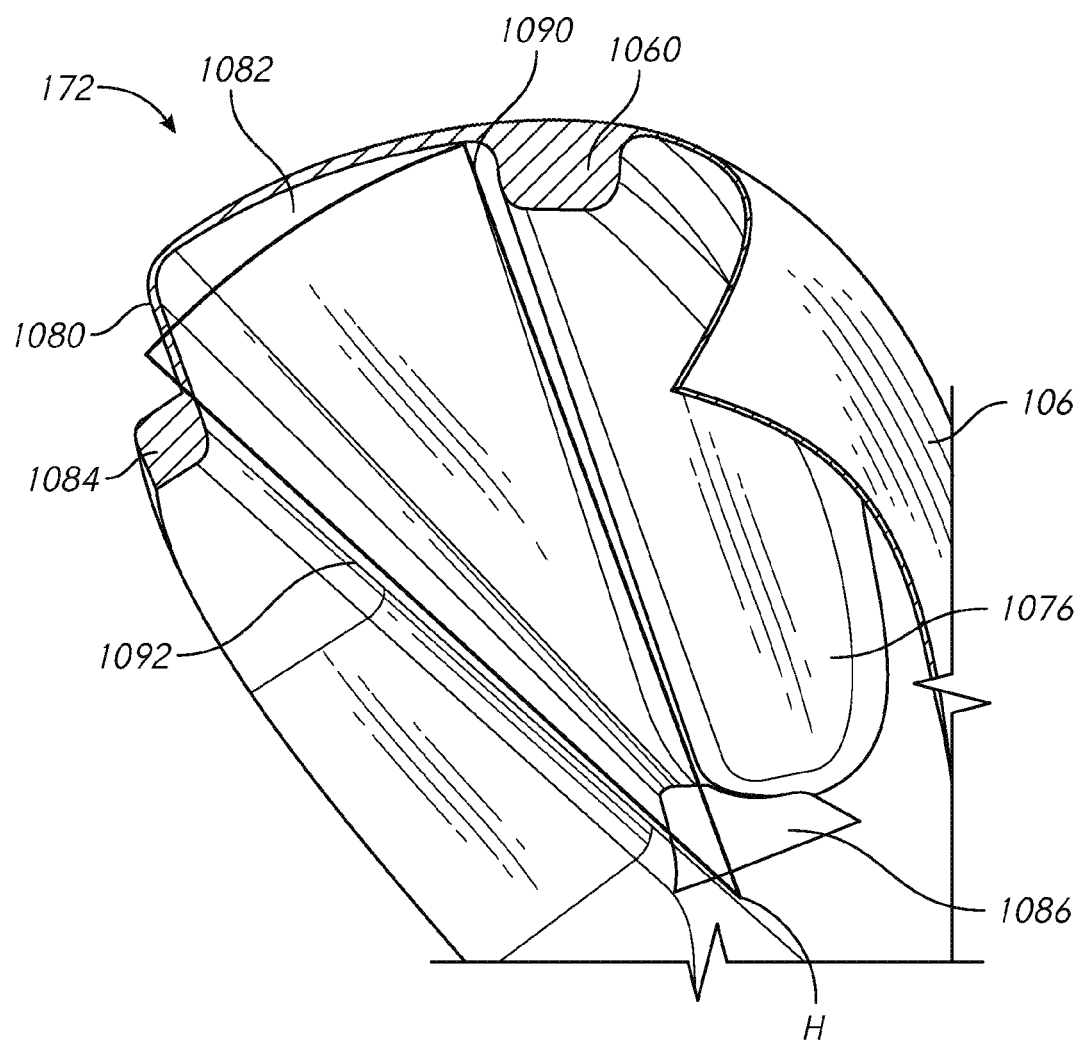
FIG. 22 is sectional view of an interior surface of the upper portion of a seal of a cushion module having a deformable upper portion.

With reference to FIGS. 21 and 22, to reduce the prevalence of ballooning in the upper portion 1002 and to provide enhanced structure in the upper portion 1002 to facilitate rolling in a desired portion of the seal 180, a reinforcing component or components, such as a band 1060, can be positioned along at least a portion of the upper portion 1002. The band 1060 can be a component formed of a material that is more rigid than, or that features increased stiffness relative to, the silicone or other material forming the seal 180. For example, a region of significantly increased thickness relative to the region of reduced stiffness 172, where the region is formed of the same material forming the seal 180, can be used to increase the stiffness of the reinforcing component or components.

In some configurations, the band 1060 can be a separately formed component that is at least partially encased by the material of the seal 180. For example, the band 1060 can be a co-moulded plastic component or the seal 180 can be overmolded onto the band 1060. In some configurations, the band 1060 can be defined by a portion of the upper portion 1002 that has enhanced stiffness relative to surrounding regions. For example, but without limitation, the band 1060 can be defined by a portion of increased thickness, a portion of differing materials or material properties that result in increased stiffness or the like. In the illustrated arrangement, the band 1060 comprises a region of increased thickness of the base material of the seal 180, similar to the differing regions of thickness described above with reference to FIG. 17.

In some configurations, the band 1060 extends along at least a portion of the upper portion 1002 of the seal 180. The upper portion 1002 of the seal 180 comprises an apex 1070 (FIG. 8) when viewed from the front. The apex 1070 can be defined as a tip, a top and an angular summit of the seal 180, which apex 1070 is positioned in proximity to the nose of the user when in use. A first side wall 1072 and a second side wall 1074 converge at the apex 1070 in the illustrated configuration. The first side wall 1072 and the second side wall 1074 extend along at least a portion of the upper portion 1002 of the seal 180. In some configurations, the first side wall 1072 and the second side wall 1074 extend below the upper portion 1002 into the lower portion 1004 of the seal 180.

In some configurations, at least a portion of the first side wall 1072 and at least a portion of the second side wall 1074 are reinforced by the band 1060. In the illustrated configuration, the band 1060 reinforces at least a portion of the first wall 1072 and at least a portion of the second wall 1074. In some configurations, the band 1060 reinforces at least a portion of the first wall 1072, at least a portion of the second wall 1074 and the apex 1070.

With reference to FIGS. 18 and 22, the illustrated band 1060 has a first end 1076 and a second end (not shown) that is opposite to the first end 1076. The illustrated band 1060, as well as the seal 180, is symmetrical about a center line or mid-plane of the seal 180. Accordingly, the opposite side of the band 1060 including the second end is a mirror image of the illustrated side including the first end 1076. The first end 1076 and the second end can be located at or near a bottom end of the nose pads 1032, as illustrated in FIG. 18. The first end 1076 and the second end could be located relatively higher or relatively lower to make the band 1060 shorter or longer, respectively, depending on the amount of reinforcement desired. The illustrated band 1060 flares outwardly at the ends 1076 and is narrower in a forward-rearward direction in the center. However, other shapes are also possible.

With reference to FIGS. 21 and 22, the illustrated region of reduced stiffness 172 comprises a first or front wall portion (hereinafter, front wall 1080) and a second or top wall portion (hereinafter, top wall 1082). In the illustrated arrangement, the front wall 1080 is a relatively vertical wall that extends upwardly from a connection portion 1084 between the seal 180 and the seal housing 190. The top wall 1082 is a relatively horizontal wall that extends rearwardly from an upper end of the front wall 1080 towards or to the band 1060. The illustrated front wall 1080 and the top wall 1082 are generally L-shaped in cross-section to form an angle (e.g., an approximately 90 degree angle) therebetween in a neutral or unloaded condition of the upper portion 1002 of the seal 180. However, in other configurations, the reduced stiffness region 172 could have a rounded or curved profile defined by a single wall or in which a distinction between a first wall portion and a second wall portion is less apparent.

The front wall 1080 and the top wall 1082 extend downwardly from the apex 1070 along the first and second walls 1072, 1074 (FIG. 8). In the illustrated arrangement, the front wall 1080 and top wall 1082 extend to and terminate at an inwardly-projecting shelf portion 1086 on each side of the seal 180. In the illustrated arrangement, each of the shelf portions 1086 is located just below the ends 1076 of the band 1060. The shelf portions 1086 help to influence the portion of the seal 180 that deforms along with the reduced stiffness region 172 when the upper portion 1002 of the seal 180 moves forward. In some configurations, the shelf portions 1086 contain or substantially contain the deformation of the seal 180 resulting from forward movement of the upper portion 1002 to the reduced stiffness region 172.

In some configurations, the connection portion 1084 and a forward edge of the band 1060 converge in a direction from the apex 1070 to the shelf 1086. In the illustrated arrangement, the connection portion 1084 and the forward edge of the band 1060 remain somewhat spaced from one another at or near the shelf 1086. From a side profile view, the reduced stiffness region 172 defines a generally triangular or wedge shape, as illustrated in FIGS. 21 and 22, for example.

In some configurations, the region of reduced stiffness or rolling portion 172 is located between and can be bounded by a first boundary 1090 and a second boundary 1092, wherein the first boundary 1090 and the second boundary 1092 have an increased stiffness relative to the region of reduced stiffness 172. In the illustrated configuration, for example, the first boundary 1090 is defined by or alongside a portion of the band 1060 (e.g., the forward edge of the band 1060) while the second boundary 1092 is defined by or alongside the connecting portion 1084 (e.g., origination of the front wall 1080) or a bend or transition between the front wall 1080 and the top wall 1082. In some configurations, the second boundary 1092 can be defined by or alongside an edge of the more rigid seal housing 190. In some configurations, the second boundary 1092 can be defined along a portion of the seal 180 positioned between the seal housing 190 and the region of reduced stiffness 172. A hinge axis H for movement of the upper portion 1002 of the seal 180 is defined by or is located near an intersection of the first boundary 1090 and the second boundary 1092, or projections thereof.

Figure 28:
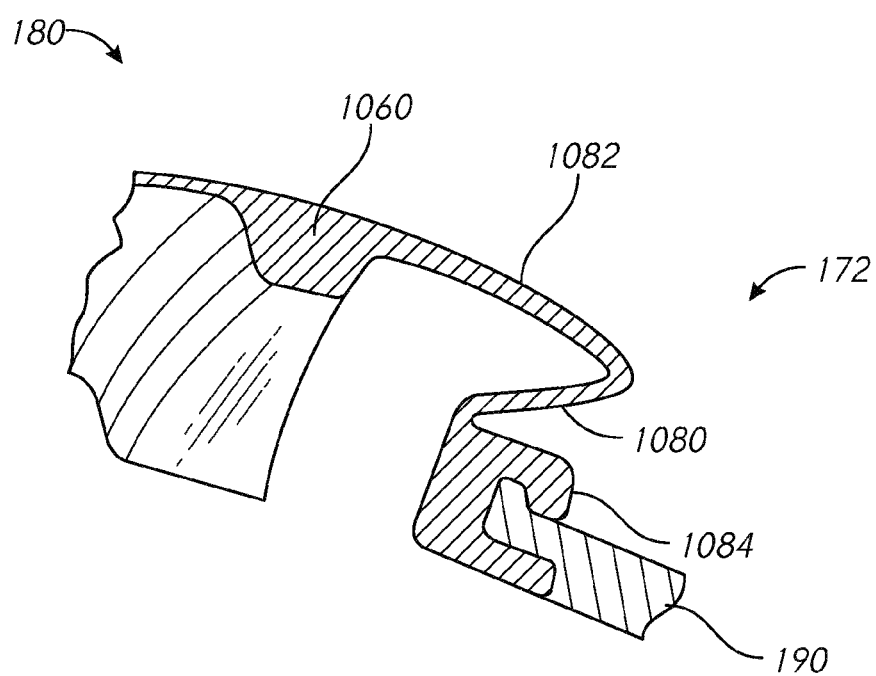
FIG. 28 is a sectional view of an upper portion of a seal deflected in a forward direction.
Figure 29B:
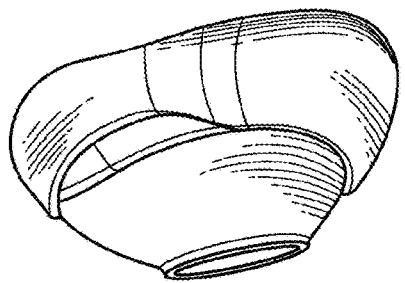
FIG. 29B illustrates another view of a cushion module having a seal in accordance with one or more embodiments disclosed herein in a neutral position.
Figure 29C:
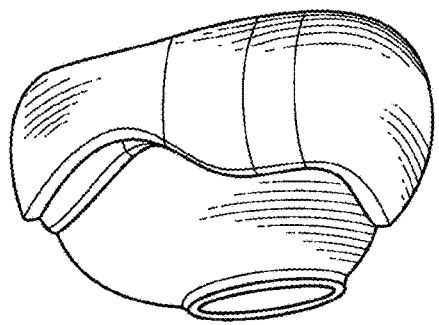
FIG. 29C illustrates yet another view of a cushion module having a seal in accordance with one or more embodiments disclosed herein in a depressed position.
Figure 29E:
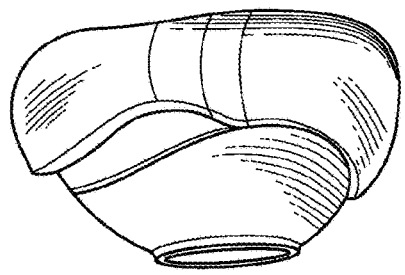
FIG. 29E illustrates yet another view of a cushion module having a seal in accordance with one or more embodiments disclosed herein in a neutral position.
Figure 29F:
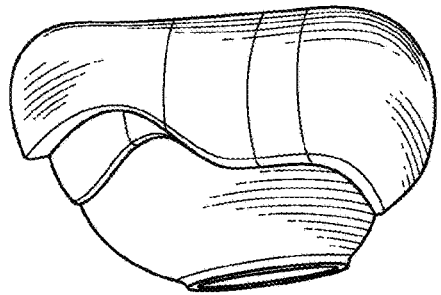
FIG. 29F illustrates yet another view of a cushion module having a seal in accordance with one or more embodiments disclosed herein in a depressed position.
Figure 29A:
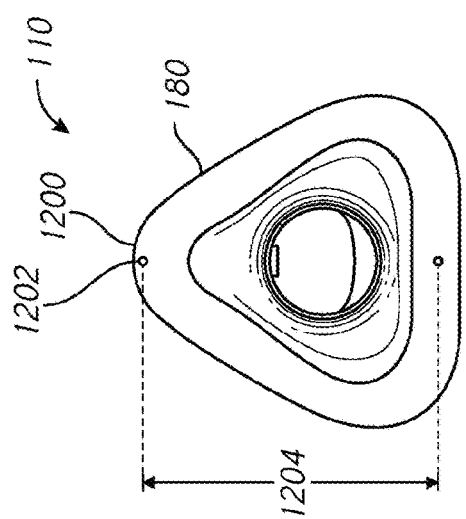
FIG. 29A illustrates a view of a cushion module having a seal in accordance with one or more embodiments disclosed herein. A Simplus® cushion module is illustrated in similar positions for the sake of comparison.
Figure 29D:
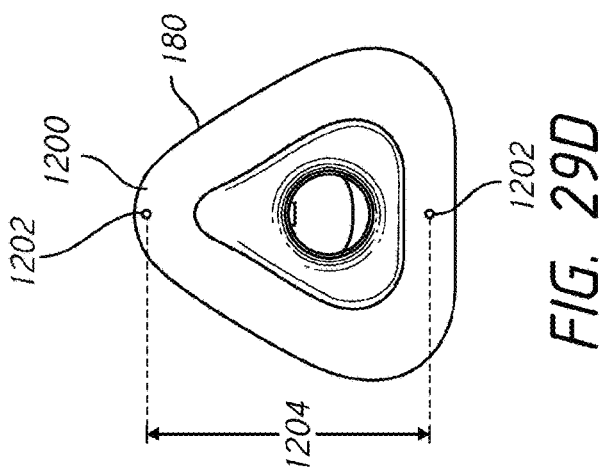
FIG. 29D illustrates yet another view of a cushion module having a seal in accordance with one or more embodiments disclosed herein.

With reference to FIG. 28, as the upper portion 1002 of the seal 180 is displaced about the hinge axis H, the roll increases in size. In other words, as the first boundary 1090 initially moves toward the second boundary 1092, a roll is formed in the seal 180. As the first boundary 1090 continues to move toward the second boundary 1092, the roll continues to increase in size. Thus, in at least some configurations, the roll defined in the upper portion 1002 starts at nothing and progressively increases during displacement of the upper portion 1002. Preferably, the rolling between the first boundary 1090 and the second boundary 1092 creates a single bend or inflection between the first boundary 1090 and the second boundary 1092. The single bend results in legs approaching the bend location that increase in size as the first boundary 1090 moves toward the second boundary 1092. In other words, the rolling created by movement of the first boundary 1090 toward the second boundary 1092 preferably does not result in a fan-folding appearance, such as a pleated configuration.

In at least some configurations in which multiple size cushion modules 110 or seal 180 are provided, it can be desirable for the regions of reduced stiffness 172 of the different sizes to have different arrangements, properties or dimensions from one another. For example, the regions of reduced stiffness 172 can define different angles between the boundaries 1090, 1092 in a relaxed position between the various sizes. In addition, or in the alternative, the regions of reduced stiffness 172 can define different heights of the front wall 1080 (or different total lengths of the front wall 1080 and the top wall 1082) between the various sizes. FIGS. 23-26 illustrate different angles and different front wall 1080 heights between several sizes of a cushion module 110 or seal 180.

Figure 23:
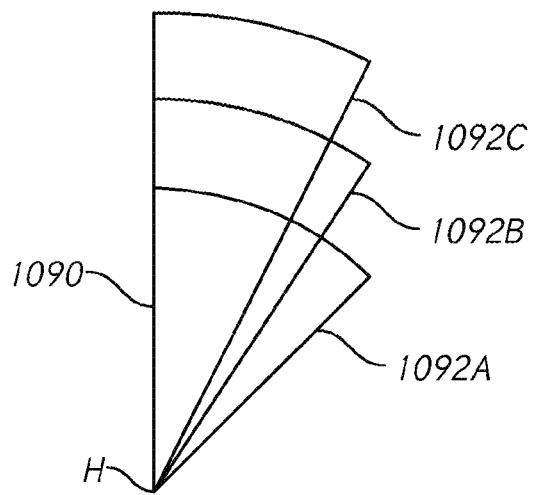
FIG. 23 illustrates a relationship between a deflection angle and forward movement of an upper portion of a seal.
Figure 24:
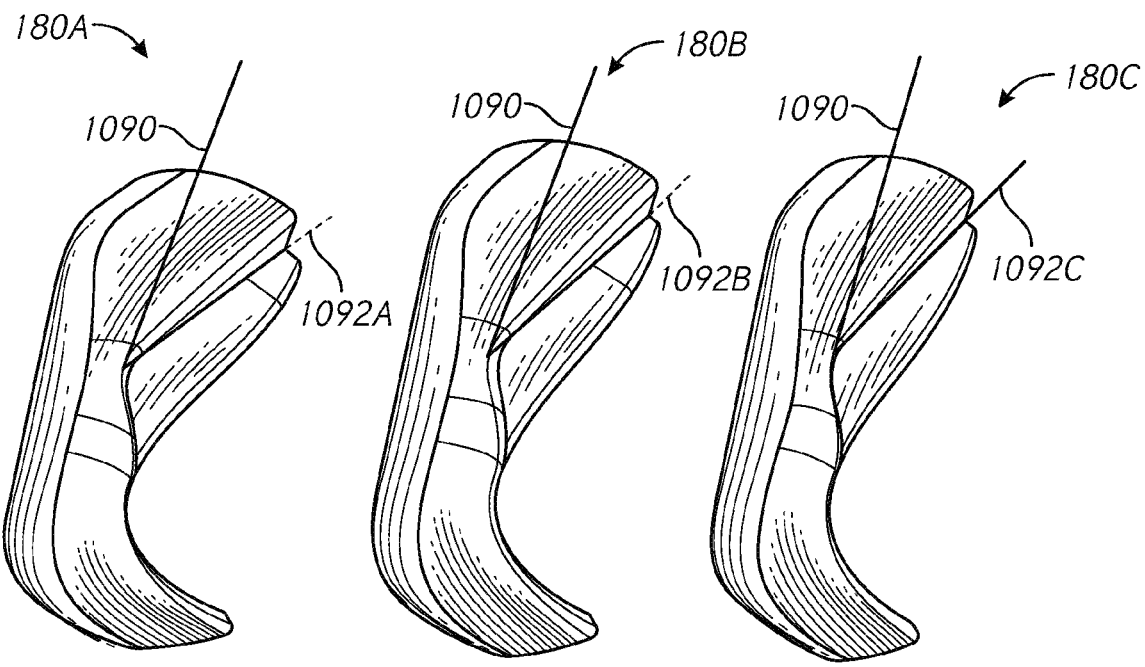
FIG. 24 illustrates several seals of different sizes having different available deflection angles.

With reference to FIGS. 23 and 24, three different sizes of seals 180a, 180b, 180c are illustrated. The seals 180a, 180b, 180c can be the seals of the three cushions modules 110a, 110b, 110c of FIGS. 8 and 9, for example. FIG. 23 illustrates a relationship between a length of the boundaries 1090, 1092 and a maximum forward displacement of the upper portion 1002. Assuming that a length of the upper portion 1002 increases or decreases along with an increase or decrease in a length of the seal 180, a length of the boundaries 1090, 1092 also increases or decreases. If the available deflection angle between the boundaries 1090, 1092 is held constant between the seal 180 sizes, the available maximum forward displacement of the upper portion 1002 is relatively less in smaller seal 180 sizes and relatively greater in larger seal 180 sizes.

For example, FIG. 23 illustrates first boundaries 1090 and second boundaries 1092a, 1092b, 1092c for three sizes of a seal 180. Assuming that all three illustrated seal 180 sizes are provided with a maximum available deflection angle (e.g., angle between the boundaries 1090 and 1092) that is equal to the maximum deflection angle of the large seal 180c, the maximum available forward displacements of the upper portions 1002 of the seals 180a and 180b are illustrated by the intersection between boundary 1092c and the arc lines of boundaries 1092a and 1092b. FIG. 23 illustrates that by increasing the angle between the boundaries 1090, 1092 in the smaller sizes, the maximum available forward displacement of the upper portions 1002 can be the same or similar between the several sized seals 180a, 180b, 180c. Thus, preferably, the angle between the boundaries 1090, 1092 is greatest in the smallest size seal 180a and smallest in the largest size seal 180c. However, in other configurations, the smallest size seal can have an angle that is greater than at least one of the larger sizes. Similarly, the largest size seal can have an angle that is less than at least one of the smaller sizes.

In some configurations, the small seal 180a defines an angle between the boundaries 1090, 1092a at a relaxed position of the upper portion 1002 of at least about 30 degrees. In some configurations, the angle is about 34 degrees. In some configurations, the medium seal 180b defines an angle between the boundaries 1090, 1092b at a relaxed position of the upper portion 1002 of between about 25 degrees and about 35 degrees. In some configurations, the angle is about 29 degrees. In some configurations, the large seal 180c defines an angle between the boundaries 1090, 1092c at a relaxed position of the upper portion 1002 of between about 20 degrees and about 30 degrees. In some configurations, the angle is about 27 degrees. However, other configurations are also possible. By way of comparison, the angle of the Simplus® seal is approximately 16 degrees for all seal sizes.

Figure 25:
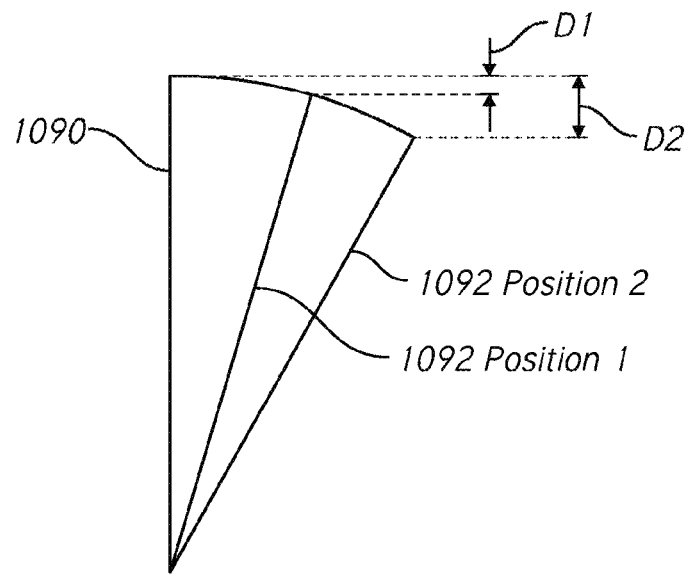
FIG. 25 illustrates a relationship between deflection angle and downward movement of an upper portion of a seal.
Figure 26:
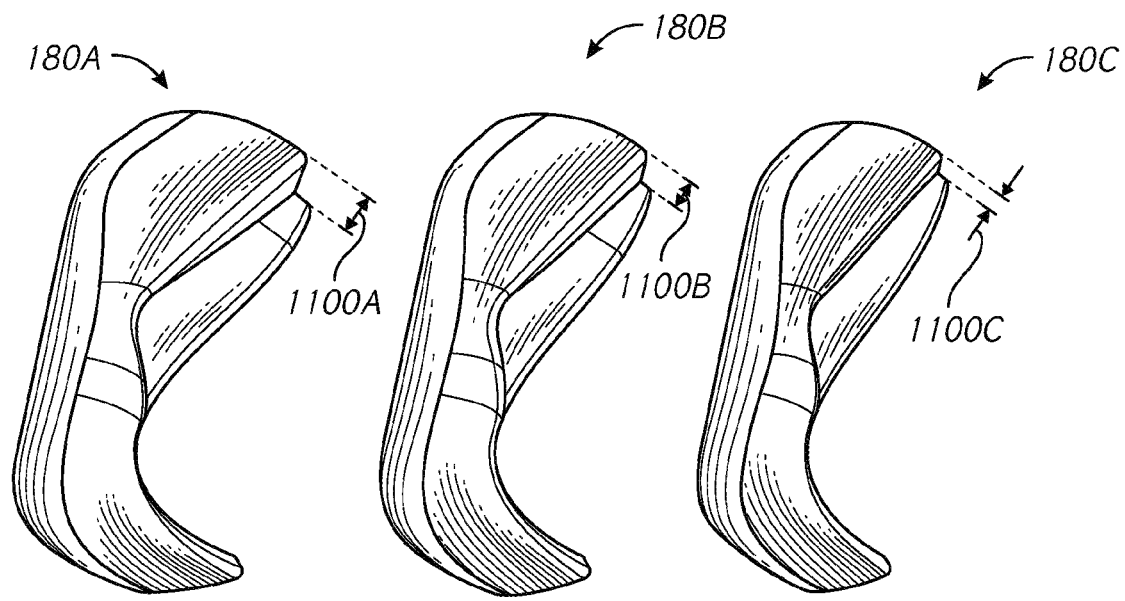
FIG. 26 illustrates several seals of different sizes having different heights of an upper portion of the seal.
Figure 27:
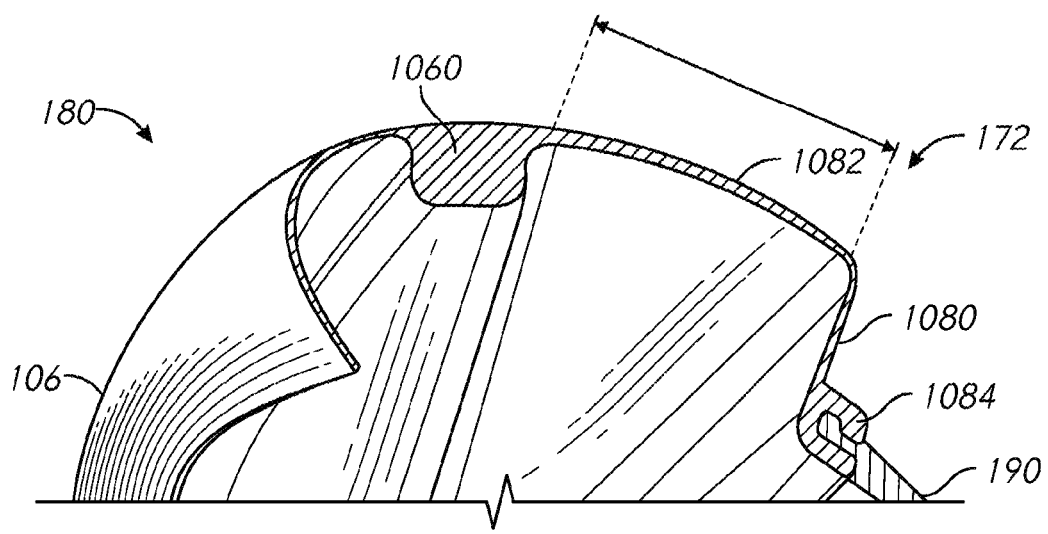
FIG. 27 is a sectional view of an upper portion of a seal, which has a progressively varying thickness in a front wall and a top wall.

FIGS. 25 and 26 illustrate differences in a height of the front wall 1080 between various seal sizes. As the angle of rotation of the upper portion 1002 of the seal 180 increases, the downward movement of the band 1060 or other boundary 1090 increases. For example, FIG. 25 illustrates a difference in downward movement D1 and D2 between a first available maximum deflection angle (represented by 1092 position 1) and a second available maximum deflection angle (represented by 1092 position 2) wherein the second angle is greater than the first angle. The downward movement D2 resulting from the greater maximum deflection angle is substantially greater than the downward movement D1 resulting from the smaller maximum deflection angle. Accordingly, the height of the front wall 1080 in the seal 180 preferably is greater than a height of the front wall in the Simplus® seal. In some configurations, a total length of the reduced stiffness region 172 is also greater in the seal 180 compared to the Simplus® seal.

FIG. 26 illustrates three different sizes of seals 180a, 180b, 180c, which can be the seals of the three cushions modules 110a, 110b, 110c of FIGS. 8 and 9, for example. The seals 180a, 180b, 180c each define a height 1100a, 1100b, 1100c, respectively, of the front walls 1080. The height 1100 can be defined by a distance between the apex 1070 and the uppermost surface of the seal housing 190 or the connecting portion 1084. In some configurations, the heights 1100a, 1100b, 1100c are greater than about 5 mm or greater than about 6 mm. In some configurations, the heights 1100a, 1100b, 1100c are greater than about 7 mm. In some configurations, at least one of the heights 1100a, 1100b, 1100c is greater than about 7.5 mm. In some configurations, the height 1100a is less than one or both of the heights 1100b, 1100c. In some configurations, the height 1100c is greater than one or both of the heights 1100a, 1100b. In some configurations, the height 1100a is smaller than 1100b and the height 1100c is greater than 1100b. In some configurations, the height 1100a is about 7.3 mm. In some configurations, the height 1100b is about 7.6 mm. In some configurations, the height 1100c is about 7.7 mm. For the sake of comparison, a comparable height of the Simplus® seal is about 4.4 mm.

The reduced stiffness region 172 and/or upper portion 1002 of the seal 180 can comprise features that facilitate desirable rolling of the upper portion 1002 of the seal 180. For example, with reference to FIG. 27, at least a portion of the reduced stiffness region 172 comprises a gradually or progressively varying thickness, which preferably increases in a direction from the forward boundary 1092 to the rearward boundary 1090. Preferably, within the progressively varying thickness portion, the thickness is lowest at or toward a forward end of the reduced stiffness region 172 and greatest at or toward a rearward end of the reduced stiffness region 172.

In some configurations, the thickness of one or both of the front wall 1080 and the top wall 1082 gradually or progressively increases in a direction from the connecting portion 1084 toward the band 1060. In the illustrated arrangement, the wall thickness increases progressively from at or near a lower end of the front wall 1080 or the connection portion 1084 to at or near the band 1060 in both the front wall 1080 and the top wall 1082. That is, the rate of change in the wall thickness is consistent between the front wall 1080 and the top wall 1082, despite the transition from one to the other. Such an arrangement allows controlled deformation of the reduced stiffness region 172, such as by allowing the bend point to move in a forward to backward direction as thinner material buckles or bends prior to thicker material buckling or bending. In other configurations, the thickness increase is different between the front wall 1080 and the top wall 1082. For example, the thickness could progressively increase in the front wall 1080 and remain constant or increase at a different rate in the top wall 1082. In other configurations, the thickness of the top wall 1082 could progressively increase and the thickness of the front wall 1080 could be constant or could increase at a different rate than the top wall 1082.

With reference to FIG. 21, an amount of overlap between the seal 180 and the seal housing 190 can vary along a perimeter of or a junction between the seal 180 and the seal housing 190. The dashed line in FIG. 21 indicates an edge of the seal housing 190. The solid line forward (to the right) of the dashed line indicates an edge of the seal 180. The seal 180 edge defines a relatively smoothly curved shape and the seal housing 190 edge defines a less smoothly curved shape. The overlap between the seal 180 and the seal housing 190 can be greater at or near a midsection of the cushion module 110 in a vertical direction relative to other portions of the cushion module 110. The variation in overlap can be to increase the retention of the seal 180 to the seal housing 190 or can simply allow the seal 180 edge to have a desirable aesthetic shape. In some configurations, the portions of increased or relatively large overlap can inhibit or prevent the seal 180 from expanding in a laterally outward direction in response to headgear forces or forces caused by gas pressure within the seal 180. In addition, in at least some configurations, the increased or relatively large overlap and/or the location of the seal housing 190 edge near the hinge axis H provides rigidity at or near the hinge axis H, which can improve the rolling or hinging motion about the hinge axis H.

With reference to FIG. 29, the cushion module 110 is illustrated in a rear plan view, a side view in a first (e.g., neutral) position and a side view in a second (e.g., depressed or fully depressed) position. Similarly, a Simplus® cushion module is illustrated in a rear plan view, a side view in a neutral position and a side view in a depressed position. The rear plan views of FIG. 29 illustrate measuring points at a top of the seal 180 and a bottom of the seal 180 on a vertical center line. In some configurations, a height of the seal 180 is measured between two points located at a mid-point of the sealing surface on the vertical center line. The first point 1200 is located at the nasal bridge region of the seal 180 and the second point 1202 is located at the chin region of the seal 180. The points 1200, 1202 generally correspond to the location on the nasal bridge and chin of the user at which the seal 180 contacts and forms a substantially air tight seal.

A vertical distance or dimension 1204 between the points 1200, 1202 is a significant factor in determining fit of the seal 180 or cushion module 110 to a user. For example, the dimension 1204 is closely related to the Sublabiale-Sellion (SS) dimensions or lengths of the users for which the seal 180 or cushion module 110 will provide an appropriate or desirable fit. In at least some configurations, a substantial difference exists between the dimension 1204 of the seal 180 in the neutral position and the depressed position, which can be a fully depressed position. For example, the dimension 1204 can vary by more than 2 mm between the neutral and the depressed position. In some configurations, the dimension 1204 varies by at least about 4 mm, at least about 5 mm or at least about 6 mm between the neutral and the depressed position. In at least one size or embodiment of the seal 180, the dimension 1204 can vary from about 90 mm to about 84 mm between the neutral and the depressed positions. In other words, the variation of the dimension 1204 is about 6 mm. For the sake of comparison, the Simplus® cushion module varies by 2 mm between a neutral position and a fully depressed position (from about 91 mm to about 89 mm, respectively).

The variation in the dimension 1204 can allow a particular size or embodiment of the seal 180 (or cushion module 110) to fit a wider range of users. For example, the variation in the dimension 1204 can allow a particular size or embodiment of the seal 180 (or cushion module 110) to be deformed or depressed until the dimension 1204 is appropriately sized for the particular user's facial geometry (e.g., SS length). The increased variation in the dimension 1204 can be provided by the greater angular displacement of the upper portion 1002 of the seal 180 as a result of the above-described rolling action, by the increased height of the front wall 1080 or increased length of the reduced stiffness region 172, by other factors or by any combination thereof. In some configurations, a greater variation in the dimension 1204 can be provided, such as at least about 8 mm, at least about 10 mm, at least about 12 mm or more. In some cases, a greater variation is preferred, so long as other performance criteria are not impacted to an undesirable degree. In some configurations, the variation can depend on or vary with the size of the seal 180 or cushion module 110, such as with larger sizes having a greater variation in the dimension 1204 than smaller sizes. For example, the variation can be a percentage of the dimension 1204, such as any percentage covered by the values or ranges disclosed above. In some configurations, the variation in the dimension 1204 can be at least about 5 percent, at least about 6 percent, at least about 6 and ⅔ percent, at least about 8 percent, at least about 10 percent or more between the neutral position and the depressed position.

Gender Based Full-Face Mask Sizes

In some configurations, dimensions of the cushion module 110 and/or seal 180 can be selected based on gender-specific data. For example, in some configurations, gender-specific population data regarding relevant facial features, dimensions or other characteristics can be utilized in the design or sizing of the cushion module 110 and/or seal 180. In some configurations, a first cushion module 110 and/or seal 180 is based on female facial features, dimensions or other characteristics and a second cushion module 110 and/or seal 180 is based on male facial features, dimensions or other characteristics. An interface or mask system or kit comprises a female specific cushion module 110 and/or seal 180 and a male specific cushion module 110 and/or seal 180. The gender specific cushion modules 110 and/or seals 180 can be configured in accordance with any of the cushion modules or seals disclosed herein and can include any feature or combination of features of the disclosed cushion modules or seals. A disclosure of gender-specific considerations follows with reference to FIGS. 30-45.

Figure 30:
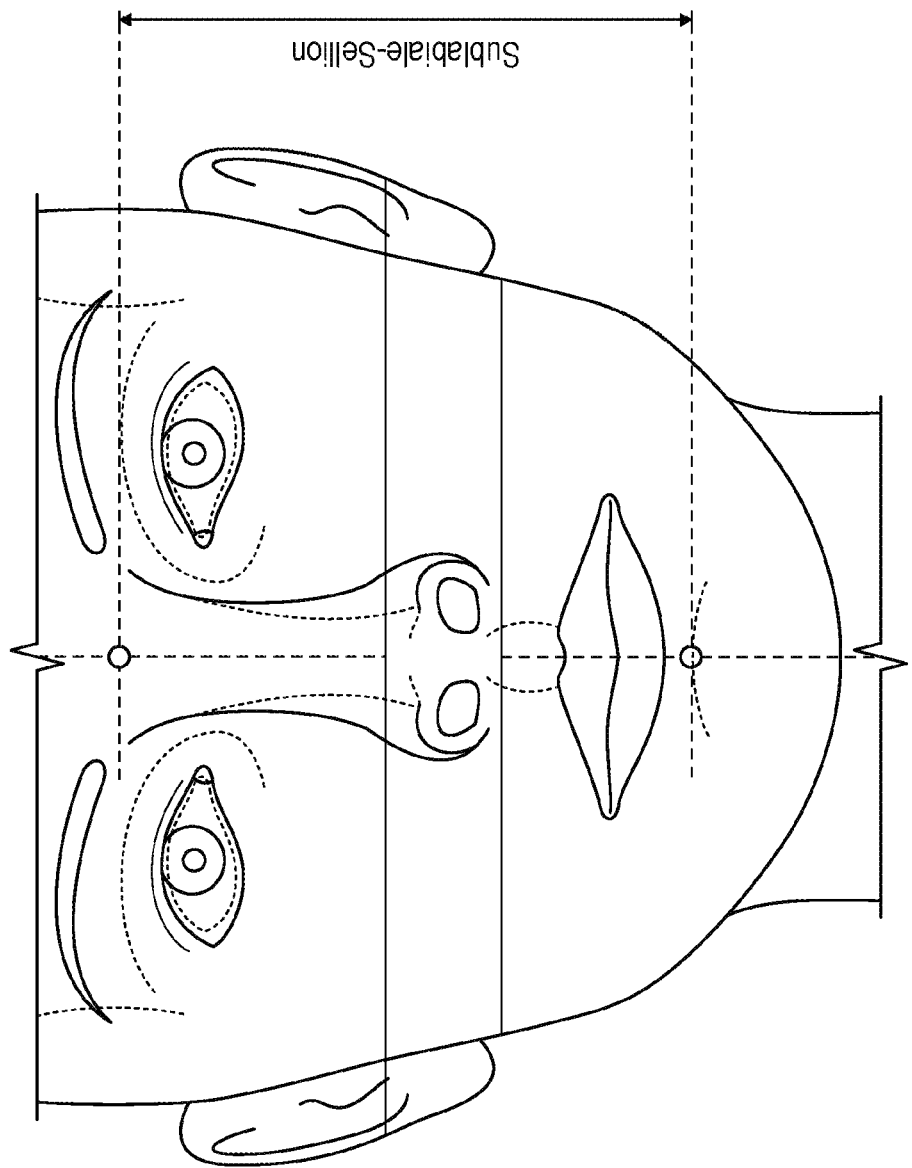
FIG. 30 illustrates landmarks through which the Sublabiale-Sellion (SS) dimension is measured.
Figure 30:
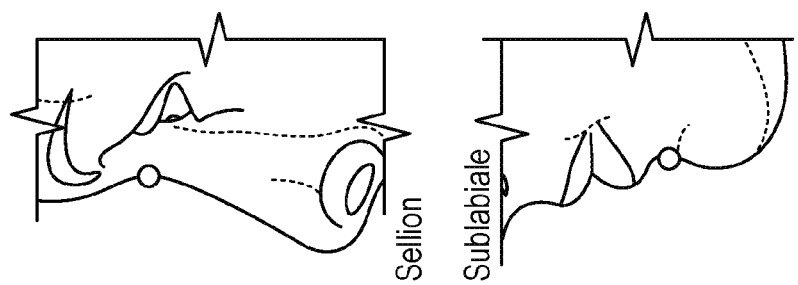
Figure 31:
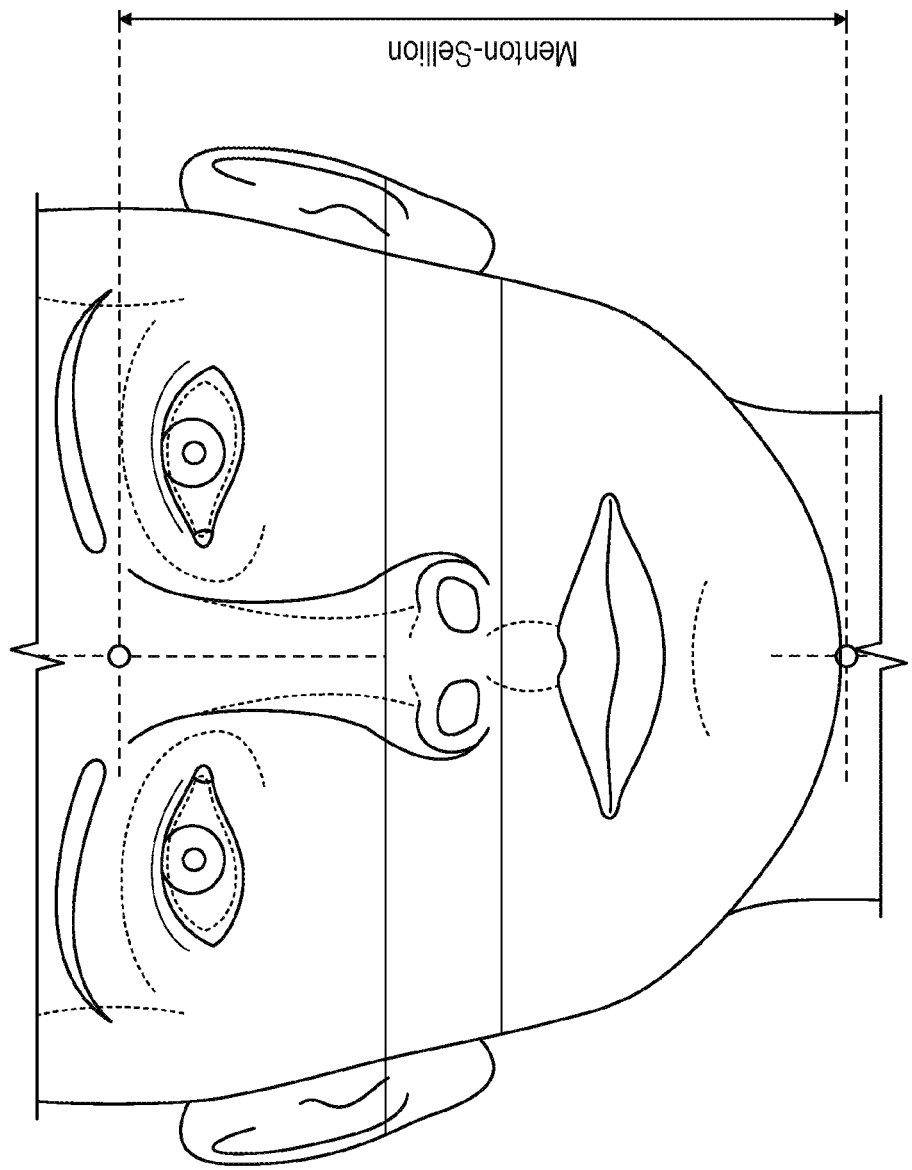
FIG. 31 illustrates the landmarks through which the Menton-Sellion (MS) dimension is measured.
Figure 32:
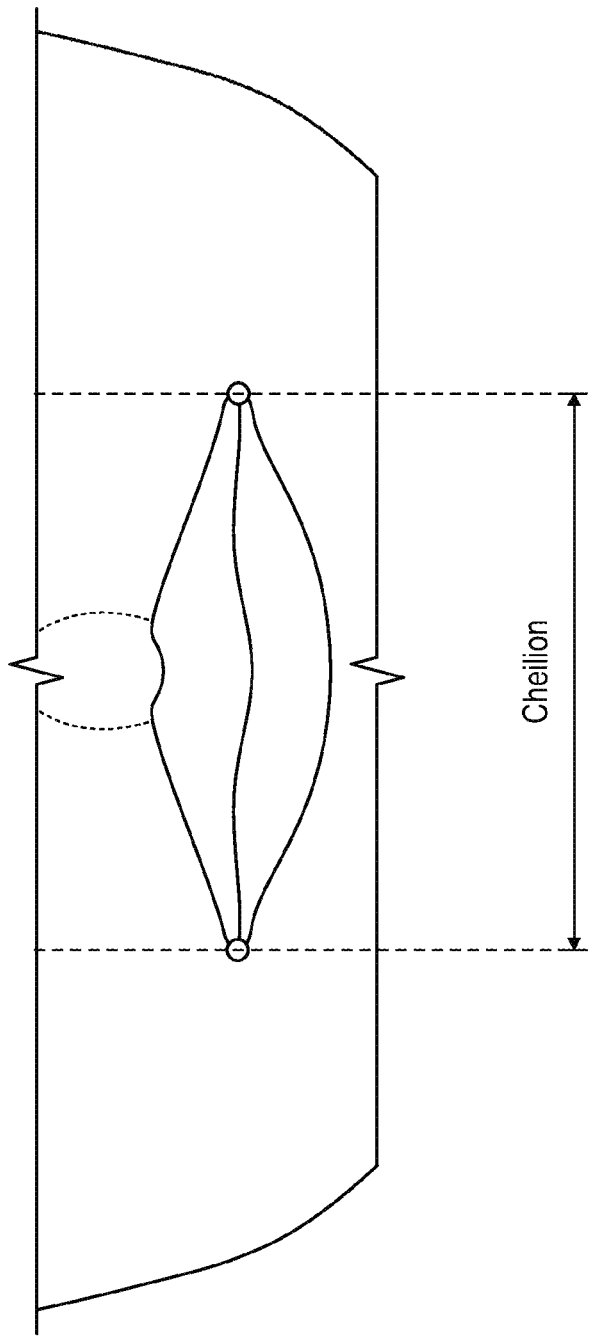
FIG. 32 illustrates the landmarks through which the Cheilion dimension is measured.

FIGS. 30-32 show several anthropometric facial dimensions that are relevant in determining the sizes of full-face respiratory masks. FIG. 30 shows the landmarks through which the Sublabiale-Sellion (SS) dimension is measured. The SS is the dimension from the most indented point under the lower lip to the most indented point of the forehead above the nose and between the eyes. These landmarks form common contact points between a full-face respiratory mask and a patient's face, thus this dimension often corresponds most accurately to the required length of a full-face respiratory mask. FIG. 31 shows the landmarks through which the Menton-Sellion (MS) dimension is measured. The MS is the Dimension from the underneath of the chin to the most indented point of the forehead above the nose and between the eyes. This dimension is commonly used in scientific studies and data sets. The SS dimension can be converted or derived from the MS dimension using difference factors extrapolated from databases that contain data for both dimensions. This enables the size of the data set, to which this disclosure relates, to be increased. FIG. 32 shows the landmarks through which the Cheilion dimension is measured. The Cheilion dimension is the lip length or mouth width between the corners of the mouth.

There are a number of studies relating to respiratory mask anthropometrics, referred to in the body of this specification, they are as follows (and are hereby incorporated by reference herein in their entireties):
1. Zhuang Z, Landsittel D, Benson S, Roberge R, Shaffer R. Facial anthropometric differences among gender, ethnicity, and age groups. Ann Occup Hyg. 2010 June; 54(4): 391-402.
2. Zhuang Z, Bradtmiller B. Head-and-face anthropometric survey of U.S. respirator users. J Occup Environ Hyg. 2005 November; 2(11):567-76.
3. Han D H. Fit factors for quarter masks and facial size categories. Ann Occup Hyg. 2000 May; 44(3):227-34.
4. Oestenstad R K, Dillion H K, Perkins L L. Distribution of faceseal leak sites on a half-mask respirator and their association with facial dimensions. Am Ind Hyg Assoc J. 1990 May; 51(5):285-90.
5. Liau Y H, Bhattacharya A, Ayer H, Miller C. Determination of critical anthropometric parameters for design of respirators. Am Ind Hyg Assoc J. 1982 December; 43(12): 897-9.
6. FPH OSA Interface Anthropometric Database 2014.

Figure 33:
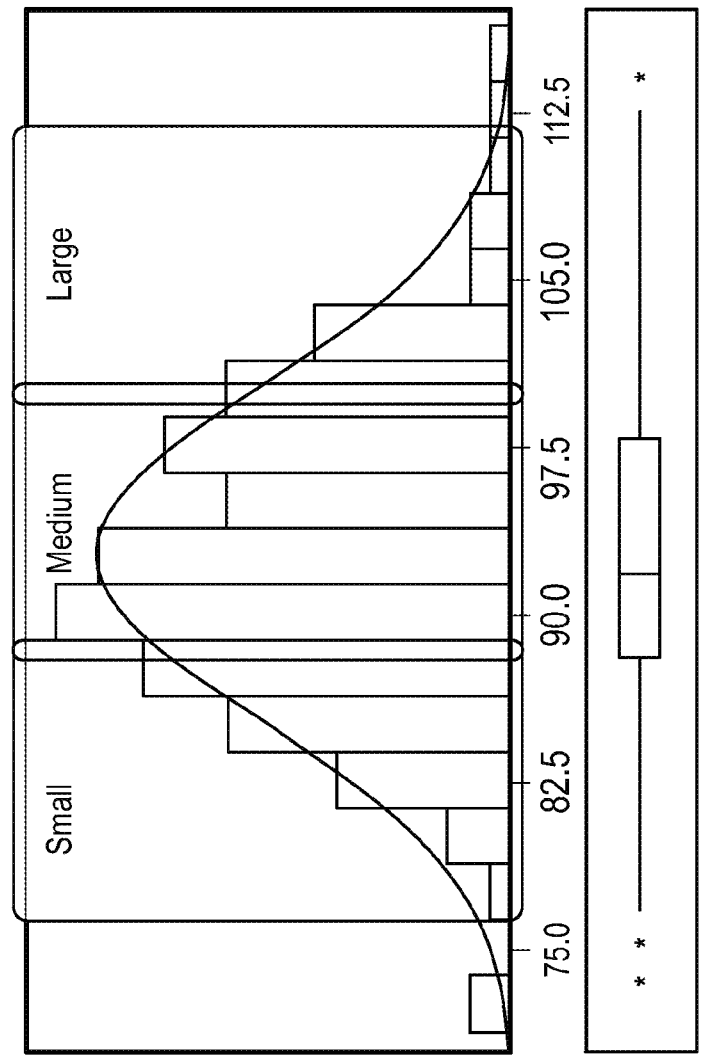
FIG. 33 illustrates a distribution plot of SS lengths with an example of a traditional respiratory mask size ranges overlaid.

FIG. 33 shows a distribution plot of SS lengths with an example of a traditional respiratory mask size ranges overlaid. It can be seen that the SS length range is split over three equal size ranges (small, medium and large) that have a degree of overlap. It is intended that a small mask size will fit people with a SS length between 76 mm and 88.3 mm, a medium mask size will fit people with a SS length between 88 mm and 100.3 mm, and a large mask size will fit people with an SS length between 100 mm and 106.15 mm. Since the medium size is intended to fit people with an SS length that falls within the central third of the distribution range it is apparent that more people will fit a medium size mask than will fit a small or large size mask.

Figure 34:
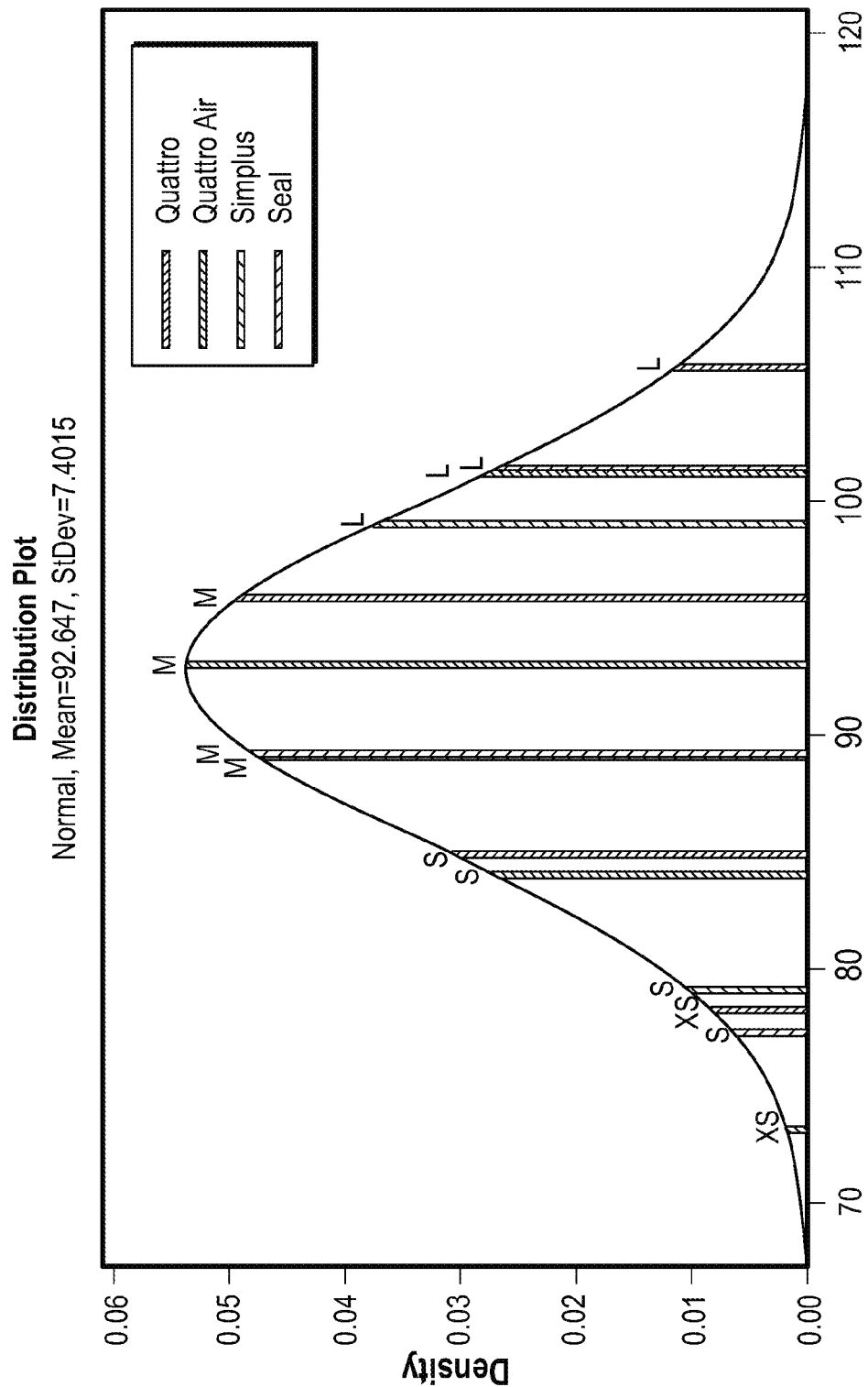
FIG. 34 illustrates a distribution plot of SS lengths with a comparison of the mask lengths for each size of several mask ranges overlaid.

FIG. 34 shows a distribution plot of SS length with a comparison of the mask lengths for each size of several mask ranges, overlaid. The Quattro and Quattro Air mask ranges by Resmed™ are compared to the Simplus mask by Fisher & Paykel Healthcare Ltd. and the cushion module 110/seal 180 disclosed herein primarily with respect to FIGS. 1-29 (hereinafter "seal 180"). The Quattro and Quattro Air masks are both available in a range of four sizes including extra small (XS), small(S), medium (M) and large (L). The Simplus mask ranges and seal 180 both have three sizes including S, M, and L. It can be seen that the mask lengths are spread over a wide range of the distribution, however the size groups are clustered together. The XS sizes for the Quattro and Quattro air in a similar range to the S sizes of the Simplus mask and seal 180, and are clustered at the lower end of the length range. The M sizes for all of the mask ranges fall are clustered near the center of the distribution and the L sizes for all of the mask ranges are clustered near the upper end of the length range. The S sizes for the Quattro and Quattro Air a positioned between the XS/S cluster and the M cluster. Generally speaking, the Resmed masks are larger than the Fisher and Paykel Healthcare masks. This grouping of sizes suggests that the traditional techniques for determining mask sizes were based around providing an M size mask that will fit the majority of the population, and then providing the other sizes to capture the remainder of the population. The S and L sizes of each mask range are approximately equally spaced from the M size.

Figure 35:
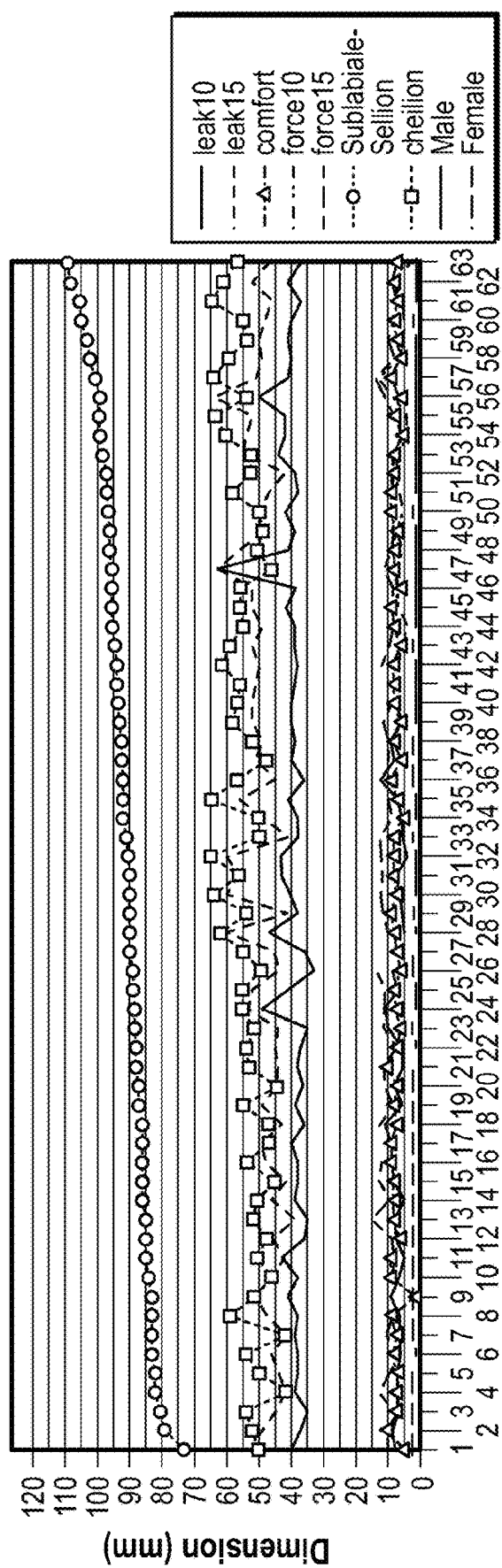
FIG. 35 is a graph of plots that demonstrate the correlation between the SS length dimension and the Cheilion dimension.
Figure 36:
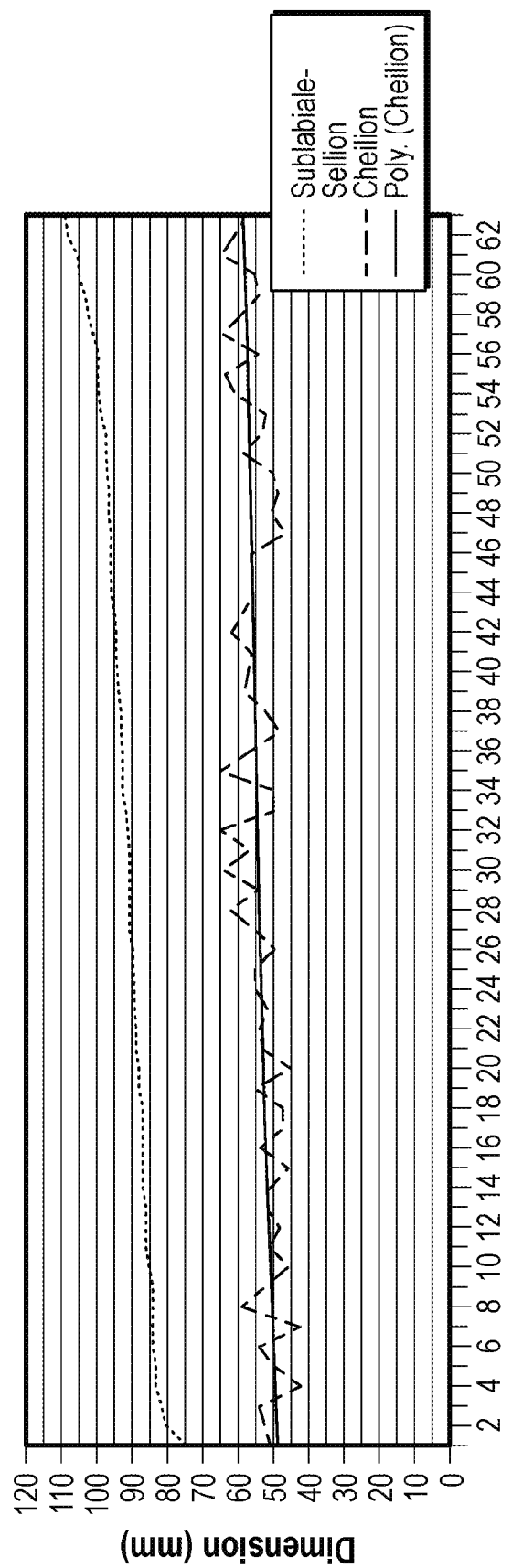
FIG. 36 is a graph of plots that demonstrate the correlation between the SS length dimension and the Cheilion dimension, including a polynomial curve that has been fitted to the Cheilion dimension data set.

FIGS. 35 and 36 show plots that demonstrate the correlation between the SS length dimension and the Cheilion dimension. The dataset has been sorted in order of increasing SS length as shown by the uppermost line with circular point markers in FIG. 35 and the uppermost line in FIG. 36. Whilst there is some variation in the correlation between SS length and the Cheilion dimension from person to person, it can be seen in FIG. 35 that there is a general upwards trend in the Cheilion dimension as SS length increases. FIG. 36 shows this trend more clearly through a polynomial curve (the lower smooth line) that has been fitted to the Cheilion dimension data set. It can be generally stated that the greater the SS length the greater the Cheilion dimension will be.

In a Meta-analysis of the respirator mask anthropometric literature, Liau5 et al 1982, showed mouth width as a critical anthropometric parameter to mask fit. Oestenstad4 et al 1990, found gender accounted for 71% of differences in facial dimensions.

Figure 37:
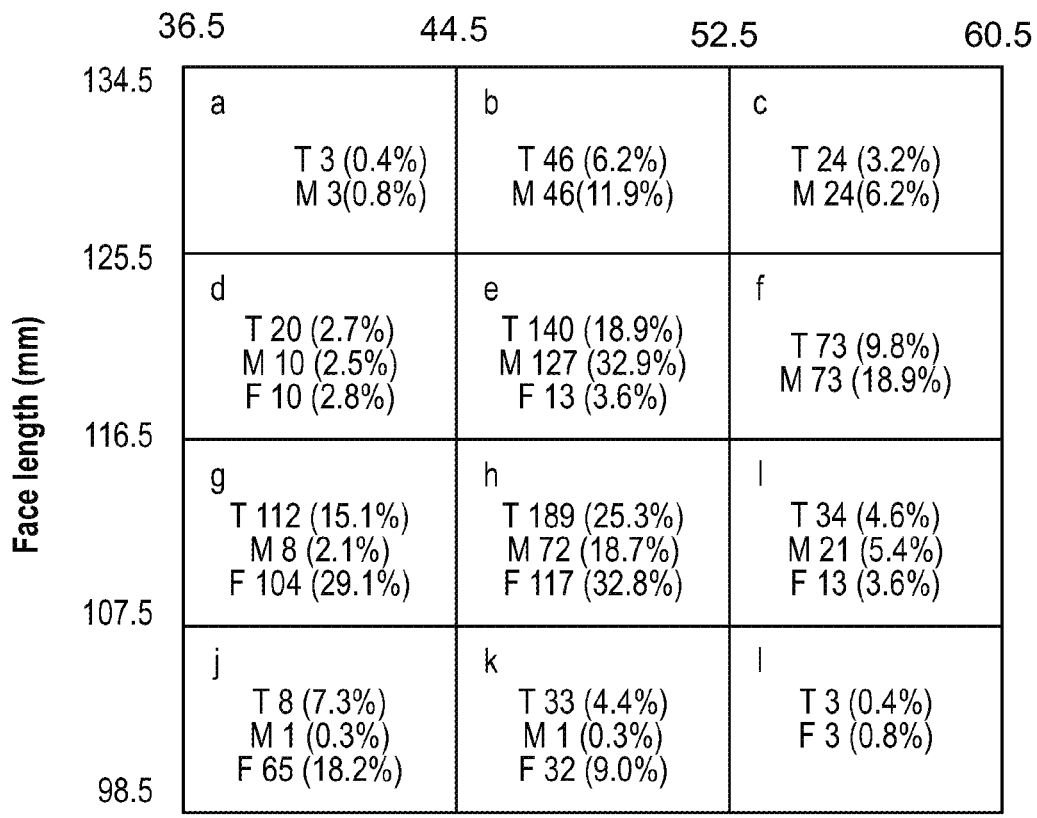
FIG. 37 is a graph of data from the Han3 2000 study.

Han3 2000, in a study of 778 people found that males have longer faces and wider lips than females, as shown in FIG. 37. Zhuang2 et al 2005, sited lip length as being of practical importance in mask sizing.

Zhuang1 et al 2010 suggests that gender is a critical variable in determining mask fit, more so than ethnicity. He stated that the overall size of female faces is smaller than males and that females have shorter narrower faces. The statistically significant difference between male and female facial anthropometric dimensions was P<0.05.

The data from the Zhuang1 study, n=4140, was obtained for further analysis. The Zhuang1 data was converted from Menton-Sellion length to Sublabiale-Sellion length using difference factors extrapolated from the FPH Anthropometric Database6 with contains data for both measurements.

Figure 38:
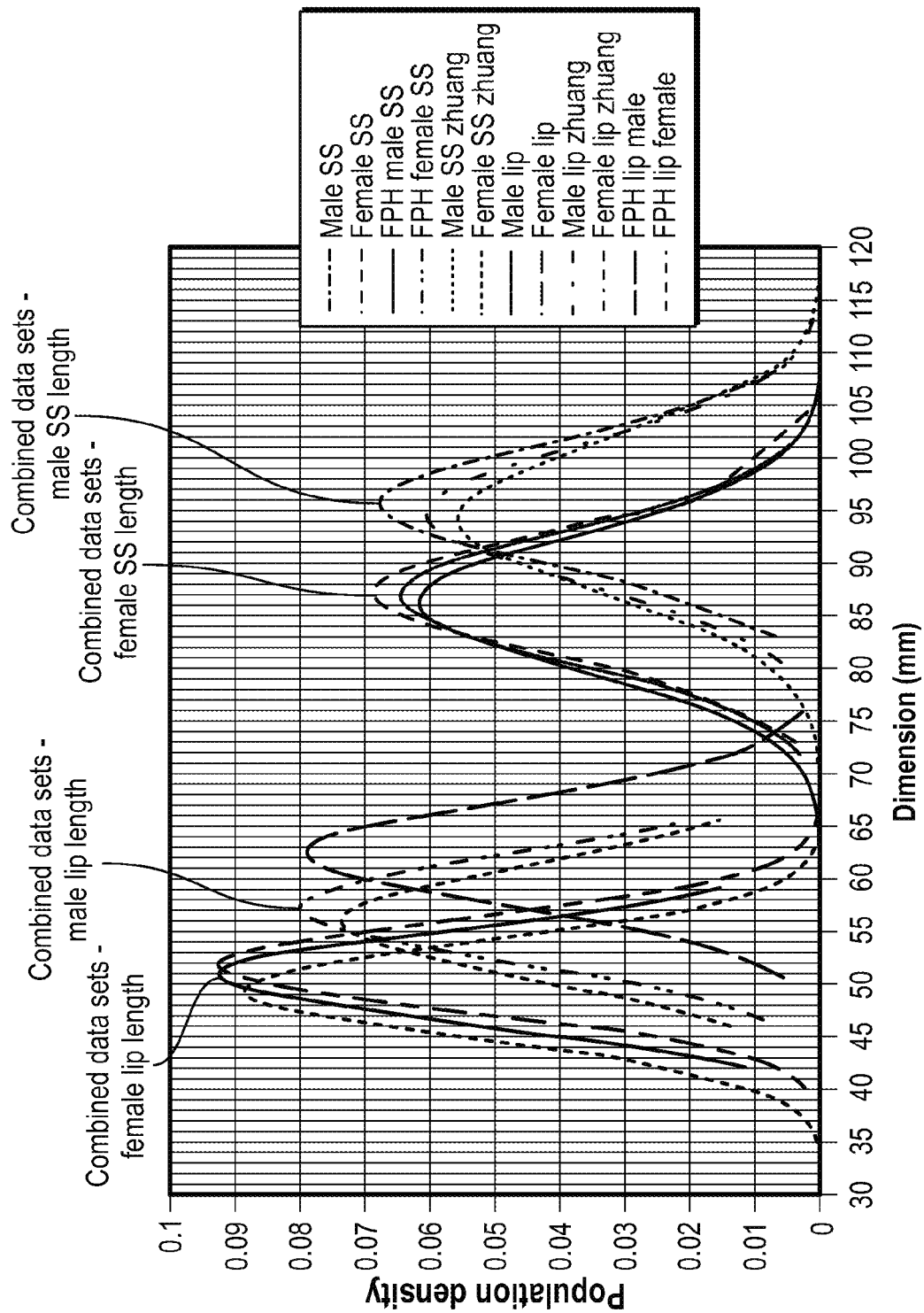
FIG. 38 illustrates a distribution plot of SS length and lip length for the FPH6 and Zhuang1 along with a combined dataset.

FIG. 38 is a distribution plot of SS length and lip length (Cheilion dimension) for the two data sets (FPH6 and Zhuang1) along with a combined dataset. The X axis shows the facial dimension in mm and the Y axis shows the density of the population. The data sets have been sorted into female and male sets. It can be seen that distributions of the male and female data sets overlap for both SS length and lip length but are centered around different medians, such that, as expected, females are smaller than males. It can be seen, from the overlap and alignment of medians in the distributions, that there is substantial correlation between the distribution of SS length between the two data sets. The correlation of lip length distributions between data sets is not as strong but there is still significant overlap and the difference between females and males exists within both datasets.

Further distributions are shown on this plot for a dataset wherein the data from Zhuang1 and FPH6 have been combined to provide a larger sample size. From these distributions it can be seen that the combined dataset female lip length has a range of about 17 mm. The combined dataset male lip length has a range of about 18.5 mm. The combined dataset female SS length has a range of 31 mm, and the combined dataset male SS length has a range of 26 mm. It can be seen that the variation in SS length is greater for both female and males than the variation in lip length. Males tend to have greater variability in lip length than females.

From analysis of these plots it appears that if one mask size could successfully and comfortably fit a Sublabiale-Sellion range of 24 mm and a lip length or Cheilion range of 14 mm then over 95% of the population could be fit with two mask sizes, one for each gender. This is advantageous in that is reduces the manufacturing costs associated with producing multiple sizes of the same mask. It also makes selecting the correct size for a patient easier as there are fewer mask sizes to choose from. Being gender based also makes size selection easier.

Based on the above disclosure, an aspect of the present disclosure involves a full-face mask sizing system or kit that comprises of only two mask sizes, each targeted a either female or male patients. Each of the sizes is defined to fit a range of SS lengths and lip lengths that correspond to approximately 95% of either the male or female population. In some configurations, the ranges will overlap such that males with smaller facial geometry and females with larger geometry may use either of the mask sizes.

Figure 39:
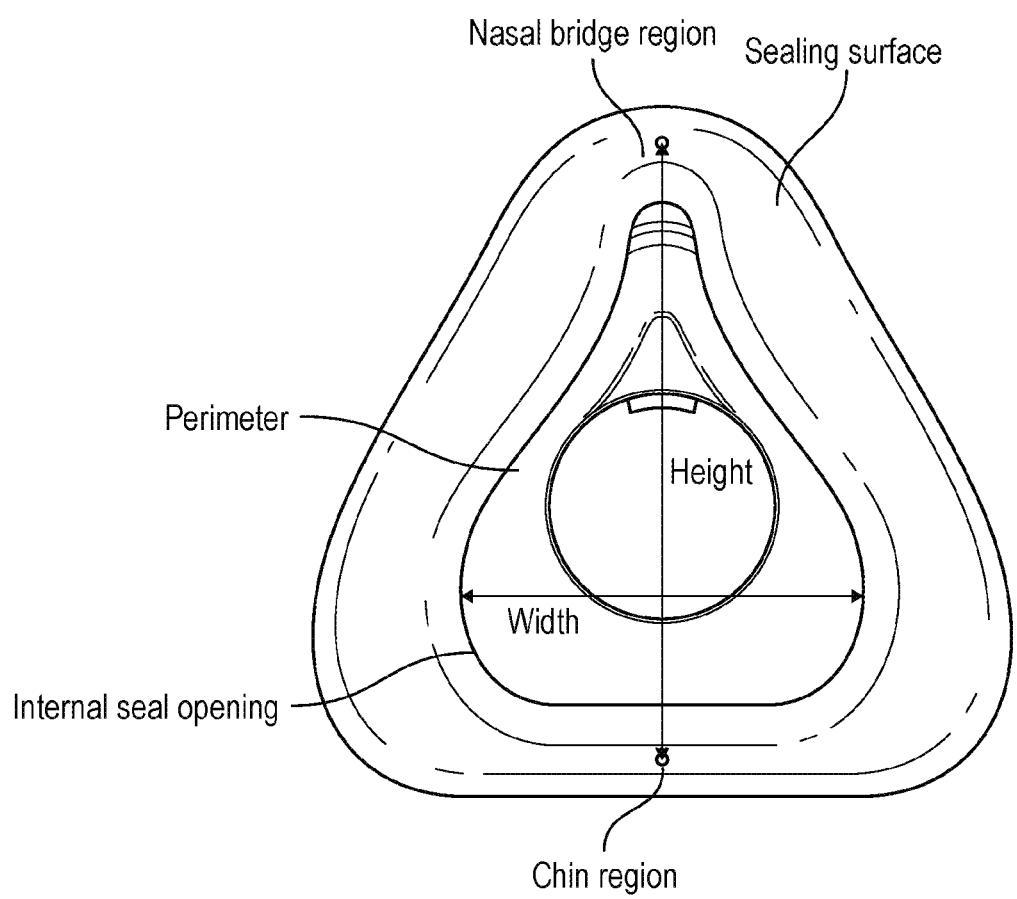
FIG. 39 illustrates a rear view of a full-face respiratory mask seal.

FIG. 39 shows a rear view of a full-face respiratory mask seal. The significant dimensions in determining mask sizes are labelled. The height of the mask seal is measured between two points located at a mid-point of the sealing surface. The first point is located at the nasal bridge region of the seal cushion, and the second point is located at the chin region of the seal cushion. This dimension corresponds with the location on the nasal bridge and chin, of the patient, where the mask seal will or is likely to contact and form a substantially air tight seal. This dimension is closely related to SS length. The width of the mask seal is measured between two lateral points on the perimeter of the internal seal opening. This dimension relates to lip length or the Cheilion dimension. It is desirable, in terms of comfort and seal, that the internal seal opening does not overlap the corners of the patient's mouth.

Figure 40:
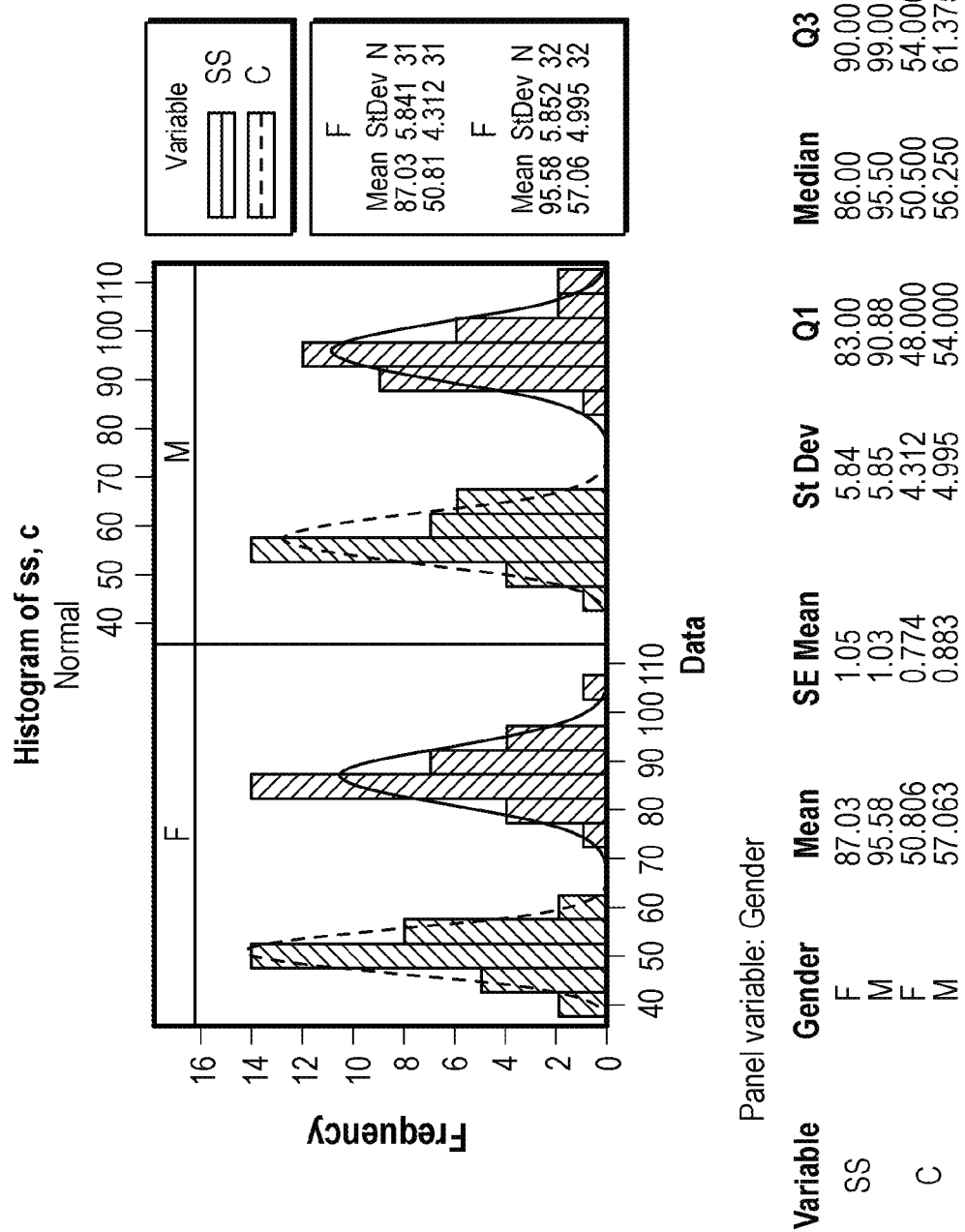
FIG. 40 is a histogram illustrating the difference in SS length and Cheilion length between genders.

An analysis of variance study (ANOVA) was completed using the FPH6 dataset to analyze the difference in SS length and Cheilion length between genders. A histogram of the results is shown in FIG. 40. It can be seen that females have a median SS length of 86 mm and males have a median SS length of 95.5 mm. Females have a median Cheilion length of 50.5 mm and males have a median Cheilion length of 56.25 mm. These medians can be used to determine the height and width of the two gender based mask sizes.

In some configurations, it is desirable that the nasal bridge region on the mask seal sits slightly below the Sellion of the patient. This is so that the mask seal does not sit too close to the patient's eyes and cause discomfort. It is also easier to achieve an airtight seal between the mask seal and the patient's face at a location slightly below the Sellion. A distance of 5 mm below the Sellion has been found to be effective in terms of comfort and seal. As such, in at least some configurations, the height of the gender bases sizes is based upon or determined by subtracting 5 mm from the median SS length. In at least some configurations, the width of the gender based mask sizes is based on or is the same as the median Cheilion length for each gender.

Figure 41:
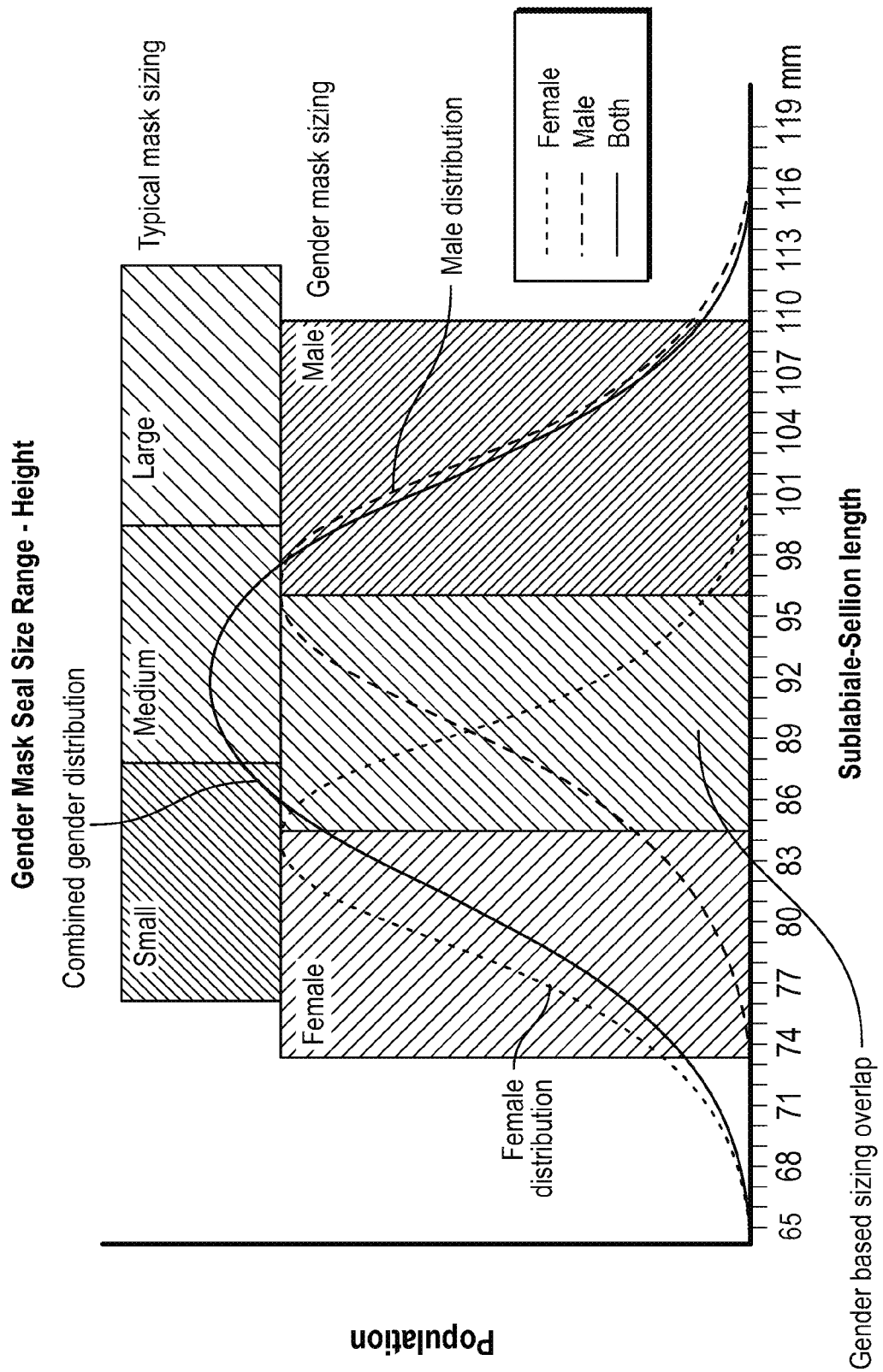
FIG. 41 is a graph comparing SS length a traditional mask sizing system to the male and female based sizing.
Figure 42:
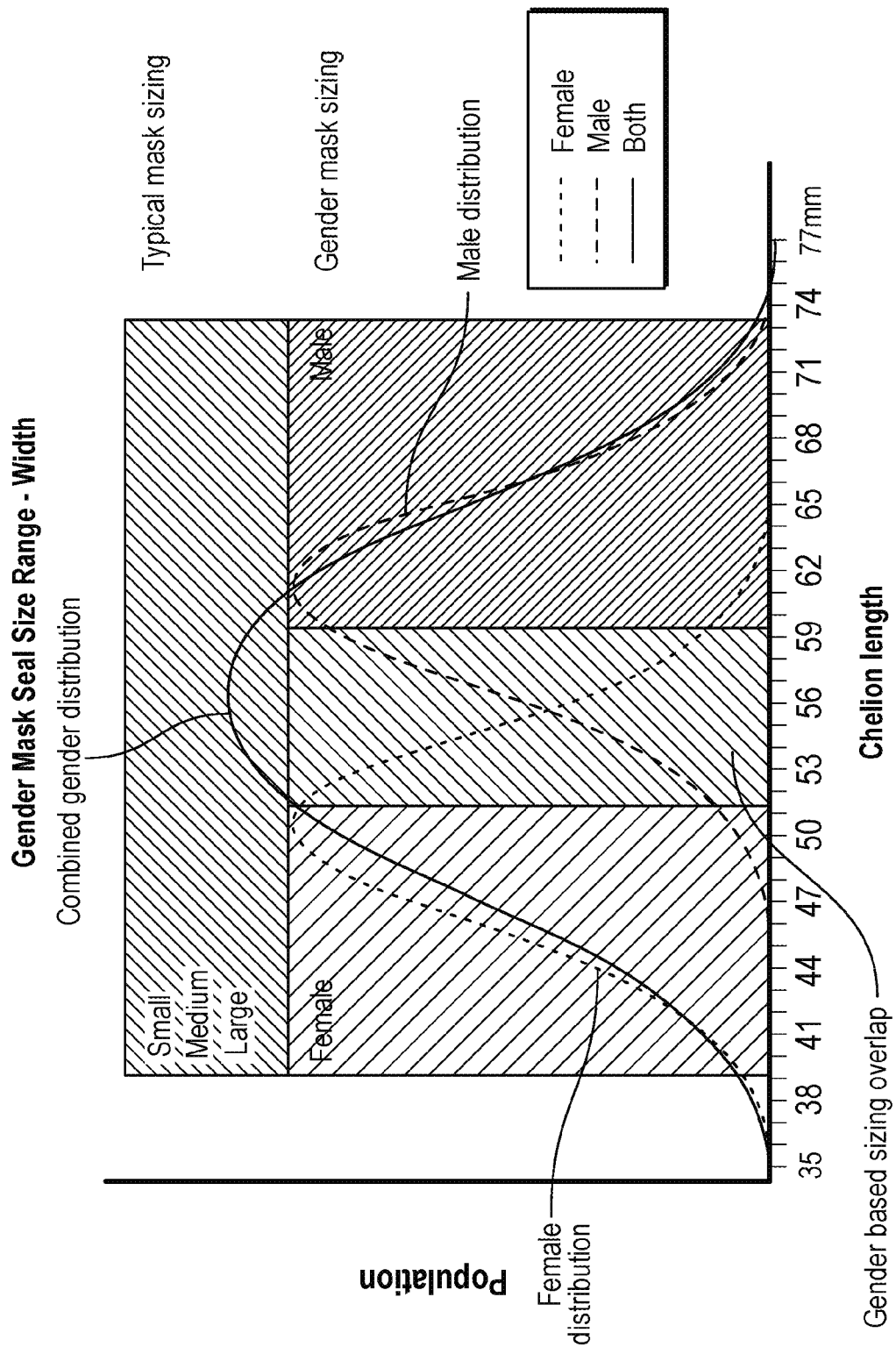
FIG. 42 illustrates is a graph comparing Cheilion length of a traditional mask sizing system to the male and female based sizing.

FIGS. 41 and 42 compare a traditional mask sizing system to the male and female based sizing of the present disclosure. In FIG. 41, three SS length distributions are shown; one each for female and male and a third combined gender distribution where the female and male populations have been combined. Above the distribution plots is a series of three shaded boxes represent the height ranges of typical (traditional) mask sizing wherein there are three sizes including small, medium and large. It can be seen that the medium size height range is substantially aligned with the distribution plot for the combined female and male SS lengths. Below the shaded boxes of the typical mask sizing are a further two shaded boxes that represent the range of SS lengths that the proposed female and male mask sizes will fit. Each of the female and male sizes is configured to fit a wider range of SS lengths than each of the sizes of typical (traditional) masks. The female and male mask sizes are aligned with the medians of the corresponding populations. It can be seen that there is significant overlap between the female and male sizes, such that people with SS lengths that fall near the middle of the combined gender distribution, or between 84.5 mm and 96 mm, may fit both mask sizes.

FIG. 42 shows a similar comparison in relation to the width of traditional mask sizes and of the female and male sizes of the present disclosure. Three distribution plots are shown, one each for the female and male Cheilion lengths and a third combined gender distribution. Above the distribution plots is a single shaded box that represents the width range of typical (traditional) mask sizes. It is apparent that there is often little to no variation in the width of the three mask sizes (small, medium and large). Each of the mask sizes is intended to fit the majority of the Cheilion length range of the combined gender distribution. Below this shaded box is a further two shaded boxes representing the female and male sizes of the present disclosure. The female and male mask sizes are approximately aligned with the medians of the corresponding populations. It can be seen that there is significant overlap between the female and male sizes, such that people with Cheilion lengths that fall near the middle of the combined gender distribution, or between 51.5 mm and 59.5 mm, may fit both mask sizes. In contrast to the typical mask sizes, the female and male mask sizes preferably have different widths.

FIGS. 41 and 42 show that based on the ANOVA study previously described, it is possible to cover the majority of the combined gender distribution ranges, for both SS length and Cheilion length, with two mask sizes.

Figure 43:
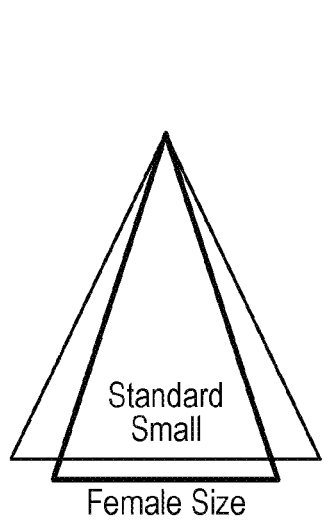
FIG. 43 illustrates height and width dimensions of the present female and male mask sizes compared to small, medium and large mask sizes.
Figure 43:
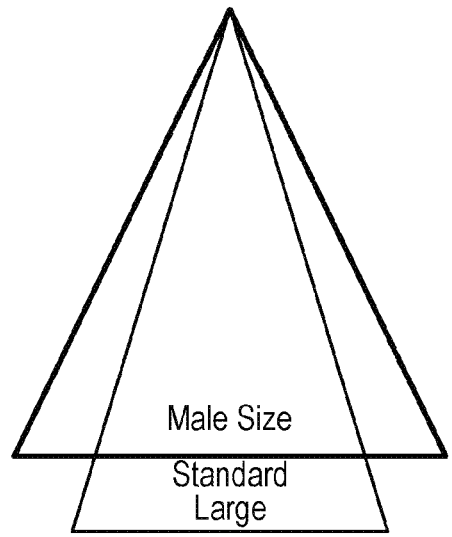
Figure 43:
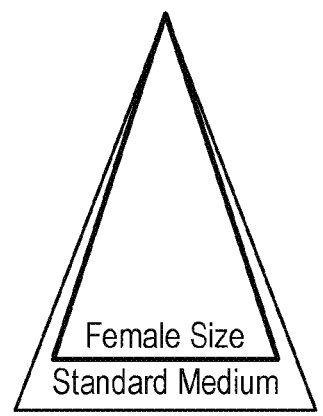
Figure 43:
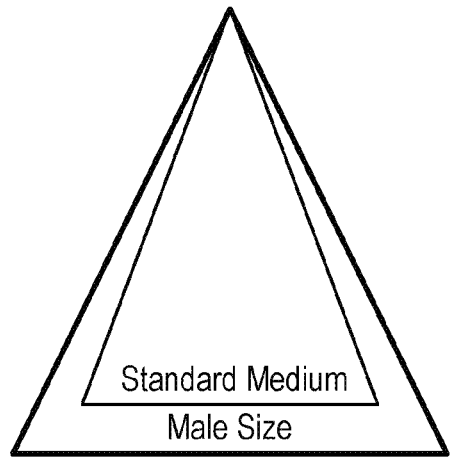

FIG. 43 compares height and width dimensions of the present female and male mask sizes with the typical small, medium and large mask sizes. The height and width of the masks are represented by a series of isosceles triangles, wherein the base length of the triangles correspond to the width of the mask and the height of the triangles corresponds to the height of the mask. Further, the height dimensions are measured between midpoints of the cushion in the chin and nasal bridge regions, and the width is measured horizontally between the edges of the cushion. Even further, in some configurations, the cushion is positioned approximately 5 mm below the Sellion of the user. The female size (based on the ANOVA results) has a height of about 81 mm and a width of about 50.5 mm. The male size has a height of about 90.5 mm and a width of about 56.5 mm. The width of the female size fits a max Cheilion length of 65 mm measured between midpoints of the cushion. The width of the male size fits a max Cheilion length of 76 mm measured between midpoints of the cushion.

In the upper left comparison it can be seen that the female size is taller and narrower than the standard small size, which has a height of 77 mm and a width of 54 mm. The lower left comparison shows that the female size is shorter and narrower than the standard medium size, which has a height of 89 mm and a width of 55 mm. The lower right comparison between the male size and the standard medium shows that the male size has a greater height and width than the standard medium. The upper right comparison shows that the male size is shorter and wider than the standard large size, which has a height of 100 mm and a width of 55 mm. When comparing the width of the female size (50.5 mm) to the standard small, medium and large sizes (54 mm, 55 mm, and 55 mm, respectively), it should be understood that the width across the opening can be narrower than the width of a user's mouth and the mask will still seal. This is because the sealing point of the cushion is offset from the edge of the opening and positioned within the width of the cushion. As a result, for users having a larger mouth width, the cushion will overlap the corners of their mouth and form a seal immediately adjacent to the corners of their mouth. For users with smaller mouth widths, the cushion will seal further away from the corners of their mouth.

Further, when comparing the difference in height and width between the standard small, medium and large sizes, the standard medium size is 1 mm or 1.8% larger in width and 12 mm or 15.6% larger in height than the standard small size. The standard large size is 0 mm or 0% larger in width and 11 mm or 12.4% larger in height than the standard medium size. In other words, the difference between small to medium sizes and medium to large sizes is mostly in height. In comparison, the male size is 6 mm or 11.9% larger in width and 9.5 mm or 11.7% larger in height than the female size. As such, the difference in width between female to male sizes is much larger than between small, medium, and large sizes (i.e., 6 mm for female to male versus 1 mm for small to medium and 0 mm for medium to large). In addition, the difference in height between female to male sizes is slightly less than between small, medium and large sizes (i.e., 9.5 mm for female to male versus 12 mm for small to medium and 11 mm for medium to large). In some configurations, the difference in height between the female size and the male size may be equal to or less than 9.5 mm or 11.7%. Further, in some configurations, the height and width of the male and female sizes may be within a range of ±2.5 mm of the disclosed dimensions. Accordingly, when considering the variance of ±2.5 mm, the width of the male size may be as little as 1 mm or 1.9% larger to as much as 11 mm or 22.9% larger in width than the female size. The height of the male size may be as little as 4.5 mm or 5.4% larger to as much as 14.5 mm or 18.5% larger in height than the female size. Preferably, the male and female sizes are within a range of ±1 mm of the disclosed dimensions.

Figure 44:
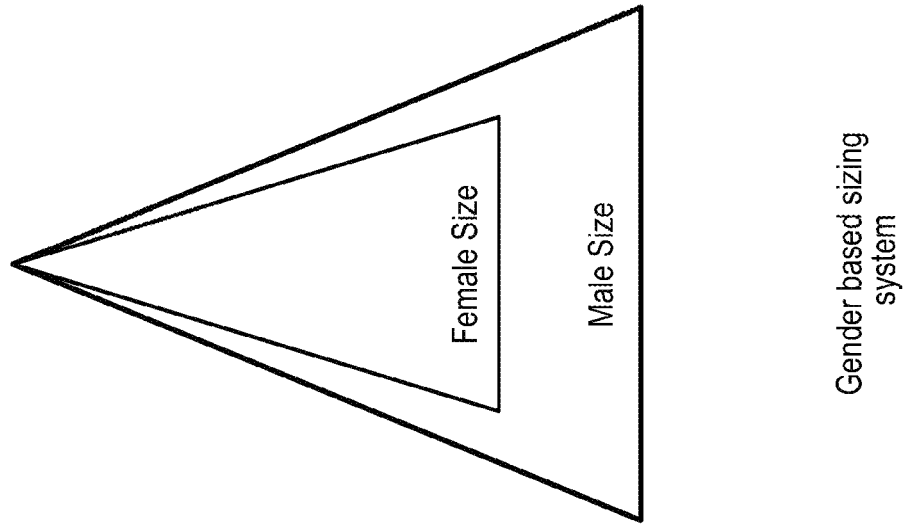
FIG. 44 illustrates heights and widths of each mask size within each of the sizing systems for comparison.
Figure 44:
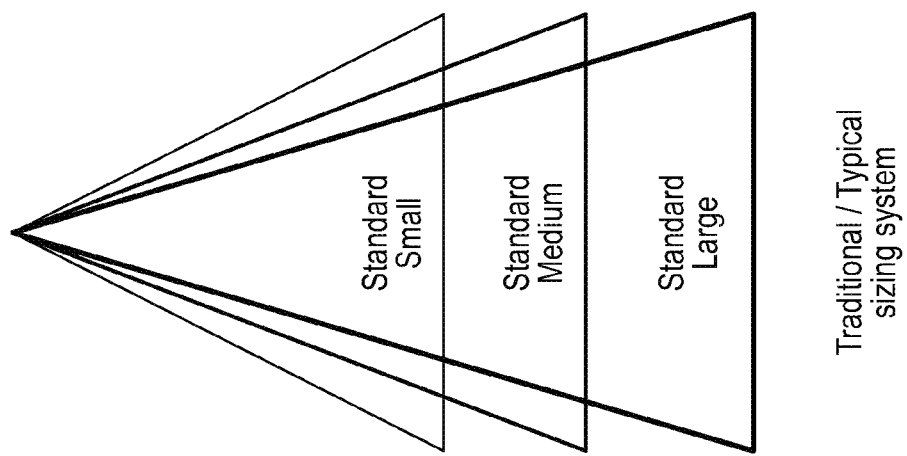

Even further, when comparing the width versus the height of the standard small, medium and large sizes, the width of the standard small size is 70.1% of the height of the standard small size. The width of the standard medium size is 61.8% of the height of the standard medium size. The width of the standard large size is 55.0% of the height of the standard large size. Accordingly, since only the height increases while the width remains relatively unchanged between the small, medium and large sizes, the proportion of the width versus the height decreases from small to large sizes. In comparison, when comparing the width versus the height of the female size, the width of the female size may be 62.3% of the height of the female size, and the width of the male size may be 62.4% of the height of the male size. Females have shorter and narrower faces than males but have similar width versus height proportions as males. Accordingly, with the greater difference in width and smaller difference in height change between the female and male sizes, the proportion or percentage of the width versus the height remains similar between the female and male sizes. When considering the variance of ±2.5 mm, the width of the female size may vary between 57.5% to 67.5% of the height of the female size, and the width of the male size may vary between 58.1% to 67.0% of the height of the male size. In some configurations, the male size and the female size may have equal width versus height proportions. That is, a percentage of the width relative to the height of the male size may be equal to a percentage of the width relative to the height of the female size. In other configurations, FIG. 44 compares how the heights and widths of each mask size vary within each of the sizing systems. Within the traditional/typical sizing system it can be seen that the width of the mask remains substantially the same whilst the height varies. In the gender based sizing system both height and width vary.

Figure 45A:
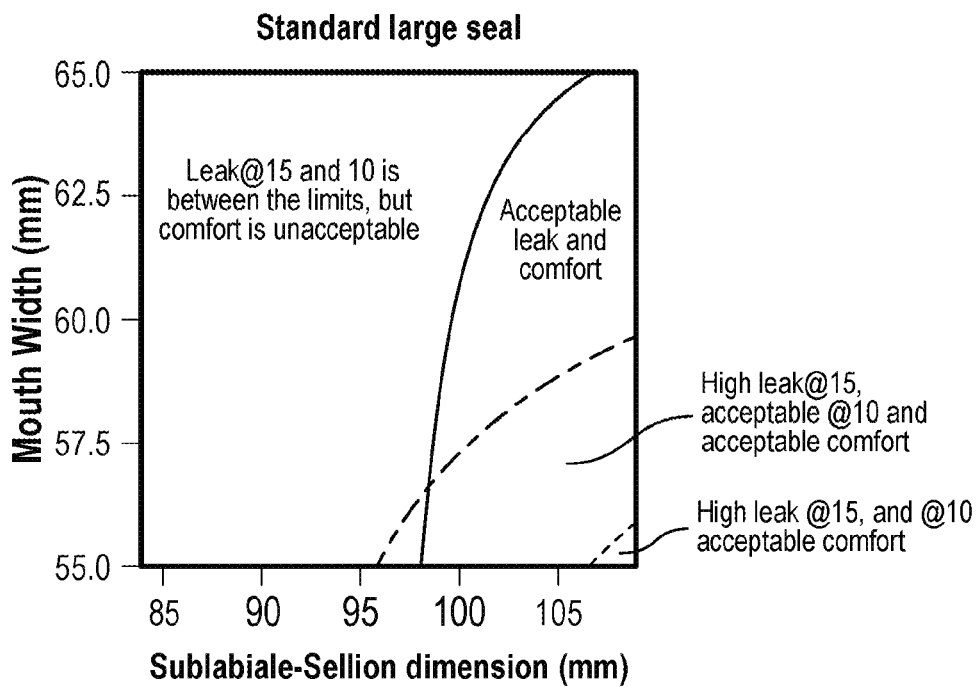
FIG. 45A is a contour plot of a standard large seal for a range of SS dimensions and Cheilion dimensions.
Figure 45B:
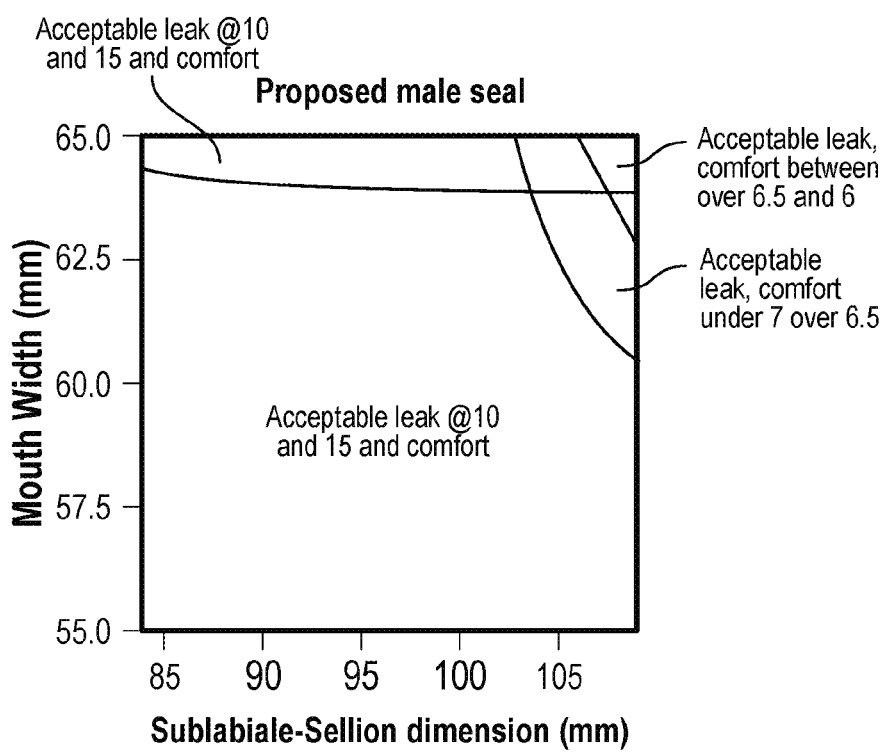
FIG. 45B is a contour plot of a male size seal for a range of SS dimensions and Cheilion dimensions.

Determining Effectiveness of Gender Based Sizing:

FIGS. 45A and 45B are contour plots that show the results of a design of experiment (DOE) study that was conducted to determine the effect that mask seal size has on patient comfort and leak rates for patients with a range of SS dimensions and Mouth widths (Cheilion dimensions). It can thus be determined whether a two size gender based mask sizing system is effective.

A DOE study was carried out using 4 males with mouth width and Sublabiale-Sellion dimensions at the 4 corners of the male size population for mouth width and Sublabiale-Sellion height. These four individuals cover a range of 95% of the male population for these two dimensions which are significant for mask fit.

The DOE study had 3 repetitions and 2 replications to increase the correlation power of the comfort and leak values.

Method:
1. The participant's correct mask fit was determined using CPAP pressures of 10 cm-$H_2O$ and 15 cm-$H_2O$ and adjusting headgear tension at these pressures so that there was minimal leak. 10 cm-$H_2O$ is the $90^{th}$ percentile pressure and 15 cm-$H_2O$ is the $98^{th}$ percentile pressure prescribed to OSA patients.
2. Headgear clips that incorporate tension sensors were used at each of the four headgears to mask frame connection points to determine headgear tension. Each of the four sensor force values recorded.
3. Leak was measured using a flow sensor to check comparative leak values. The participant was asked "is leak annoying?"
4. Fit was determined as the minimum headgear tension where minimal leak occurred; <10 LPM leak and no feeling of major leak by the participant or investigator. This was a mean of 3 headgear clip sensor readings. The masks were loosened and retightened and measurements taken three times. During the third reading at 10 cm-$H_2O$ pressure the comfort of the mask seal was graded 1 to 10 by the participant, where 10 is the most comfortable.
5. Relative head circumference was measured using a sewing tape measure.

In FIGS. 45A and 45B, the acceptable regions for both seal leak and comfort are shown in white. For the gender specific male seal, the acceptable region encapsulates a substantial portion of the grey region between 83 mm and 103 mm of Sublabiale-Sellion height in FIG. 45B. It can be seen that the proposed seal is comfortable and seals well over a greater range of face sizes than the standard large seal. In some configurations, the seal size fit range of the gender specific masks disclosed above can be further improved by increasing the seal depth by, for example, 1-4 mm, between the face and the seal housing and increasing the nasal bridge movement away from the face by, for example, 1-4 mm. Moreover, the actual seal dimensions can be varied from the exemplary embodiments disclosed herein based on relevant factors, such as the locations at which it is desired for the seal to contact the user. However, preferably, the seal sizes include at least one seal dimensioned in view of facial data for a male population and at least one seal dimensioned in view of facial data for a female population. In some configurations, a system or kit includes only one seal dimensioned in view of facial data for a male population and only one seal dimensioned in view of facial data for a female population.

Automatic Fit Headgear

In at least some configurations, it can be beneficial to use the above-described masks, in particular, but not limited to, the gender specific masks in combination with an automatically adjusting or automatic fit headgear. In some configurations, such headgear is configured to allow a user to don the interface and the headgear automatically retracts to a suitable fit condition. The headgear can resist forces expected or normally incurred during use, which can include blow-off forces and, in some configurations, can include hose pull forces. Embodiments of such headgear are disclosed in WO 2014/175752 A2 and U.S. Provisional App. No. 62/062,720 entitled HEADGEAR ASSEMBLIES AND INTERFACE ASSEMBLIES WITH HEADGEAR, filed Oct. 10, 2014, the entireties of which are incorporated by reference herein and are included as an appendix filed with this application.

Some embodiments involve a headgear system and/or an interface assembly incorporating a headgear system that upon fitment to the head of a user automatically adjusts to the correct size and, once in use, transforms in properties from an elasticated "stretchy" strap/strapping to an "inelastic" strap/strapping. In some configurations, the headgear (alone or as integrated in an interface assembly) exhibits a relatively small contraction force that tends to shorten the headgear. When coupled to a mask, the headgear and mask cooperate to define a perimeter of the interface assembly, which is reduced in length as a result of the contraction force toward a minimum perimeter length. Although not likely to be perfectly circular, the perimeter length is often referred to as a "circumference." Thus, with such an arrangement, the interface assembly can be positioned on the user's head and will automatically contract to or very near a proper head size, in a manner similar to an elasticated or "stretchy" headgear. The contraction force preferably is sufficient to support the weight of the interface assembly and at least substantially keep the interface assembly in place on the user's head at the smallest head size or minimum useful perimeter length of the interface assembly, which may or may not coincide with the minimum perimeter length. In some configurations, the retraction force can be sufficient to support the weight of the interface. In other configurations, the retraction force may be insufficient to support the weight of the interface and may require manual assistance to move the interface to a sealed position on the user's face. However, preferably, once the headgear is sufficiently retracted, it is then held in place by, for example, the directional lock(s). In some configurations, the contraction force is only sufficient or is configured to support the weight of the headgear.

However, in at least some configurations, the contraction force is less than is necessary to maintain the mask in sealed contact with the user's face during treatment/use. That is, the contraction force, alone, cannot resist the blow-off force. In some configurations, the contraction force is insufficient to resist the blow-off force throughout a range of usable perimeter lengths or headgear sizes. Therefore, the headgear and/or interface assembly also exhibits an inelastic behavior in response to forces tending to elongate the headgear or increase the perimeter length of the interface assembly. The headgear and/or interface assembly can have a locked mode that can produce a locking force tending to resist expansion, elongation or lengthening of the perimeter length. The locking force can be sufficient to resist elongation, or at least any significant elongation, of the perimeter length in response to blow-off forces. In some configurations, the locking force is sufficient to resist elongation in response to the highest blow-off forces expected with a variety of uses or treatments (e.g., Bi-Level or CPAP, NIV, etc.). In some configurations, the locking force may be selected for one or more particular uses/therapies, but may not be suitable for all uses/therapies. In some configurations, the locking force may be selected to resist elongation in response to forces in addition to blow-off forces, such as hose pull forces, for example. Such additional forces can be referred to collectively as "hose pull forces" and such additional resistance to elongation can be referred to as a "reserve."

In some configurations, the headgear and/or interface assembly also exhibits a yield force, above which expansion or elongation of the perimeter length is permitted. Preferably, the yield force is greater than the expected blow-off force. In some configurations, the yield force is greater than the expected blow-off force and the hose pull force. Thus, such a headgear and/or interface assembly has a reserve. Preferably, the yield force is set low enough that a user can at least relatively conveniently apply an elongation force to the headgear and/or interface assembly sufficient to exceed the yield force in order to permit the interface assembly to lengthen and to be applied to the user's head. The contraction force reduces the perimeter length toward a proper head size.

In some configurations, the headgear and/or interface assembly automatically transitions between a contraction mode, a locked mode and a yield mode in response to the presence or absence of external forces. For example, the headgear and/or interface assembly moves toward or to the minimum perimeter length in the absence of external lengthening or expanding forces. A lengthening or expansion force that is greater than the yield force can be applied to increase the perimeter length of the headgear and/or interface assembly to a length sufficient to permit the interface assembly to be positioned on the user's head. Once the lengthening or expansion force is removed (or reduced to below the contraction force), the contraction force acts to automatically reduce the perimeter length to or substantially to the proper head size such that the interface assembly is supported on the user's head. Upon the start of treatment (application of blow-off force) and/or application of hose pull force, the headgear and/or interface assembly automatically transforms to the locked mode to resist elongation, or at least resist any significant elongation, or increase of the perimeter length. At the end of treatment, or at any time as desired, a force above the yield force can be applied to the headgear and/or interface assembly to increase the perimeter length and permit removal of the interface assembly from the user's head.

Advantageously, with such an arrangement, micro-adjustments of the perimeter length of the headgear and/or interface assembly can be accomplished quickly and conveniently. For example, during treatment or use, the mask can be manipulated to effect micro-adjustment of the perimeter length. For instance, in the event of a leak between the mask and the user's face, the mask can be wiggled or otherwise moved to affect a micro-adjustment of the perimeter length to address the leak. In some cases, the seal of the mask may be compressed against the user's face, which can allow the contraction force to automatically reduce the perimeter length. Upon release of the mask, the headgear and/or interface assemblies lock at, or very near, the reduced perimeter length. Thus, such configurations permit the headgear and/or interface assembly to micro-adjust, or move to an adjusted perimeter length, as a result of small manipulations (e.g., wiggling) of the mask. Manipulation of other portions of the interface assembly (e.g., headgear or breathing tube/gases conduit) can similarly result in micro-adjustment. Because of the nature of the human head and/or the conditions under which interface assemblies are used, quick and convenient micro-adjustment can dramatically improve performance and user satisfaction of an interface assembly. Treatment often occurs at night and/or under other situations when the user is lying down. Thus, the headgear can be in contact with surface, such as a pillow or bed. Movement of the user's head relative to such surfaces can cause movement of the headgear, which can alter the fit of the headgear. For example, hair can move or "compress" beneath the headgear, which can alter the fit. The headgear straps may move up, down or rotationally on the head, which can alter the fit. Such alterations in fit can result in leaks between the mask and the user's face. The above-described adjustment technology can permit such changes in fit to be addressed automatically or with small manipulations of the mask or other portions of the interface assembly. Moreover, the interface assembly can be removed and reapplied and automatically adjust to at or very near a proper headgear size. In contrast, if conventional non-stretch headgear is moved from its desired adjustment position, such as by mistake or as a result of cleaning, it can be difficult and time-consuming to reestablish the desired adjustment position. Conventional elasticated headgear addresses the adjustment issue, but because the contraction force must resist the highest expected blow-off and hose pull forces at the smallest useable headgear size, elasticated headgear applies a relatively large pressure to the user's head that is only partially relieved by the application of blow-off force. Such pressure may be substantial for a user with a relatively large head size and low treatment pressure.

In some configurations, some amount of movement occurs in the headgear and/or interface assembly during transition from the elastic mode to the locked mode. For example, with some directional lock arrangements, the perimeter length may increase slightly during the transition from elastic mode to locked mode. In some cases, there exists a compromise between increased yield force and reduced perimeter length change during transition. Thus, references to any particular positions of the headgear and/or interface assembly or perimeter lengths can include such slight length changes during transition, if present.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A mask system comprising:
   a seal support; and
   a first seal and a second seal that are interchangeably mountable to the seal support, the first seal having a first size and a second seal having a second size different than the first size,
   wherein the first size is based on facial geometry data of a female population sample and wherein the second size is based on facial geometry data of a male population sample;
   wherein a height of each of the first seal and the second seal is measured between two points located at a mid-point of a sealing surface of the first and/or second seal on a vertical center line, a first point of the two points being located at a nasal bridge region of each of the first and second seals, a second point of the two points being located at a chin region of each of the first and second seals,
   wherein a first width of each of the first and second seals is measured between two lateral points on a perimeter of an internal seal opening,
   wherein the first width of the each of the first and second seals is based on or is the same as a median Cheilion length for the female and male populations respectively; and
   wherein the height of the first and second seal is based upon or determined by subtracting 5 mm from a median sublabial-sellion length of the female or male population respectively,
   wherein a second width of the first seal fits a max Cheilion length of 65 mm measured between midpoints of the first seal, and a second width of the second seal fits a max Cheilion length of 76 mm measured between midpoints of the second seal.

2. The mask system of claim 1, wherein the height of the first size is about 81 mm and the first width of the first size is about 50.5 mm.

3. The mask system of claim 1, wherein the height of the second size is about 90.5 mm and the first width of the second size is about 56.5 mm.

4. The mask system of claim 1, wherein a Cheilion length between 51.5 mm and 59.5 mm is sealed by both the first size and the second size.

5. The mask system of claim 1, wherein a sublabiale-sellion height between 83 mm and 103 mm is sealed by the second size.

6. The mask system of claim 1, wherein a sublabiale-sellion height between 84.5 mm and 96 mm is sealed by both the first size and the second size.

7. The mask system of claim 1, wherein the first width of the second size is approximately 0% to 22.9% greater than the first width of the first size.

8. The mask system of claim 7, wherein the first width of the second size is approximately 11.9% greater than the first width of the first size.

9. The mask system of claim 1, wherein the first width of the second size is approximately 1 mm to 11 mm greater than the first width of the first size.

10. The mask system of claim 9, wherein the first width of the second size is approximately 6 mm greater than the first width of the first size.

11. The mask system of claim 1, wherein a difference in the heights is approximately twice a difference in the first widths between the first size and the second size.

12. The mask system of claim 1, wherein a difference in the heights between the first size and the second size is equal to or less than 9.5 mm.

13. The mask system of claim 1, wherein the difference in the heights between the first size and the second size is equal to or less than 11.7%.

14. The mask system of claim 1, wherein the first width of the first size is between 57.5% to 67.5% of the height of the first size.

15. The mask system of claim 14, wherein the first width of the first size is 62.3% of the height of the first size.

16. The mask system of claim 1, wherein the first width of the second size is between 58.1% to 67.0% of the height of the second size.

17. The mask system of claim 16, wherein the first width of the second size is 62.4% of the height of the second size.

18. The mask system of claim 1, wherein the first size and the second size have equal width versus height proportions.

19. The mask system of claim 1, wherein an upper portion of the first and second seals each include a seal having a forwardly-deflectable upper portion, wherein the heights are measured in a relaxed position of the forwardly-deflectable upper portions.

20. The mask system of claim 19, wherein the forwardly-deflectable upper portion rolls in a forward direction relative to a lower portion of the seal.

* * * * *